US010532113B2

(12) United States Patent
Satchi-Fainaro et al.

(10) Patent No.: US 10,532,113 B2
(45) Date of Patent: Jan. 14, 2020

(54) POLYMERIC SYSTEMS AND USES THEREOF IN THERANOSTIC APPLICATIONS

(71) Applicant: Ramot at Tel-Aviv University Ltd., Tel-Aviv (IL)

(72) Inventors: Ronit Satchi-Fainaro, Tel-Aviv (IL); Doron Shabat, Tel-Aviv (IL); Rachel Blau, Tel-Aviv (IL); Yana Epshtein, Tel-Aviv (IL); Hemda Baabur-Cohen, Tel-Aviv (IL); Shiran Ferber, Tel-Aviv (IL); Orit Redy-Keisar, Tel-Aviv (IL); Einat Kisin-Finfer, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 15/124,360

(22) PCT Filed: Mar. 13, 2015

(86) PCT No.: PCT/IL2015/050269
§ 371 (c)(1),
(2) Date: Sep. 8, 2016

(87) PCT Pub. No.: WO2015/136545
PCT Pub. Date: Sep. 17, 2015

(65) Prior Publication Data
US 2017/0014531 A1 Jan. 19, 2017

Related U.S. Application Data

(60) Provisional application No. 61/852,259, filed on Mar. 13, 2014.

(51) Int. Cl.
| A61K 49/00 | (2006.01) |
| A61K 31/337 | (2006.01) |
| A61K 47/65 | (2017.01) |
| A61K 47/58 | (2017.01) |
| A61K 47/59 | (2017.01) |

(52) U.S. Cl.
CPC ........ *A61K 49/0054* (2013.01); *A61K 31/337* (2013.01); *A61K 47/58* (2017.08); *A61K 47/593* (2017.08); *A61K 47/65* (2017.08); *A61K 49/0032* (2013.01)

(58) Field of Classification Search
CPC ............ A61K 31/337; A61K 47/48176; A61K 47/482; A61K 47/48338; A61K 49/0032; A61K 49/0054
See application file for complete search history.

(56) References Cited

U.S. PATENT DOCUMENTS

| 2009/0220430 A1* | 9/2009 | Rajopadhye ....... A61K 49/0032 424/9.6 |
| 2011/0003312 A1* | 1/2011 | Berget ..................... C12Q 1/37 435/7.4 |
| 2012/0122734 A1 | 5/2012 | Lu et al. | |

FOREIGN PATENT DOCUMENTS

| WO | WO 2012/024543 | 2/2012 |
| WO | WO 2012/123916 | 9/2012 |
| WO | WO 2015/136545 | 9/2015 |

OTHER PUBLICATIONS

Galande et al. (Bioconjugate Chem., vol. 17, No. 2, 2006 255-257).*
Satchi-Fainaro et al. (Pub. No. US2011/0286923; Pub Date: Nov. 24, 2011).*
International Preliminary Report on Patentability dated Sep. 22, 2016 From the International Bureau of WIPO Re. Application No. PCT/IL2015/050269.
International Search Report and the Written Opinion dated Jul. 1, 2015 From the International Searching Authority Re. Application No. PCT/IL2015/050269.
Ferber et al. "Polymeric Nanotheranostics for Real-Time Non-Invasive Optical Imaging of Breast Cancer Progression and Drug Release", Cancer Letters, 352(1): 81-89, Epub Mar. 12, 2014.
Johansson "Choosing Reporter-Quencher Pairs for Efficient Quenching Through Formation of Intramolecular Dimers", Methods in Molecular Biology: Fluorescent Energy Transfer Nucleic Acid Probes: Designs and Protocols, 335(Chap.2): 17-29, 2006.
Johansson et al. "Intramolecular Dimers: A New Strategy to Fluorescence Quenching in Dual-Labeled Oligonucleotide Probes", Journal of the American Chemical Society, JACS, 124(24): 6950-6956, Published on Web May 21, 2002.
Jones et al. "Superquenching and Its Applications in J-Aggregated Cyanine Polymers", Langmuir, 17(9): 2568-2571, Published on Web Apr. 4, 2001.
Karton-Lifshin et al. A Unique Paradigm for A Turn-On Near-Infrared Cyanine, Journal of the Chemical Society, JACS, 133(28): 10960-10965, Jun. 2, 2011.
Kisin-Finfer et al. "Synthesis and Evaluation of New NIR-Fluorescent Probes for Cathepsin B: ICT Vs. FRET as a Turn-ON Mode-of-Action", Bioorganic & Medicinal Chemistry Letters, 24(11): 2453-2458, Epub Apr. 16, 2014.
Kobayashi et al. "New Stategies for Fluorescent Probe Design in Medical Diagnostic Imaging", Chemical Reviews, 110(5): 2620-2640, Published on Web Dec. 15, 2009.
Krasia-Christoforou et al. "Polymeric Theranostics: Using Polymer-Based Systems for Simutaneous Imaging and Therapy", Journal of Materials Chemistry B, 1: 3002-3025, 2013.
Lee et al. "Activatable Imaging Probes With Amplified Fluorescent Signals", Chemical Communications, 36: 4250-4260, Sep. 28, 2008.

(Continued)

*Primary Examiner* — Anna R Falkowitz

(57) ABSTRACT

Polymeric systems useful for theranostic applications are disclosed. The polymeric systems comprise a fluorescent or fluorogenic moiety and a therapeutically active agent, each attached to the same or different polymeric moiety. The polymeric systems are designed such that a fluorescent signal is generated in response to a chemical event, preferably upon contacting an analyte (e.g., an enzyme) that is over-expressed in a diseased tissue or organ. Probes useful for inclusion in such polymeric systems, processes of preparing such probes and the polymeric systems, and uses thereof in diagnostic and/or theranostic applications are also disclosed.

6 Claims, 48 Drawing Sheets
(14 of 48 Drawing Sheet(s) Filed in Color)

(56) References Cited

OTHER PUBLICATIONS

Lee et al. "Activatable Molecular Probes for Cancer Imaging", Current Topics in Medicinal Chemistry, 10(11): 1135-1144, 2010.
Luk et al. "Current Advances in Polymer-Based Nanotheranostics for Cancer Treatment and Diagnosis", Applied Materials & Interfaces, 6: 21859-21873, Jul. 11, 2014.
Melancon et al. "A Novel Method for Imaging In Vivo Degradation of Poly(L-Glutamic Acid), A Biodegradable Drug Carrier", Pharmaceutical Research, 24(6): 1217-1224, Jun. 2007.
Morton et al. "FRET-Enabled Biological Characterization of Polymeric Micelles", Biomaterials, 35(11): 3489-3496, Apr. 2014.
Ofek et al. "Rational Design of Multifunctional Polymer Therapeutics for Cancer Theranostics", Israel Journal of Chemistry, IJC, 50(2): 185-203, Published Online Aug. 2, 2010.
Redy et al. "A Simple FRET-Based Modular Design for Diagnostic Probes", Organic & Biomolecular Chemistry, 10(4): 710-715, 2012.
Redy-Keisar et al. "NIR Fluorogenic Dye as a Modular Platform for Prodrug Assembly: Real-Time In Vivo Monitoring of Drug Release", ChemMedChem, p. 1-28, 2015.
Redy-Keisar et al. "Synthesis and Use of QCy7-Derived Modular Probes for the Detection and Imaging of Biologically Relevant Analytes", Nature Protocols, 9(1): 27-36, 2014.
Weinstain et al. "Real-Time Monitoring of Drug Release", Chemical Communications, 46(4): 553-555, Advanced Article Published on Dec. 10, 2009.

* cited by examiner

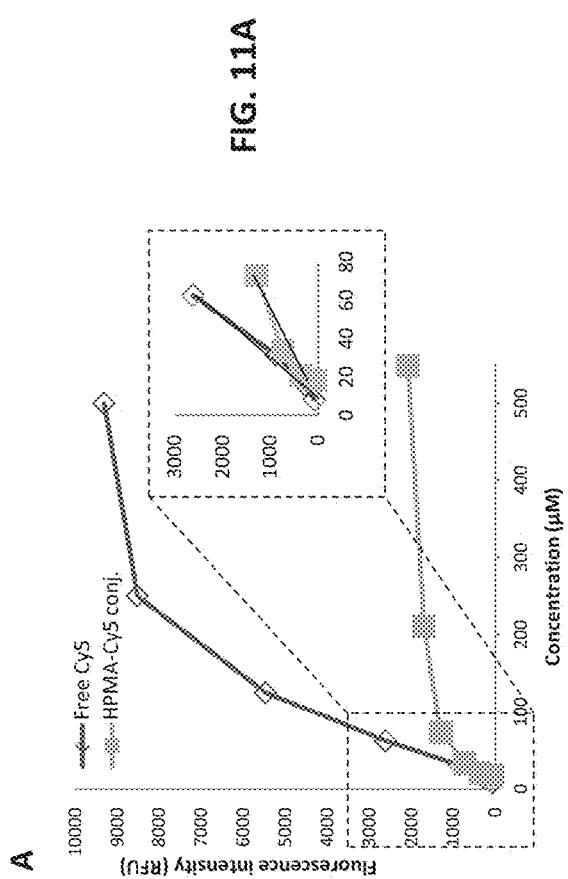
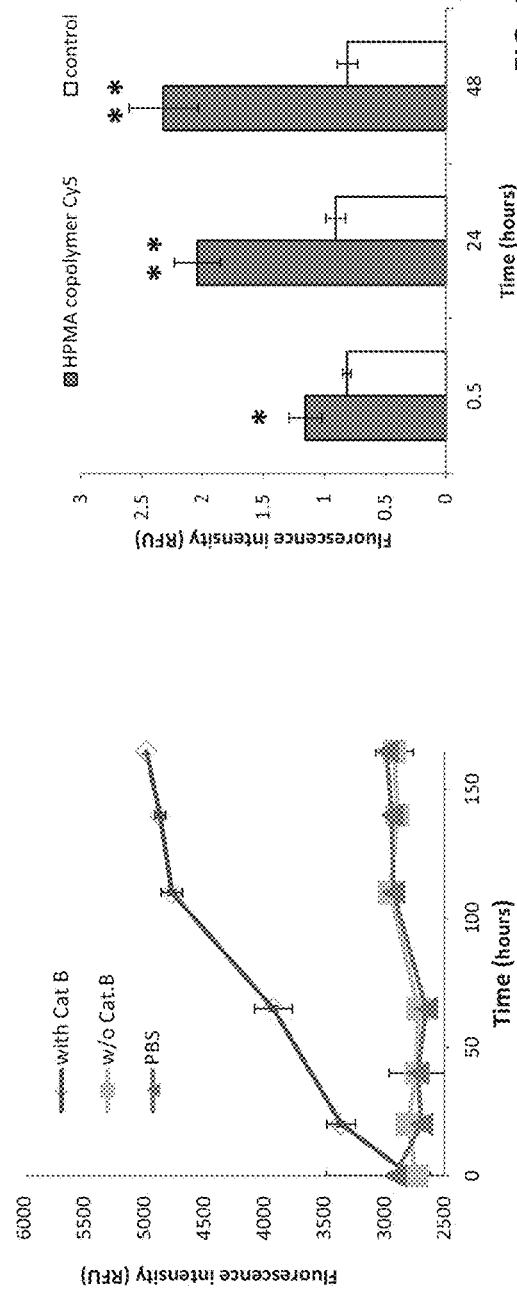
FIG. 11A
FIG. 11B
FIG. 11C

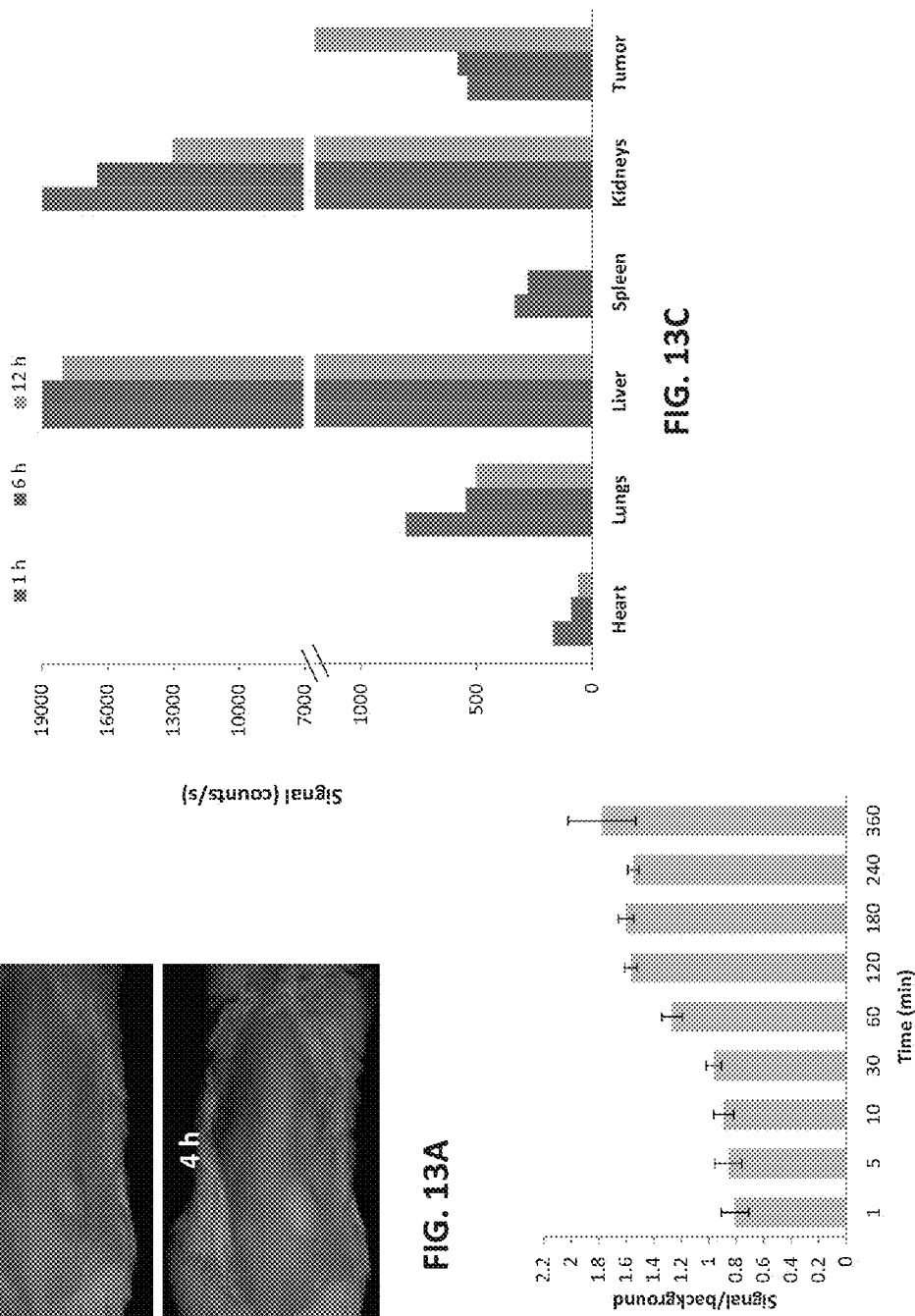
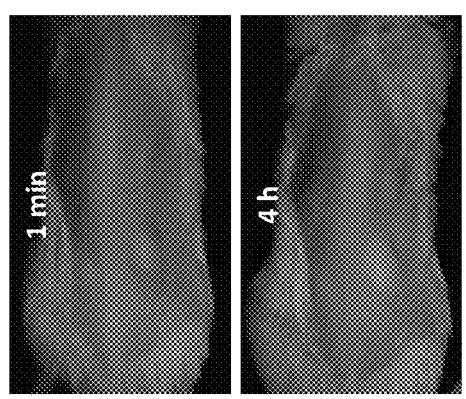
FIG. 13A
FIG. 13B
FIG. 13C

POLYMERIC SYSTEMS AND USES THEREOF IN THERANOSTIC APPLICATIONS

RELATED APPLICATIONS

This application is a National Phase of PCT Patent Application No. PCT/IL2015/050269 having International filing date of Mar. 13, 2015, which claims the benefit of priority under 35 USC § 119(e) of U.S. Provisional Patent Application No. 61/952,259 filed on Mar. 13, 2014. The contents of the above applications are all incorporated by reference as if fully set forth herein in their entirety.

FIELD AND BACKGROUND OF THE INVENTION

The present invention, in some embodiments thereof, relates to therapy and diagnosis (theranostic) and, more particularly, but not exclusively, to polymeric systems in which a labeling moiety (e.g., a fluorescent or fluorogenic moiety) or a labeling moiety and a therapeutically active agents are attached to a polymeric backbone, and to uses thereof in diagnostic and theranostic applications.

In the past few years, tremendous efforts have been employed in monitoring cancer treatment, detecting response to drugs and measuring real-time accumulation of the drug within the tumor. Numerous nanocarrier systems have been developed (e.g., polymers, liposomes, micelles, dendrimers, etc.) and studied as delivery vehicles for anticancer drugs to improve the drugs' biodistribution, solubility, and half-life, and thus to exhibit enhanced efficacy and reduced toxicity. Clinically-available fluorescence-based imaging contrast agents (e.g., indocyanine green and fluorescein) hold many of the limitations attributed to chemotherapeutic agents, including low molecular weight, short half-life and poor selectivity. Consequently, monitoring slow processes, such as drug accumulation at the tumor site, is challenging.

Combining therapeutic and diagnostic modalities on the same delivery system, thereby forming a theranostic (therapy and diagnostic) nanomedicine, may overcome these limitations, while enabling simultaneous monitor and treatment of angiogenesis-dependent diseases, like cancer [Kelkar, S. S. and T. M. Reineke, *Theranostics: Combining Imaging and Therapy*. Bioconjug Chem, 2011. 22(10): p. 1879-1903]. Information obtained from theranostic nanomedicine is exploited for fine tuning the therapeutic dose, while monitoring the progression of the diseased tissue, treatment efficacy and delivery kinetics [Janib et al. Adv Drug Deliv Rev, 2010. 62(11): p. 1052-1063; McCarthy, J. R., *The future of theranostic nanoagents*. Nanomedicine, 2009. 4(7): p. 693-695]. This, from a clinical prospective, should enhance early diagnosis and treatment and may decrease drugs under- or over-dosing, resulting in a more personalized treatment.

Among different imaging modalities (e.g., radiography, magnetic resonance imaging and ultrasound), optical imaging holds several advantages. Fluorescent molecular probes are highly sensitive, possess a high spatial resolution, enable simultaneous multicolor imaging and specificity, by signal activation in the tissue of interest, they may possess high target to background ratio (TBR), and are relatively inexpensive. Furthermore, they do not hold long term health risks, like other commonly-used computed tomography (e.g., PET—positron emission tomography and SPECT—single-photon emission computed tomography), which expose the patient to ionizing radiation.

An ideal theranostic nanomedicine system should hold (i) long circulation time in the body, (ii) high specificity to the target tissue, (iii) an efficient release mechanism, (iv) an imaging probe that enables monitoring its activity, (v) deep tissue penetration, and (vi) high target-to-background (TBR) ratio. High specificity can be obtained via passive targeting, by exploiting the enhanced permeability and retention (EPR) effect or via an additional functional targeting moiety.

In contrast to thin layer imaging of cells or surfaces, the signal from fluorescent probes in vivo is impeded by the emitted fluorescence from tissues and biomolecules (e.g., water, melanin, proteins and hemoglobin), which absorb photons in the wavelengths range of 200-650 nm (i.e., low signal-to-noise ratio). In addition, tissues contribute to reflection, refraction and scattering of incident photons, thus increasing the background and blur of the obtained image. The 'imaging wavelength window' left for intravital imaging in order to overcome these obstacles is at the near infra-red (NIR) range (i.e., 650-1450 nm). In this range, auto-fluorescence is minimal and scattering of light is reduced, enabling deep tissue penetration and facilitating non-invasive monitoring.

One way to maximize the signal from the target and to minimize the signal from background (i.e., high TBR ratio), is the use of activatable optical probes. The fluorescent signal is silenced/"OFF" under physiological conditions, and is turned-ON at a designated site and/or under specific conditions [Lee et al., *Activatable molecular probes for cancer imaging*. Vol. 10. 2010. 1135-44].

Although numerous classes of Turn-ON optical probes have been described in the literature for detection of chemical and biological factors [Karton-Lifshin, N., et al., J Am Chem Soc, 2011. 133(28): p. 10960-5; Kobayashi, H., et al., Chem Rev, 2010. 110(5): p. 2620-40; Lee, S., et al., Chem Commun (Camb), 2008(36): p. 4250-60; Redy-Keisar, O., et al., Nat Protoc, 2014. 9(1): p. 27-36; Weinstain, R., et al., Chem Commun (Camb), 2010. 46(4): p. 553-5], to this point, most polymer-based theranostic nanomedicines studies utilize an 'always ON' theranostic systems. In these systems, a fluorescent signal is obtained from the background and desired site at once, resulting in low TBR.

Among methods used to obtain a selective Turn-ON mechanism, Förster resonance energy transfer (FRET) is the most common and efficient. Using FRET technique to monitor drug release, two types of fluorophores are incorporated into the core of drug-carrying nanoparticles and serve as energy donors and acceptors. In this process, following excitation of the donor, the acceptor will absorb the emission energy of the donor and will turn off the fluorescent signal. The donor and the acceptor are required to have overlapping emission and absorbance spectra, as well as close proximity between them. A FRET-based probe is turned-ON upon distance that results in the diffusion of the donor fluorophore away from the acceptor, and generation of a measurable fluorescent signal [Lee et al. 2010 supra; Johansson, M. K., et al., Journal of the American Chemical Society, 2002. 124(24): p. 6950-6956]. This process includes two approaches, fluorophore-fluorophore (self-quenching) and fluorophore-quencher activation. The donor is always a fluorophore, however the acceptor can be either a quencher—a dye with no native fluorescence (FRET) or a second fluorophore (self-quenching) [Redy, O., et al., Org Biomol Chem, 2012. 10(4): p. 710-5].

In the fluorophore-fluorophore (self-quenching) approach, excited fluorophores of similar type absorb the energy from each other that would otherwise have led to an emitted photon, thus reducing the fluorescence of the entire compound. This can occur when the excitation and emission peaks overlap or when the Stokes shift is small, like in the case of Cy5. Hence, the fluorophore can serve as a quencher and adsorb the excitation energy. Under these circumstances the emitted energy from one fluorophore is absorbed by another fluorophore (self-quenching) [Melancon, M. P., et al., Pharm Res, 2007. 24(6): p. 1217-24].

Self-quenching involving only fluorophores may still yield weak fluorescence even in the quenched state. A second alternative to fluorophore-fluorophore quenching, is to use a fluorophore-quencher combinations in which the quencher is non-fluorescent and plays as the acceptor, whereas the donor is a fluorophore. When a FRET fluorophore-quencher process occurs, the excited fluorophore can transfer its emission energy to the nearby quencher [Redy, O., et al., Org Biomol Chem, 2012. 10(4): p. 710-5].

Optical imaging in the near-infrared (NIR) range enables detection of molecular activity in vivo clue to high penetration of NIR photons through organic tissues and low auto-fluorescence background. Cyanine dyes are widely employed as fluorescence labels for NIR imaging, since they are compounds with large extinction coefficient and relatively high quantum yield.

In order to generate a Turn-ON system for a cyanine molecule, a FRET (fluorescence resonance energy transfer) approach is usually applied. In such approach, the cyanine dye and a quencher are attached through a specific linker to obtain a quenched fluorophore. A linker, which is cleaved by a specific enzyme, separates the fluorophore from the quencher and thus, turn-ON its fluorescence signal. Exemplary such FRET-based probes are described in Redy, O., et al., Org Biomol Chem, 2012. 10(4): p. 710-5, which is incorporated by reference as if fully set forth herein. An alternative approach, to turn OFF and ON a fluorophore, could be achieved by disrupting the pull-push conjugated π-electron system of the dye. Such a concept, referred to as internal Charge Transfer (ICT) probe, is described in WO 2012/123916, which is incorporated by reference as if fully set forth herein, and in Kisin-Finfer E., et al., 1; 24(11): 2453-8; Bioorg Med Chem Lett. 2014, which is also incorporated by reference as if fully set forth herein.

Additional background art includes Jones et al. Langmuir, 2001, 17 (9), pp 2568-2571; U.S. Patent Application Publication No. 20120122734; Theodora Krasia-Christoforou and Theoni K. Georgiou, J. Mater. Chem. B, 2013, 1, 3002-3025; Morton et al., Biomaterials. 2014 April; 35(11): 3489-3496; and Luk and Zhang, Appl. Mater. Interfaces 2014, 6, 21859-21873.

SUMMARY OF THE INVENTION

Although polymeric nanocarriers conjugated to low molecular weight drugs greatly improve their efficacy and toxicity profile, these nanocarriers lack information concerning drug-release time and location. Combining therapeutic and diagnostic modalities on the same delivery system, thereby forming theranostic (therapy and diagnostic) nanomedicine, enables simultaneous monitor and treatment of angiogenesis-dependent diseases, like cancer. Information obtained from theranostic nanomedicines allows tuning therapy dose, while monitoring diseased tissue and delivery kinetics. This, from a clinical prospective, may increase early detection of disease and decrease drug under-dosing or over-dosing, resulting in a more personalized treatment.

The present inventors have now designed various theranostic systems, which are based on a polymeric system in which a fluorogenic moiety is attached to a portion of the backbone units composing the polymeric backbone of a polymeric moiety, wherein the fluorogenic moiety is attached to the backbone units via a cleavable linking such that upon cleavage of the linking moiety, a fluorescent moiety is generated, and a detectable signal can be measured.

According to an aspect of some embodiments of the present invention there is provided a polymeric system comprising a first polymeric moiety comprising a polymeric backbone composed of a plurality of backbone units and having attached to at least a portion of the backbone units a fluorogenic moiety, the fluorogenic moiety being attached to the backbone units via a first cleavable linking moiety such that upon cleavage of the linking moiety, a fluorescent signal is generated, the system further comprising a therapeutically active agent, such that: (i) the fluorogenic moiety is attached to one portion of the backbone units and the therapeutically active agent is attached to another portion of the backbone units; (ii) the therapeutically active agent forms a part of the fluorogenic moiety; (iii) the therapeutically active agent is attached to the first cleavable linking moiety; or (iv) the system further comprises a second polymeric moiety comprising a second polymeric backbone composed of a plurality of backbone units and having attached to at least a portion of the backbone units a therapeutically active agent.

According to some of any of the embodiments described herein, upon the cleavage, a fluorescent moiety is generated.

According to some of any of the embodiments described herein, the fluorescent moiety emits UV-vis light.

According to some of any of the embodiments described herein, the fluorescent moiety emits near infrared light.

According to some of any of the embodiments described herein, the fluorescent moiety is or comprises a cyanine dye.

According to some of any of the embodiments described herein, the first cleavable linking moiety is a first biocleavable linking moiety.

According to some of any of the embodiments described herein, the first cleavable linking moiety is an enzymatically-cleavable linking moiety.

According to some of any of the embodiments described herein, the first polymeric moiety further comprises a quenching agent.

According to some of any of the embodiments described herein, the fluorogenic agent is attached to one portion of the backbone units and the quenching agent is attached to another portion of the backbone units.

According to some of any of the embodiments described herein, the quenching agent forms a part of the fluorogenic moiety.

According to some of any of the embodiments described herein, the fluorogenic moiety is represented by, or comprises a moiety represented by, formula II:

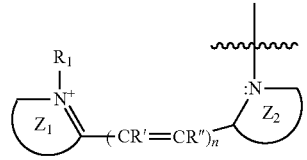

Formula II wherein:

$Z_1$ and $Z_2$ are each independently a substituted or unsubstituted heterocylic moiety;

$R_1$ is hydrogen, a substituted or unsubstituted alkyl or a substituted or unsubstituted cycloalkyl;

n is an integer of from 1 to 10; and

R' and R" are each independently hydrogen, a substituted or unsubstituted alkyl and a substituted or unsubstituted cycloalkyl, or, alternatively, R' and R" form together an aryl.

According to some of any of the embodiments described herein, $Z_1$ and $Z_2$ are each independently a substituted or unsubstituted heteroaryl.

According to some of any of the embodiments described herein, the fluorogenic moiety is represented by, or comprises a moiety represented by, formula IIA or IIB, as depicted herein.

According to some of any of the embodiments described herein, the fluorogenic moiety comprises a fluorescent moiety linked by the first cleavable linking moiety or by a degradable spacer to the quenching agent.

According to some of any of the embodiments described herein, the fluorogenic moiety is represented by a formula selected from Formula IIIA, IIIB, IIIC, and IIID, as depicted herein.

According to some of any of the embodiments described herein, the fluorogenic moiety is represented by Formula IV, as depicted herein.

According to some of any of the embodiments described herein, the fluorogenic moiety is attached to one portion of the backbone units and the therapeutically active agent is attached to another portion of the backbone units.

According to some of any of the embodiments described herein, the system further comprises a second polymeric moiety comprising a second polymeric backbone composed of a plurality of backbone units and having attached to at least a portion of the backbone units a therapeutically active agent.

According to some of any of the embodiments described herein, the therapeutically active agent is attached to the backbone units via a second cleavable linking moiety.

According to some of any of the embodiments described herein, the second linking moiety is a biocleavable linking moiety.

According to some of any of the embodiments described herein, the second linking moiety is an enzymatically-cleavable linking moiety.

According to some of any of the embodiments described herein, the first and second cleavable linking moieties are the same or are cleavable by the same mechanism (e.g., the same enzyme).

According to some of any of the embodiments described herein, the therapeutically active agent forms a part of the fluorogenic moiety, or is attached to the first cleavable linking moiety, and wherein upon the cleavage, the therapeutically active agent is released. According to some embodiments, upon the cleavage, a fluorescent moiety is generated.

According to some of any of the embodiments described herein, the fluorescent moiety is or comprises a cyanine dye.

According to some of any of the embodiments described herein, the therapeutically active agent forms a part of the fluorogenic moiety, and the fluorogenic moiety is represented by Formula VIA, VIB, VIC, or VID, as depicted herein.

According to some of any of the embodiments described herein, the therapeutically active agent forms a part of the fluorogenic moiety, and the fluorogenic moiety is represented by Formula IIIA, IIIB, IIIC or IIID, and wherein the therapeutically active agent is attached to one of the spacers or to the cleavable linking moiety.

According to some of any of the embodiments described herein, the therapeutically active agent forms a part of the fluorogenic moiety, and the fluorogenic moiety is represented by Formula IV, wherein the therapeutically active is attached to the donor moiety or to the cleavable linking moiety.

According to some of any of the embodiments described herein, the backbone units in the first polymeric backbone and/or in the second polymeric backbone, if present, form a polymeric backbone of HPMA co-polymer.

According to some of any of the embodiments described herein, the backbone units in the first polymeric backbone and/or in the second polymeric backbone, if present, form a polymeric backbone of a PGA polymer.

According to an aspect of some embodiments of the present invention there is provided a polymeric conjugate comprising a polymeric backbone composed of a plurality of backbone units and having attached to at least a portion of the backbone units a fluorogenic moiety, the fluorogenic moiety being attached to the portion of backbone units via a cleavable linking moiety such that upon cleavage of the linking moiety, a fluorescent moiety is generated, wherein the fluorescent moiety is a cyanine dye.

According to some of any of the embodiments described herein, the polymeric conjugate further comprises a quenching agent attached to the polymeric backbone.

According to some of any of the embodiments described herein, the fluorogenic moiety is represented by, or comprises a moiety represented by, formula II, as depicted herein.

According to some of any of the embodiments described herein, the fluorogenic moiety is represented by, or comprises a moiety represented by, formula IIA or IIB, as depicted herein.

According to some of any of the embodiments described herein, the fluorogenic moiety comprises a fluorescent moiety linked by a cleavable linking moiety and/or a degradable spacer to a quenching agent.

According to some of any of the embodiments described herein, the fluorogenic moiety is represented by a formula selected from Formula IIIA, IIIB, IIIC and IIID as depicted herein.

According to some of any of the embodiments described herein, the fluorogenic moiety is represented by Formula IV, as depicted herein.

According to some of any of the embodiments described herein, the polymeric conjugate further comprises a therapeutically active agent attached to the cleavable linking moiety or forming a part of the fluorogenic moiety, such that upon the cleavage, the therapeutically active agent is released.

According to an aspect of some embodiments of the present invention there is provided a polymeric system comprising a fluorogenic cyanine moiety covalently attached via a cleavable linking moiety to a quenching agent, such that upon cleavage of the linking moiety, a fluorescent cyanine moiety is generated, the system further comprising a polymeric moiety attached to the fluorogenic cyanine moiety.

According to some of any of the embodiments described herein, the polymeric system is represented by a formula selected from Formula VA or VB, as depicted herein.

According to some of any of the embodiments described herein, the cyanine moiety is attached to the polymeric moiety via a spacer.

According to some of any of the embodiments described herein, the polymeric system further comprises a therapeutically active agent, wherein:

(i) the therapeutically active agent is attached to the cleavable linking moiety;

(ii) the therapeutically active agent is attached to the degradable spacer; or (iii) the therapeutically active agent is attached to a second polymeric moiety.

According to an aspect of some embodiments of the present invention there is provided a polymeric system as described in any one of the embodiments described herein, where the system comprises a therapeutically active agent, for use in the treatment and diagnosis of a medical condition treatable by the therapeutically active agent, or for use in the preparation of a medicament for treating the medical condition.

According to an aspect of some embodiments of the present invention there is provided a method of treating a medical condition, the method comprising administering to a subject in need thereof a polymeric system as described herein, which comprises a therapeutically active agent that is usable in treating the medical condition.

According to some of any of the embodiments described herein, the medical condition is cancer.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-E present the chemical structure and cleavage mechanism by Cathepsin B of an exemplary HPMA copolymer-Cy5 (FIG. 1A); an exemplary HPMA copolymer-PTX and a release mechanism of PTX therefrom by cathepsin B (FIG. 1B); an exemplary HPMA copolymer-PTX-FK and a release mechanism of PTX therefrom by cathepsin B (FIG. 1C); an exemplary HPMA copolymer-Cy5-PTX (FIG. 1D), and an exemplary HPMA copolymer-Cy5-PTX-FK, according to some embodiments of the present invention.

Figure 2:
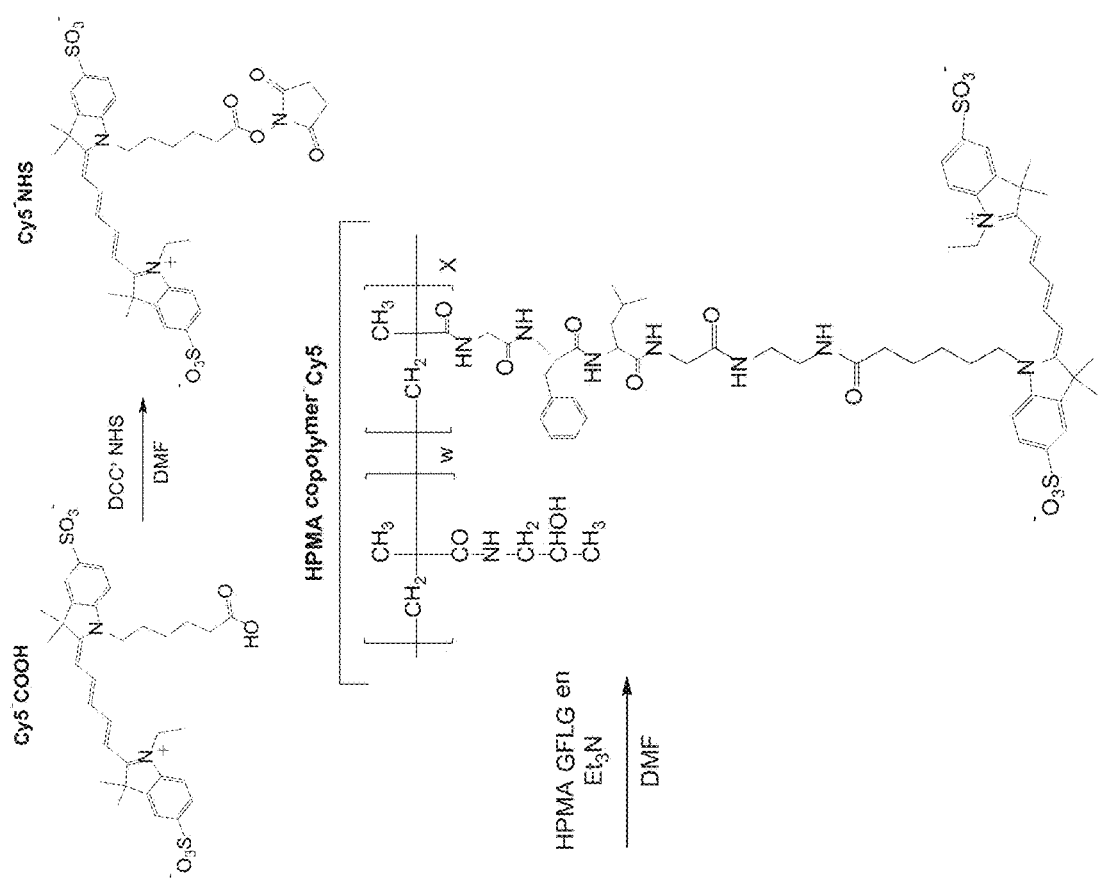

FIG. 2 is a scheme depicting a two-step synthesis of HPMA-GFLG-en 10% copolymer-Cy5 conjugate, carried out by activation of Cy5 with NHS group, followed by coupling with HPMA copolymer.

Figure 3:
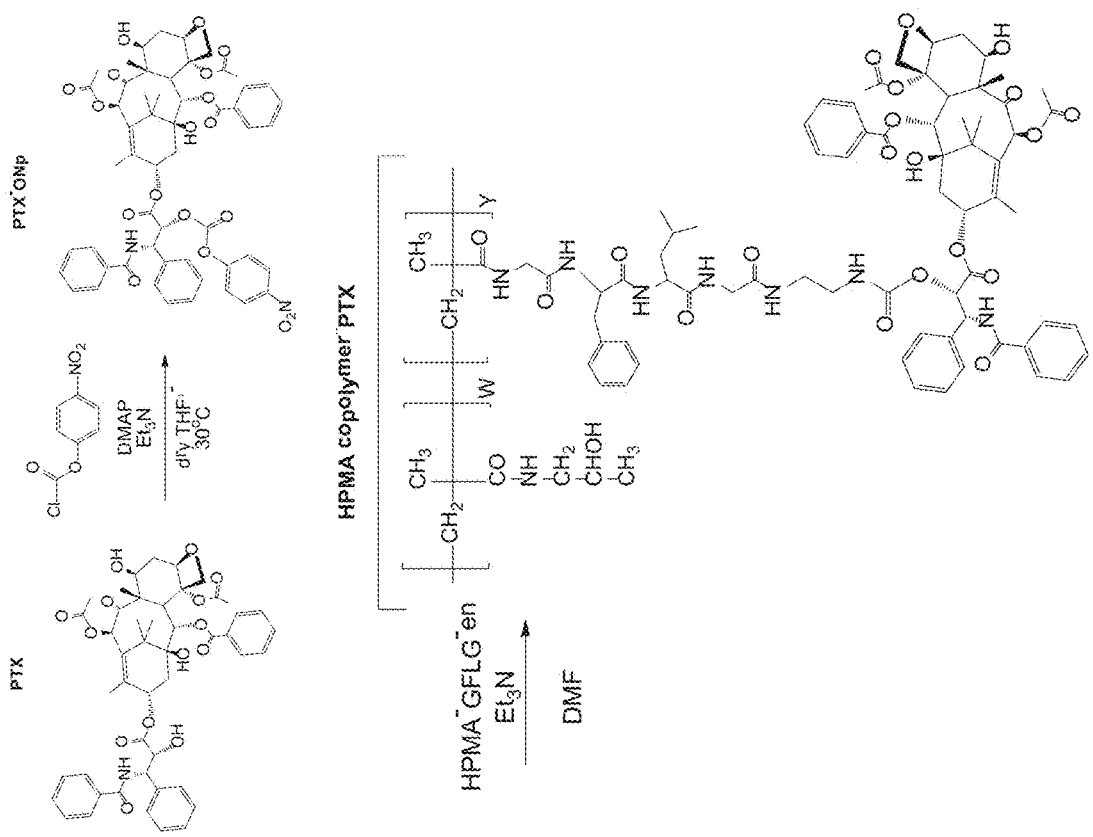

FIG. 3 is a scheme depicting a synthesis of HPMA copolymer-PTX conjugate, carried out by activation of PTX with PNp-Cl, followed by conjugation of HPMA to PTX, by mixing activated PTX with HPMA-GFLG-en 10 mol % copolymer.

Figure 4:
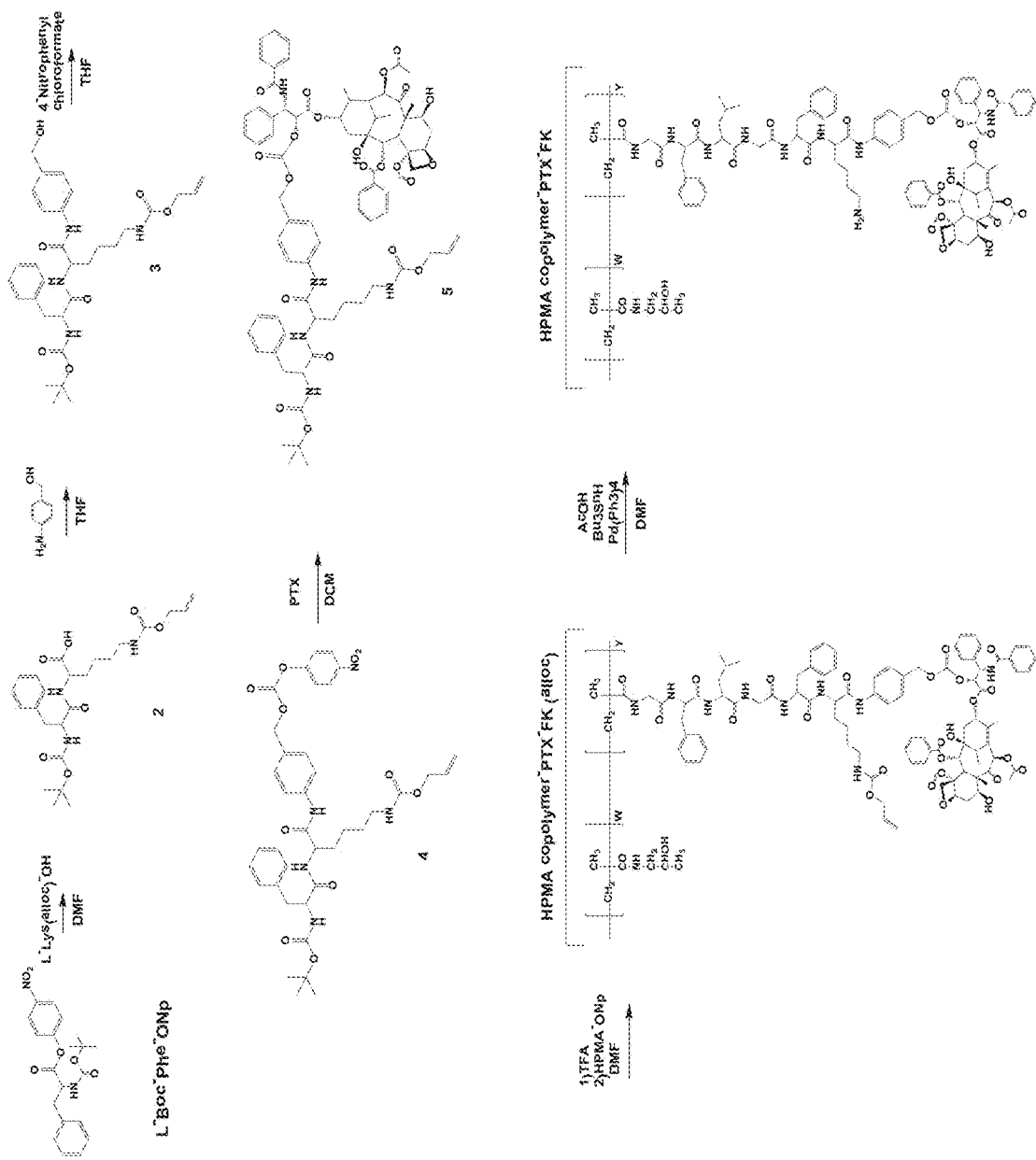

FIG. 4 is a scheme depicting a synthesis of HPMA copolymer-PTX-FK conjugate, carried out by forming a Phe-Lys-PABC linker and conjugating the linker to PTX, followed by coupling the PTX-Phe-Lys with HPMA copolymer.

Figure 5:
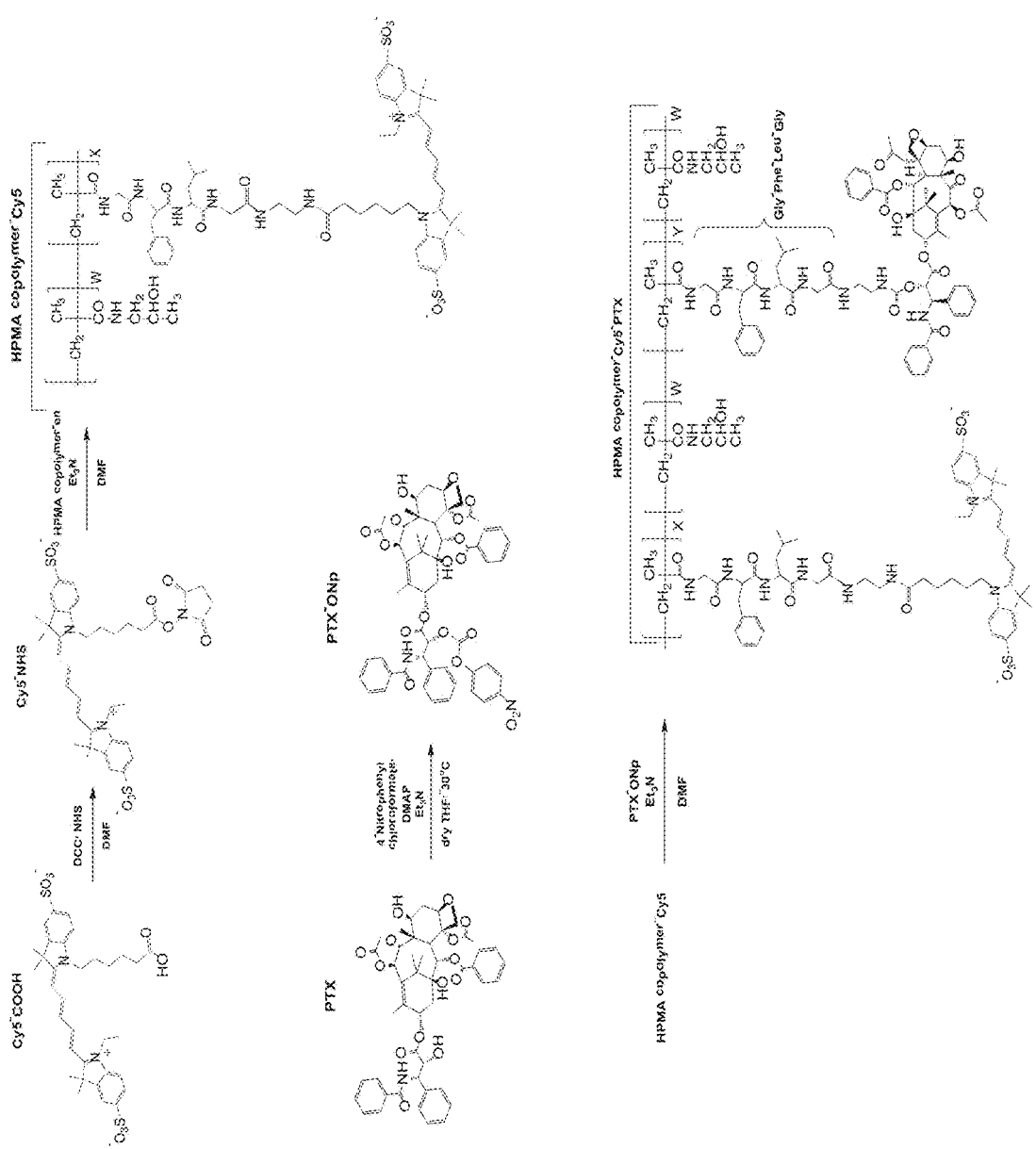

FIG. 5 is a scheme depicting a synthesis of HPMA copolymer-Cy5-PTX conjugate, carried out by conjugating of Cy5 to HPMA copolymer, and activation of PTX with 4-Nitrophenyl, followed by its conjugation to the HPMA copolymer-Cy5 so as to generate HPMA copolymer-Cy5-PTX.

Figure 6:
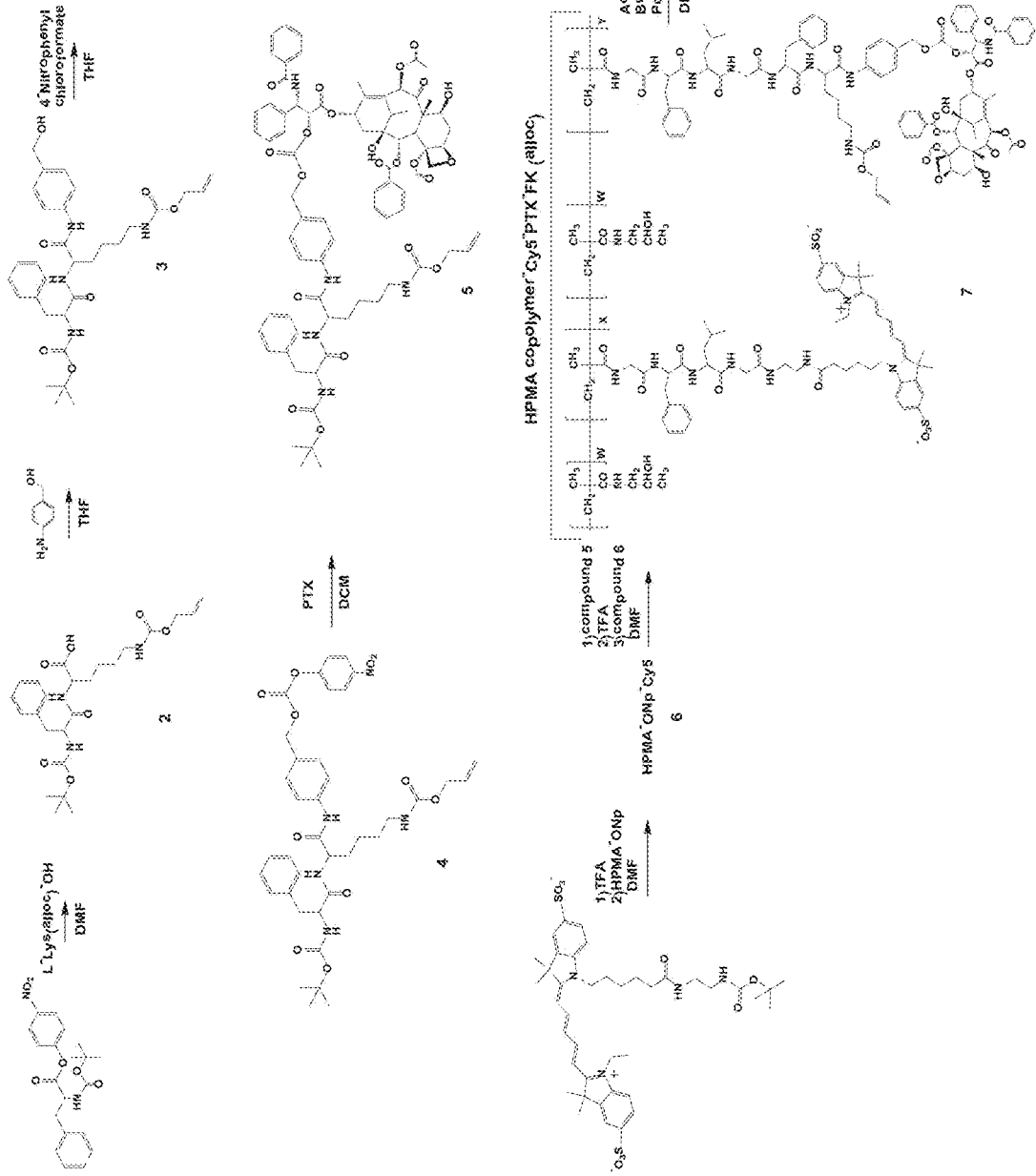

FIG. 6 is a scheme depicting a synthesis of HPMA copolymer-Cy5-PTX-FK conjugate, carried out by conjugating Cy5 to HPMA copolymer, forming a FK-PABC linker and conjugating the linker to PTX, followed by coupling the PTX-Phe-Lys to the HPMA copolymer-Cy5-PTX-FK so as to generate HPMA copolymer-Cy5-PTX-FK; DCM=dichloromethane, DMF=N,N-dimethylformamide, TFA=trifluoroacetic acid.

Figure 7A:
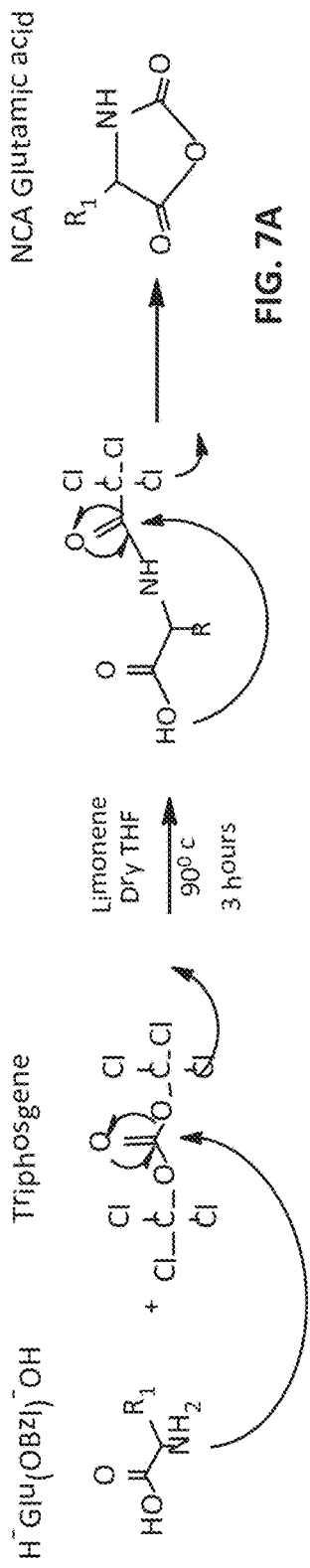
Figure 7B:
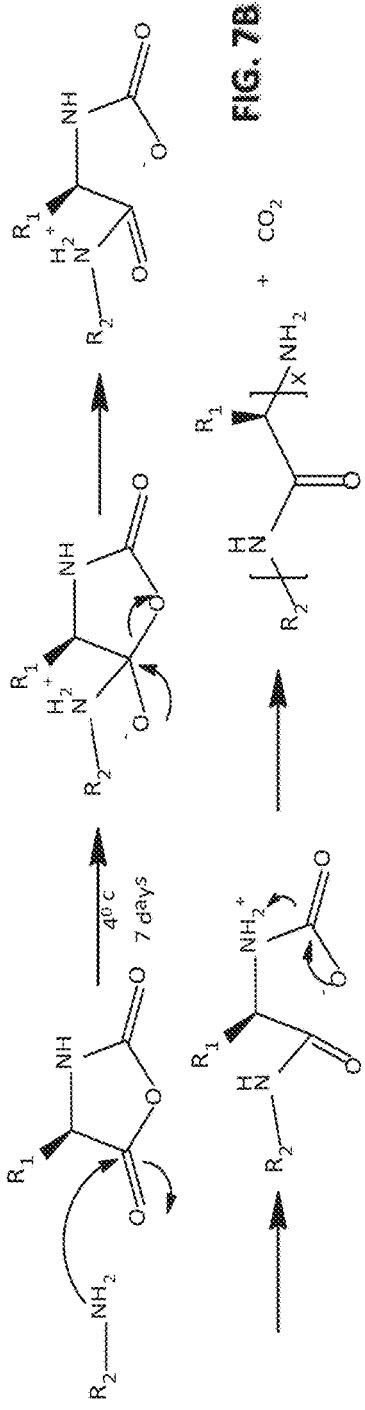
Figure 7C:
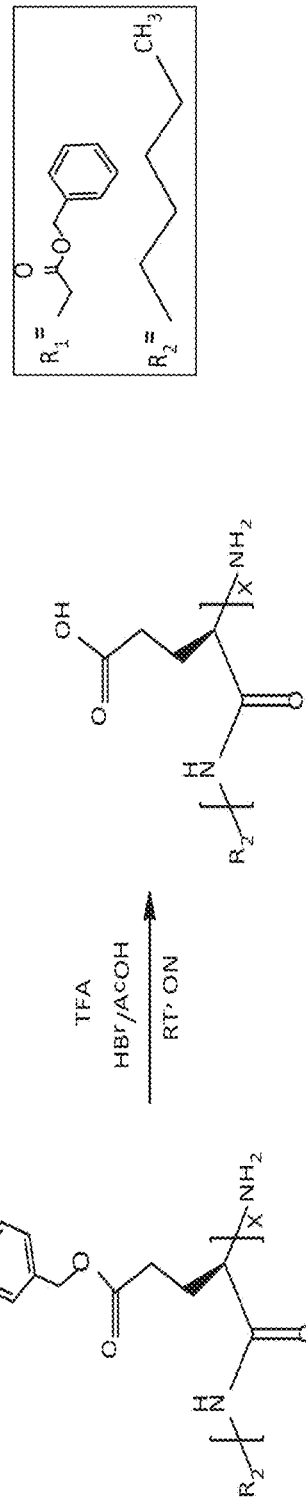
Figure 7D:
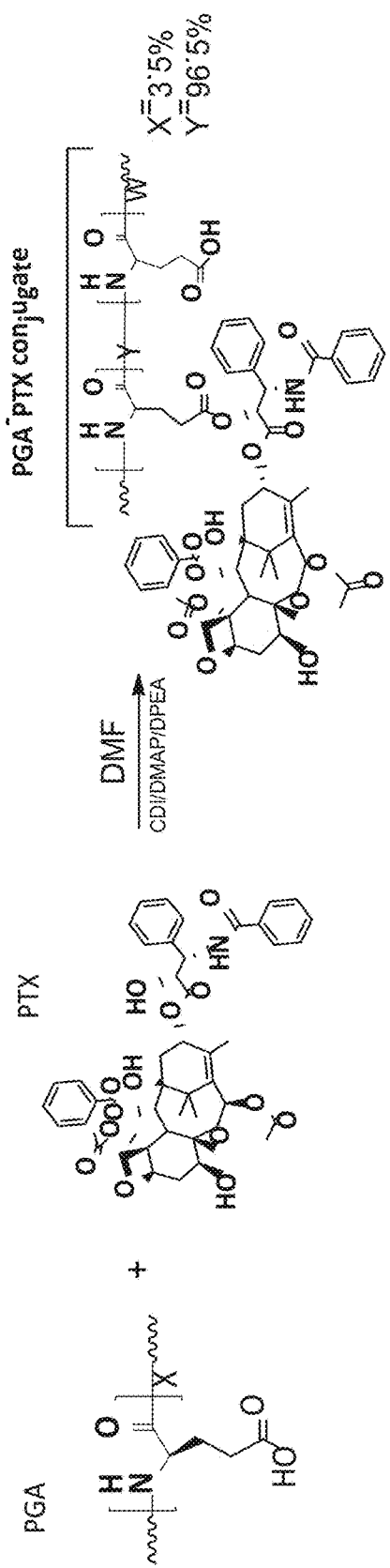

FIGS. 7A-D present a scheme depicting a synthesis of a PGA polymer, carried out by hexylamine-initiated polymerization (FIG. 7B) of the N-carboxyanhydride (NCA) of γ-benzyl-L-glutamate (FIG. 7A), followed by deprotection (FIG. 7C); and of a PGA-PTX conjugate, carried out by activation of PGA with CDI coupling reagent supported by DMAP as a catalyst in basic environment and conjugation of PGA to PTX, by mixing activated polymer with PTX (FIG. 7D).

Figure 8A:
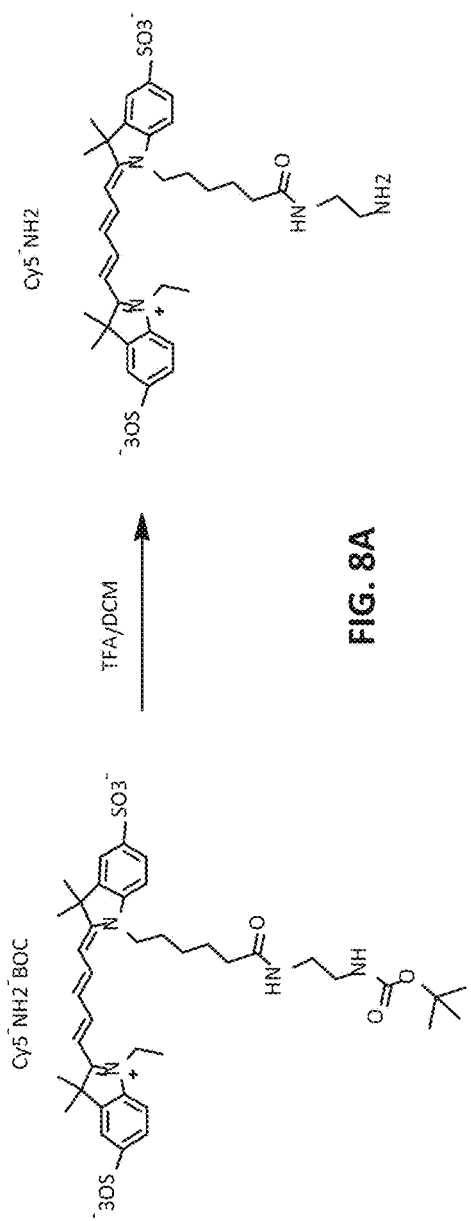
Figure 8B:
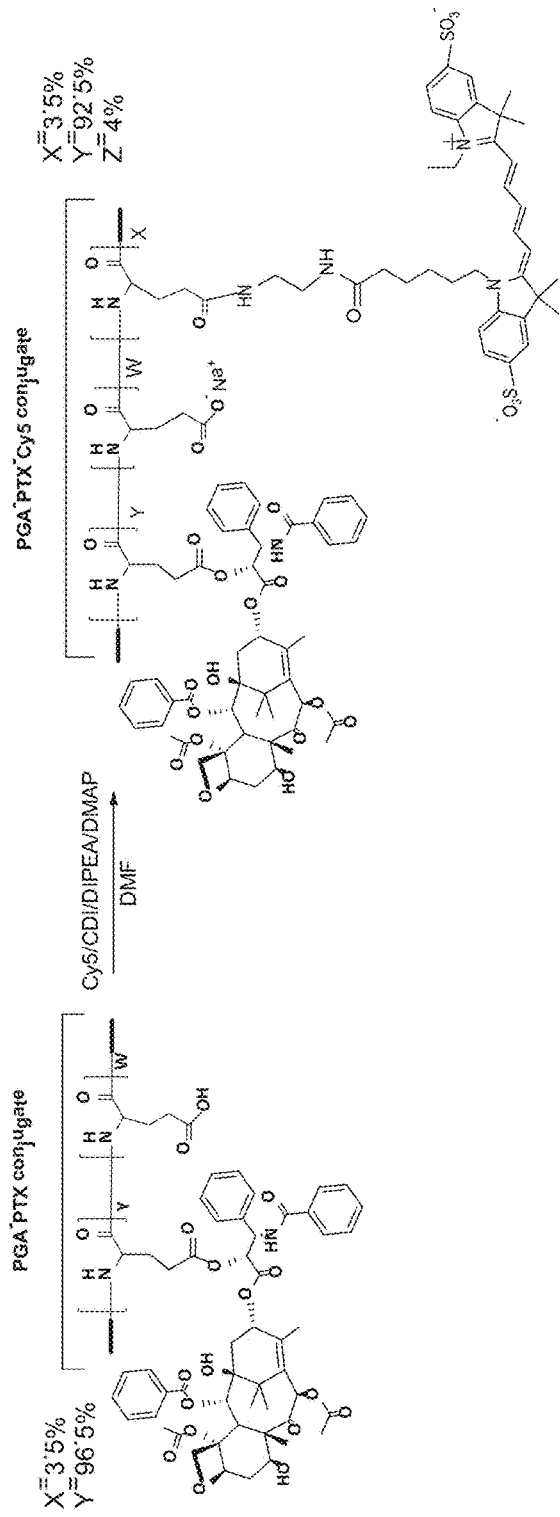

FIGS. 8A-B present schemes depicting a synthesis of PGA-PTX-Cy5 conjugate, carried out by removing the BOC protecting group of a Cy5-$NH_2$—BOC (FIG. 8A); and conjugating the obtained Cy5-$NH_2$ to a PGA-PTX conjugate, by mixing an activated PGA with the Cy5-$NH_2$ (FIG. 8B).

Figure 9A:
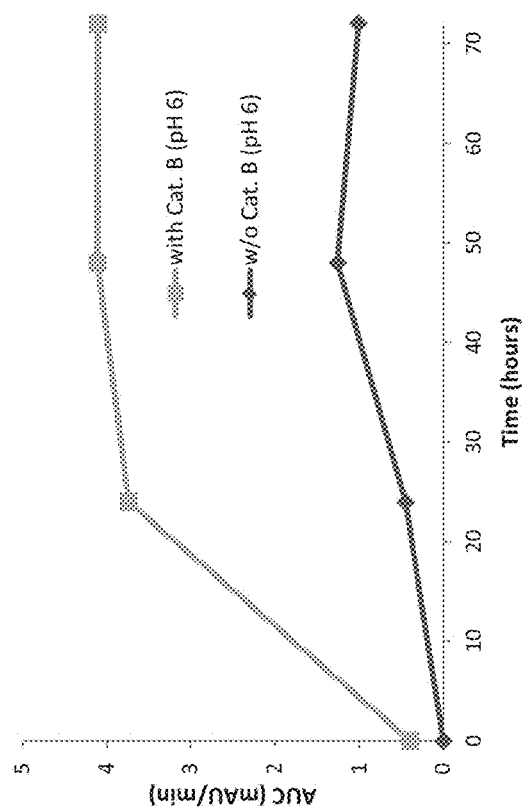
Figure 9B:
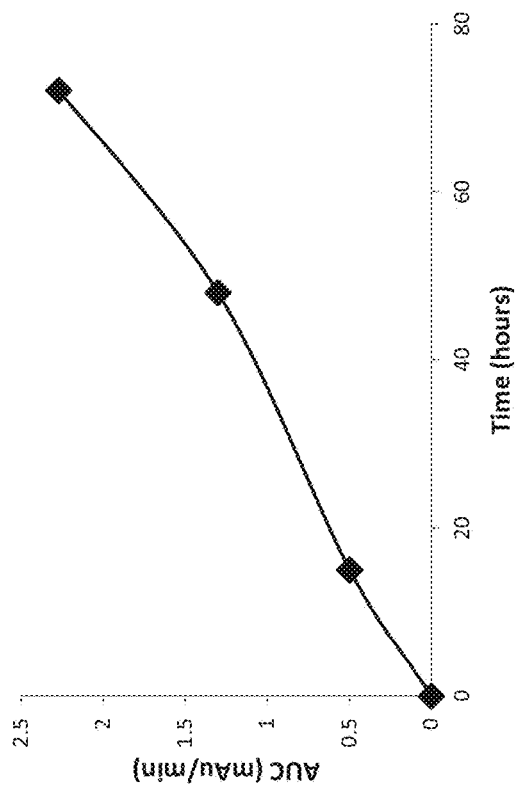

FIGS. 9A-B present graphs showing PTX release kinetics from HPMA copolymer-PTX-FK conjugate upon incubation in the absence (diamonds) or presence (squares) of cathepsin B [1 Unit/ml] in phosphate buffer (pH 6) (FIG. 9A); and PTX release kinetics from HPMA copolymer-PTX conjugate upon incubation in the presence of cathepsin B [1 Unit/ml] (diamonds) (FIG. 9B).

Figure 10B:
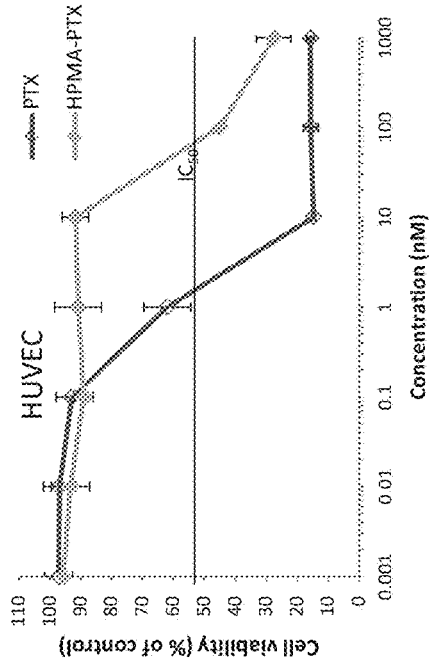
Figure 10D:
Figure 10A:
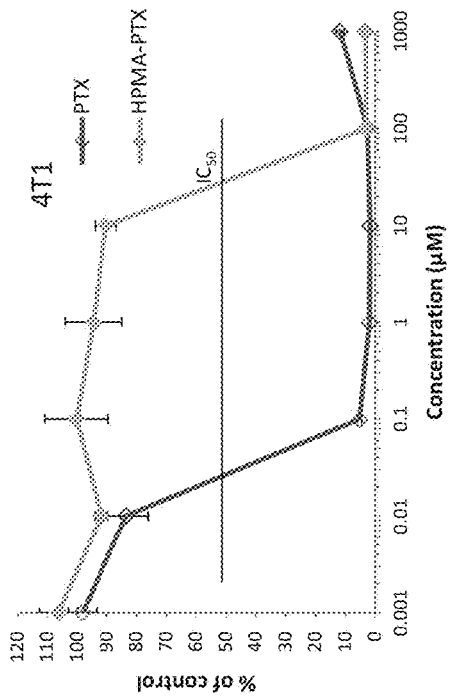
Figure 10C:
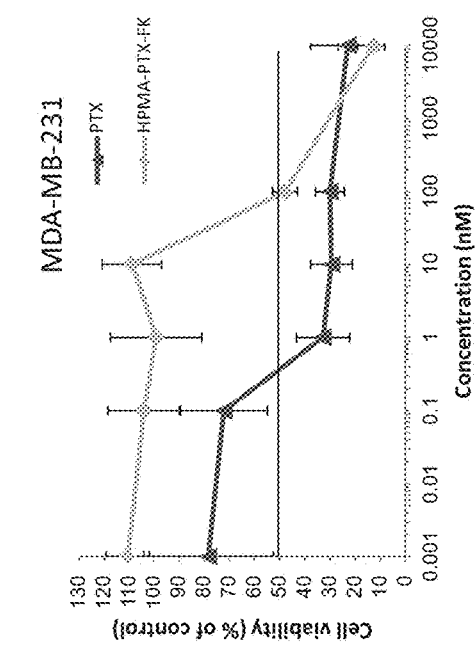

FIGS. 10A-D present graphs showing the anti-proliferative activity of PTX and HPMA copolymer-PTX conjugate in murine 4T1 cells (FIG. 10A) and in HUVEC cells (FIG. 10B), upon incubation for 96 hours; the anti-proliferative activity of HPMA copolymer-PTX-FK conjugate in human MDA-MB-231 mammary adenocarcinoma cells, upon incubation for 72 hours (FIG. 10C), and the IC50 values obtained in these assays (FIG. 10D).

FIGS. 11A-C present comparative plots showing the self-quenching capability of an HPMA copolymer-Cy5 conjugate (3.8 mol % loading) (blank diamonds) and of free Cy5 (squares) (FIG. 11A); Comparative plots showing the changes in fluorescence intensity ($\lambda_{Ex}$=600 nm, $\lambda_{Em}$=670 nm) emitted upon incubation of HPMA copolymer-Cy5 conjugate [0.01 mM] in the presence (blank diamonds) of cathepsin B [1 Units/ml] in Phosphate buffer (pH 6) and in the absence of cathepsin B in PBS (pH 7.4) (squares), with data acquired throughout 160 hours following enzyme addition at 37° C. (FIG. 11B); and a bar graph showing the in vitro degradation of HPMA copolymer-Cy5 (gray bars) in cultured MDA-MB-231 cells, compared to non-treated cells (white bars), as measured by activation of a fluorescence signal (The data represent mean SD (n=3); *p<0.05, **p<0.01) (FIG. 11C).

Figure 12A:
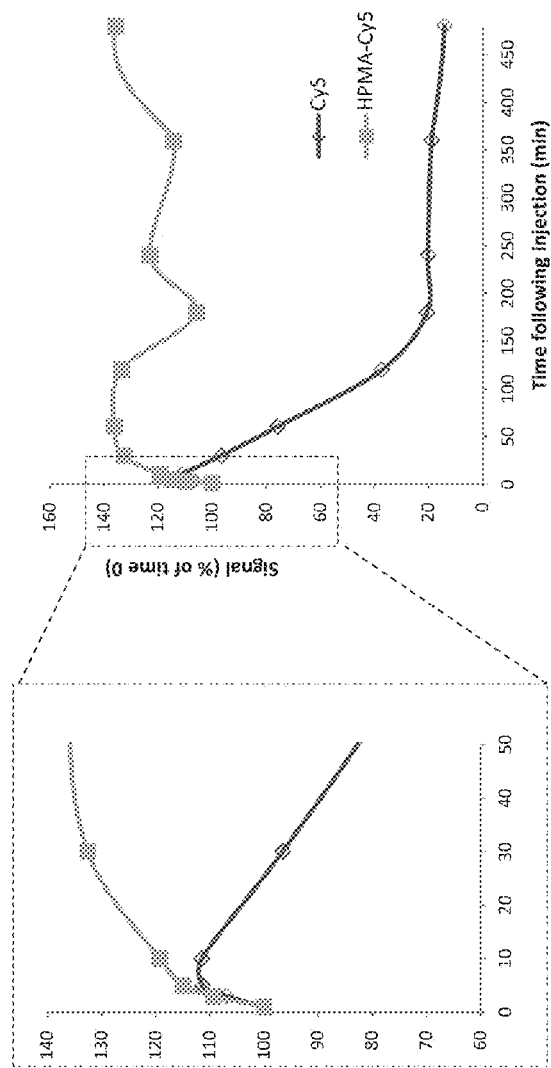
Figure 12B:
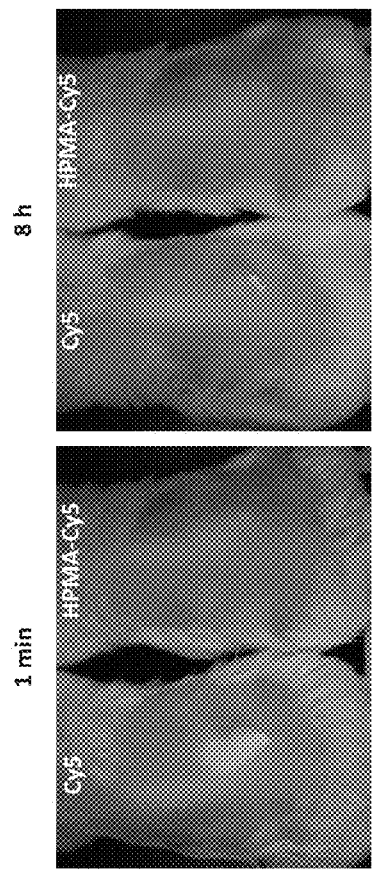

FIGS. 12A-B present graphs showing quantification of the fluorescence signal following intra-tumoral injection of free Cy5 [0.1 mM; 30 µl] (blank diamonds) and equivalent dose of HPMA copolymer-Cy5 conjugate (squares) into subcutaneous 4T1 mammary adenocarcinoma (FIG. 12A) and images showing that the fluorescence signal of HPMA copolymer-Cy5 conjugate is maintained 8 hours following injection, while free Cy5 exhibits 80% bleach already within 3 hours [Images were acquired and quantified using CRI Maestro™ imaging system; Filter set: excitation—635 nm, emission cutoff—675 nm] (FIG. 12B).

FIGS. 13A-C present an image (FIG. 13A) and a bar graph (FIG. 13B) showing the fluorescent signal and tumor/background ratio of HPMA copolymer-Cy5 conjugate in a 4T1 tumor, upon administering the conjugate (10 µM; 200 µl) via the tail vein of mice, as monitored using CRI Maestro™ imaging system; and a bar graph (FIG. 13C) showing the Cy5-fluorescent spectrum (composed images of unmixed multispectral cubes) in resected organs of mice bearing 4T1 tumors treated with HPMA copolymer-SQ-Cy5 conjugate (10 µM; 200 µl), demonstrating greater intensity of Cy5-fluorescence spectrum in tumor tissue, liver and kidneys compared with other organs.

Figure 14A:
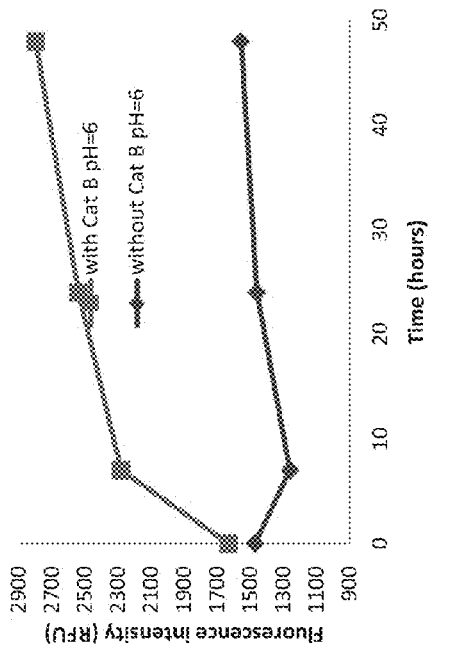
Figure 14B:
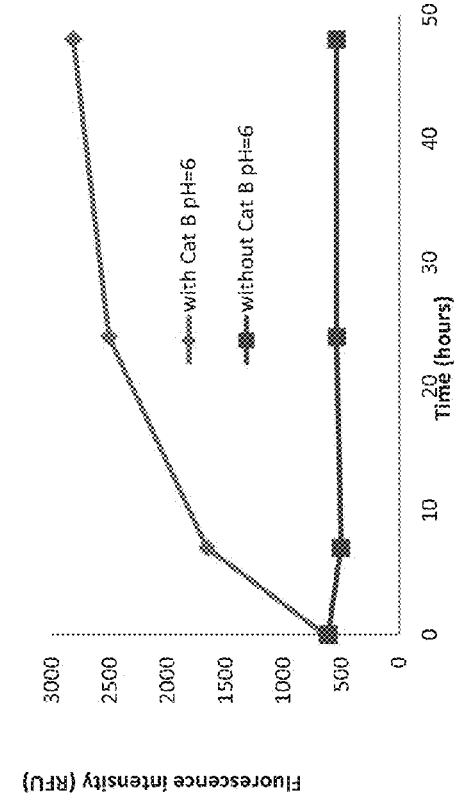
Figure 14C:
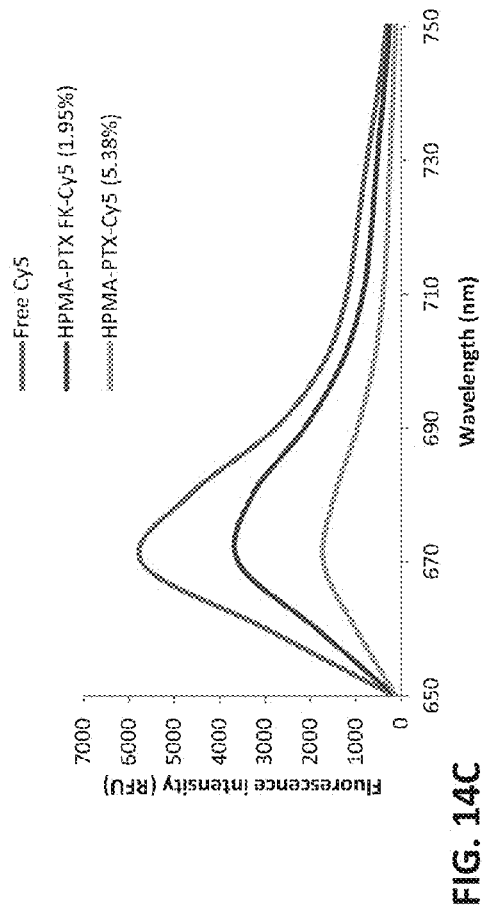

FIGS. 14A-C present graphs showing the emitted fluorescence intensity ($\lambda_{Ex}$=650 nm) by HPMA copolymer-SQ-Cy5-PTX conjugate (FIG. 14A) and HPMA copolymer-SQ-Cy5-PTX-FK conjugate (FIG. 14B) as measured using SpectraMax® M5$^e$ plate reader, upon incubation of the conjugates [0.01 mM] in the presence or absence of cathepsin B [1 Units/ml] in Phosphate buffer (pH 6); Data was acquired throughout 48 hours following enzyme addition at 37° C.; and comparative plots showing the emission of HPMA-PTX-Cy5 conjugate loaded with 5.38 mol % Cy5 and HPMA-PTX-FK-Cy5 loaded with 1.95 mol % Cy5 compared to free Cy5 emission ($\lambda_{ex}$=650 nm, $\lambda_{em}$=670 nm) with a similar equivalent concentration of Cy5 (13-19 µM) (FIG. 14C).

Figure 15A:
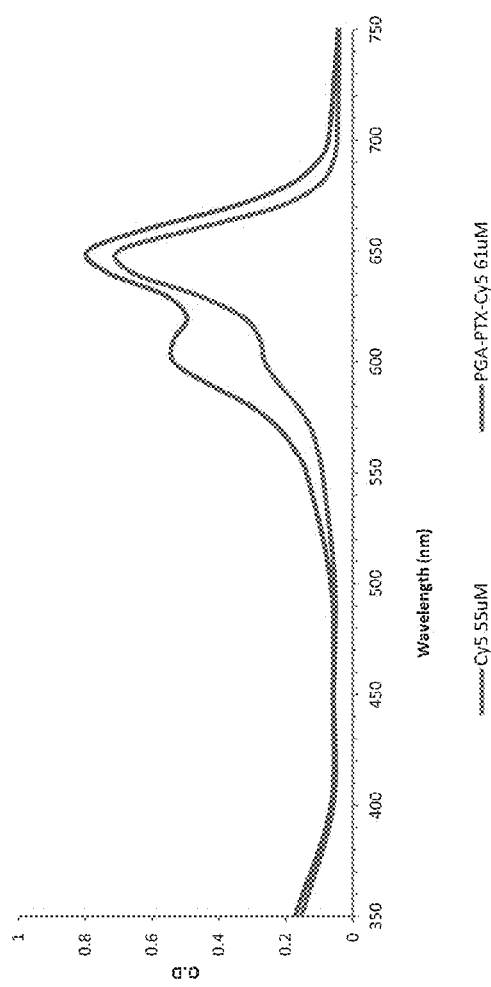
Figure 15B:
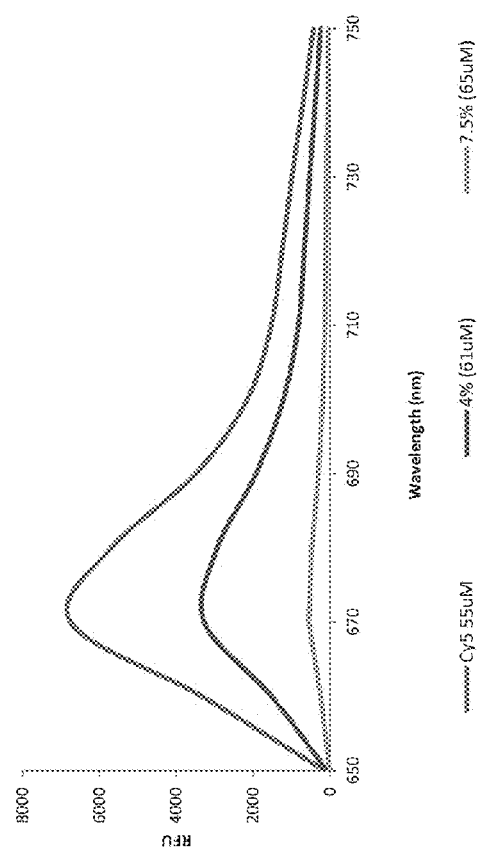
Figure 15C:
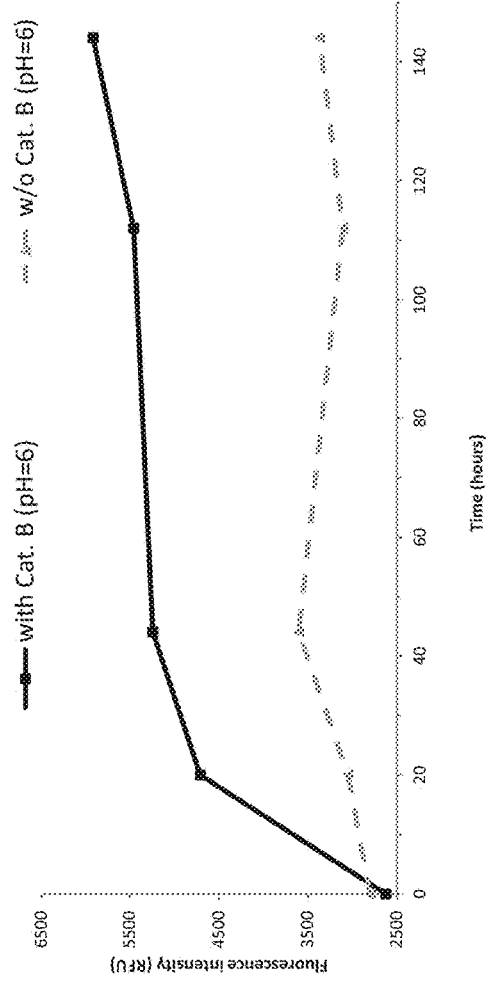
Figure 15D:
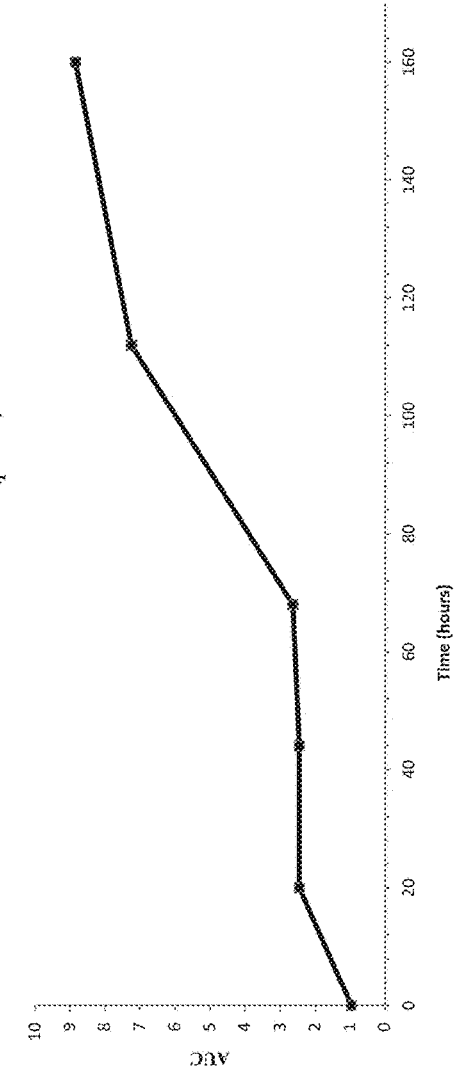

FIGS. 15A-D present comparative plots showing: the absorption spectrum of PGA-PTX-Cy5 (red) compared to a free Cy5 (blue) (FIG. 15A); the emission spectrum ($\lambda_{ex}$=650 nm, $\lambda_{em}$=670 nm) of PGA-PTX-Cy5 conjugate loaded with 4 mol % Cy5 (red), PGA-PTX-Cy5 loaded with 7.5 mol % Cy5 (green) and of free Cy5 (blue) (FIG. 15B); the emitted fluorescence ($\lambda$ex=650 nm, $\lambda$em=670 nm) following enzymatic release of Cy5 from the PGA-PTX-SQ-Cy5 conjugate upon incubation in the presence (black) and in the absence (dashed gray) of cathepsin B enzyme [1 Units/ml] as a function of time (FIG. 15C); and the PTX release kinetics from PGA-PTX-Cy5 conjugate upon incubation in the presence of cathepsin B enzyme [1 Units/ml] as a function of time (FIG. 15D).

FIGS. 16A-D present comparative plots showing the anti-proliferative activity of free PTX, PGA-PTX and PGA-PTX-Cy5 conjugate, free PTX, PGA-PTX and PGA-PTX-Cy5 in human MDA-MB-231 mammary adenocarcinoma cell line (FIG. 16A), murine 4T1 cell line (FIG. 16B) and human WM239A melanoma cell line (FIG. 16C), upon incubating the cells with the tested agent for 72 hours; and the IC50 values obtained in these assays (FIG. 16D) [Data represents mean±SD. The X-axis is presented at a logarithmic scale].

Figure 17:
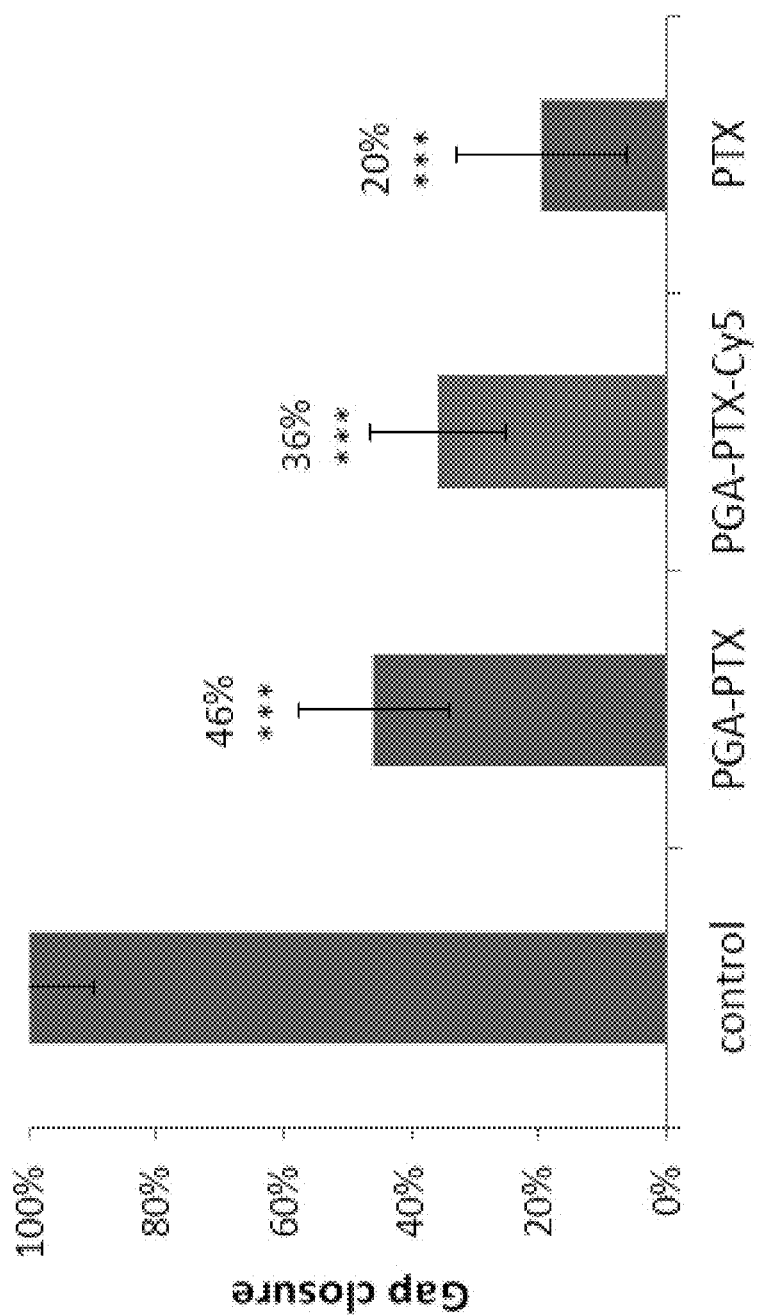

FIG. 17 presents a bar graph demonstrating the inhibition of the migration of HUVECs by a PGA-PTX-Cy5 conjugate, compared to free PTX, PGA-PTX, PGA-PTX-Cy5 and control (non-treated HUVECs). Migration was normalized to percent migration with 100% representing migration control [Data represents mean±SD, (*** p<0.005)].

Figure 18A:
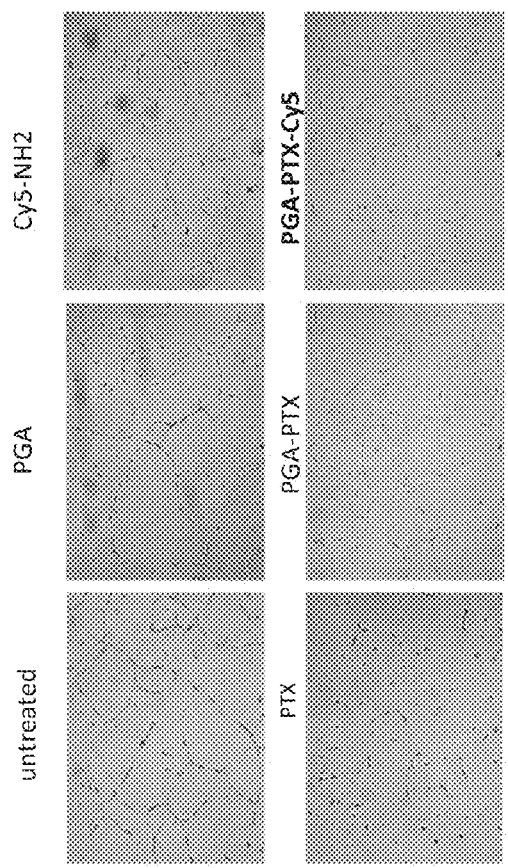
Figure 18B:
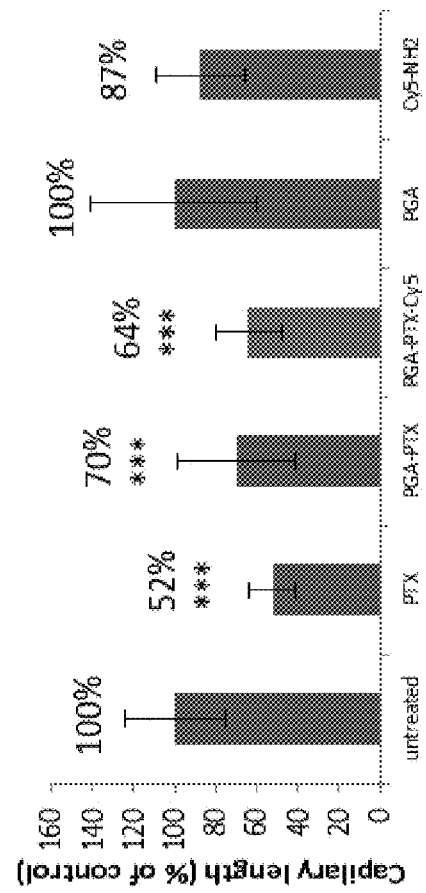

FIGS. 18A-B present representative images showing the effect of free PTX, PGA-PTX, PGA-PTX-Cy5, PGA and Cy5-amine, compared to control (untreated), on capillary-like tube structures formation of HUVEC, following incubation (FIG. 18A); and a bar graph showing a quantitative analysis of the mean length of capillary tubes following incubation (Data represents mean displayed as % of control±SD; * p<0.05;  p<0.01; * p<0.005).

Figure 19A:
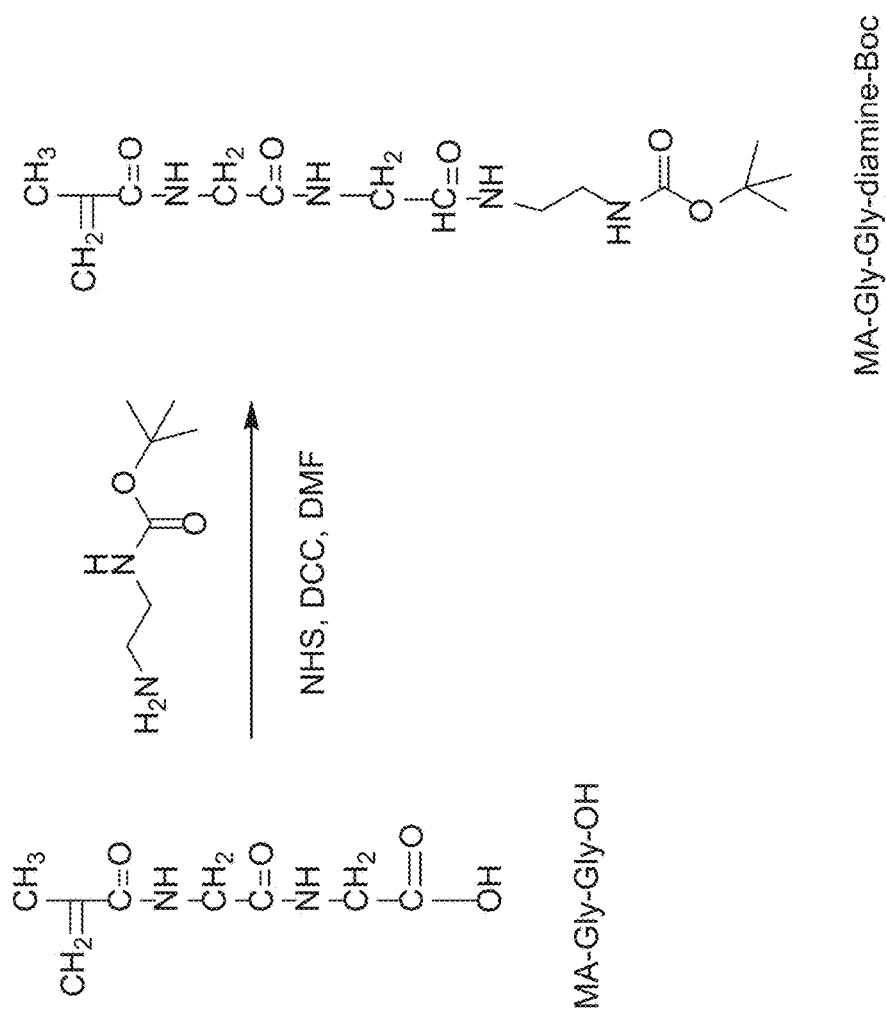
Figure 19B:
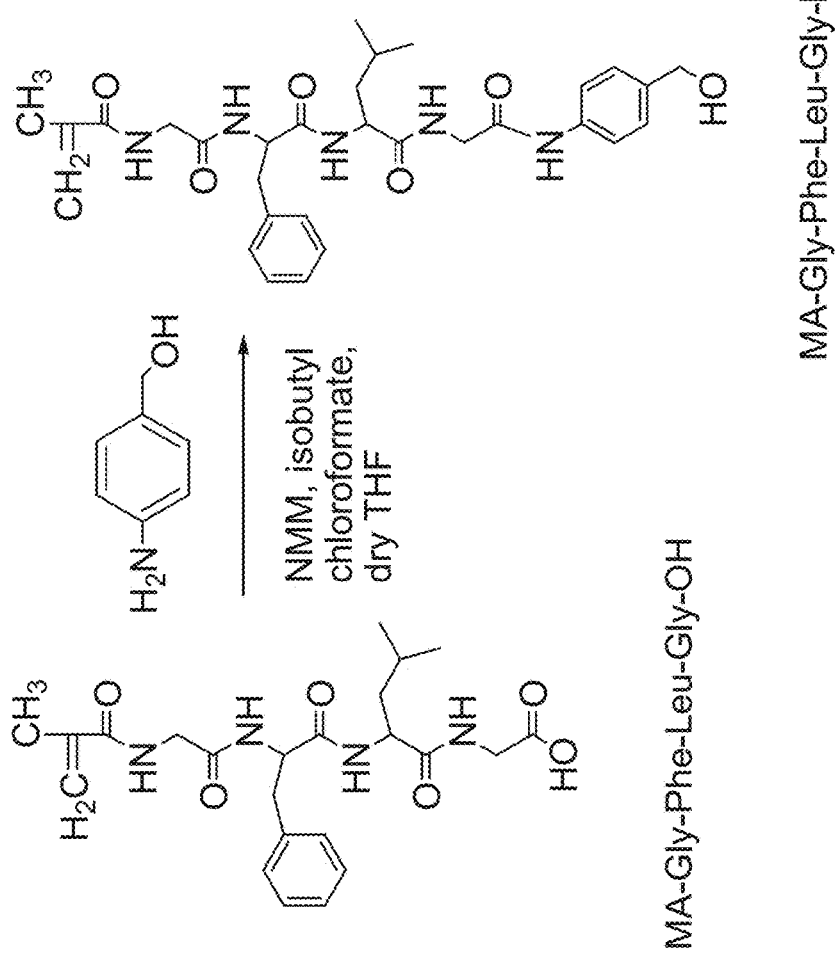

FIGS. 19A-B present schemes depicting the Chemical syntheses of MA-Gly-Gly-diamine-Boc monomer (FIG. 19A) and MA-Gly-Phe-Leu-Gly-PABA monomer (FIG. 19B); NHS=N-hydroxy-succinimide, DCC=dicyclohexyl carbodiimide, DMF=N,N-dimethylformamide, NMM=N-methylmorpholine, THF=tetrahydrofuran.

Figure 20:
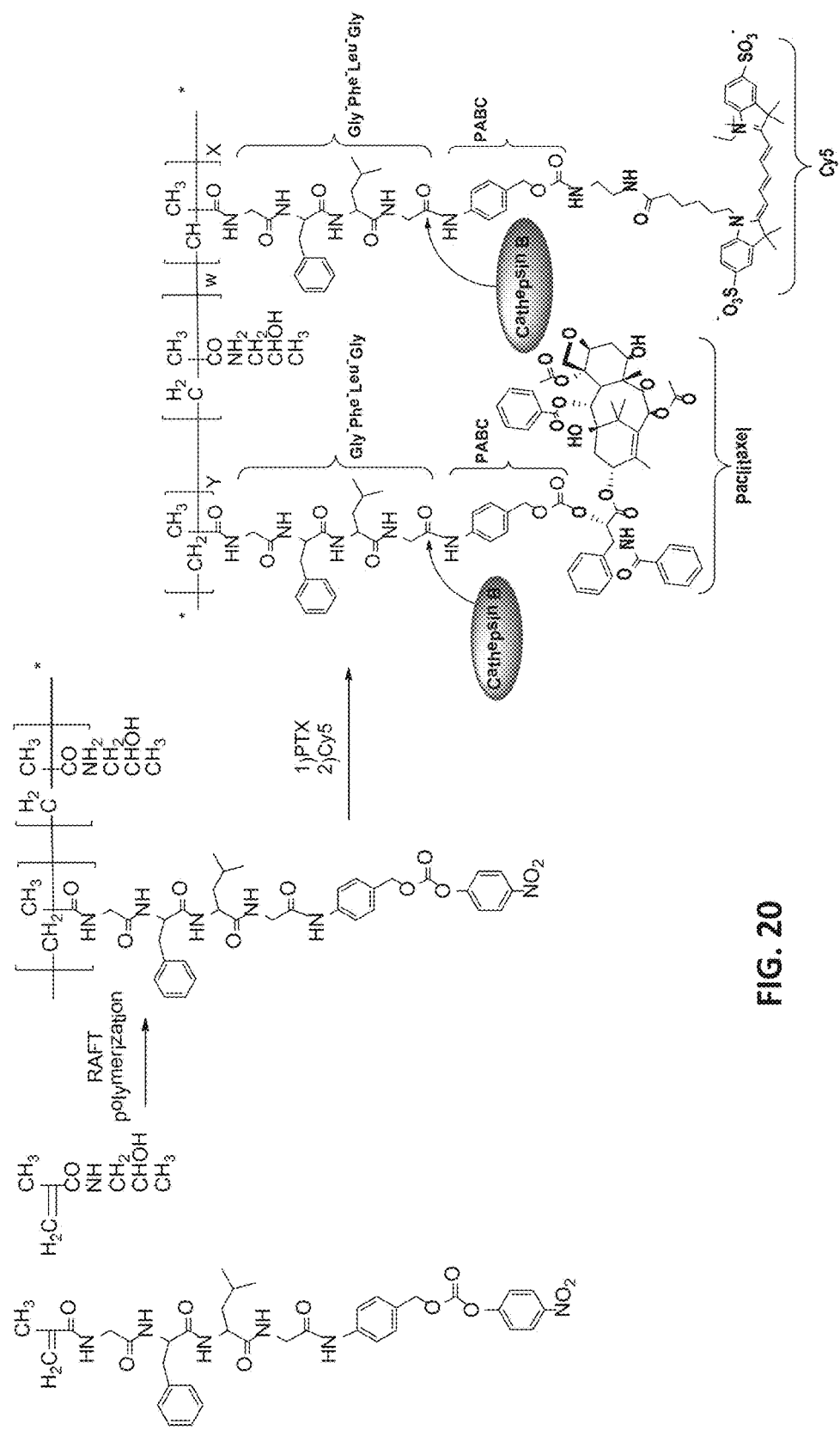

FIG. 20 is a scheme depicting a two-step synthesis of HPMA copolymer-Gly-Phe-Leu-Gly-PABC-Cy5-PTX, carried out by RAFT polymerization of the copolymer precursor, followed by coupling with PTX, as an exemplary drug and Cy5, as an exemplary fluorogenic moiety.

Figure 21:
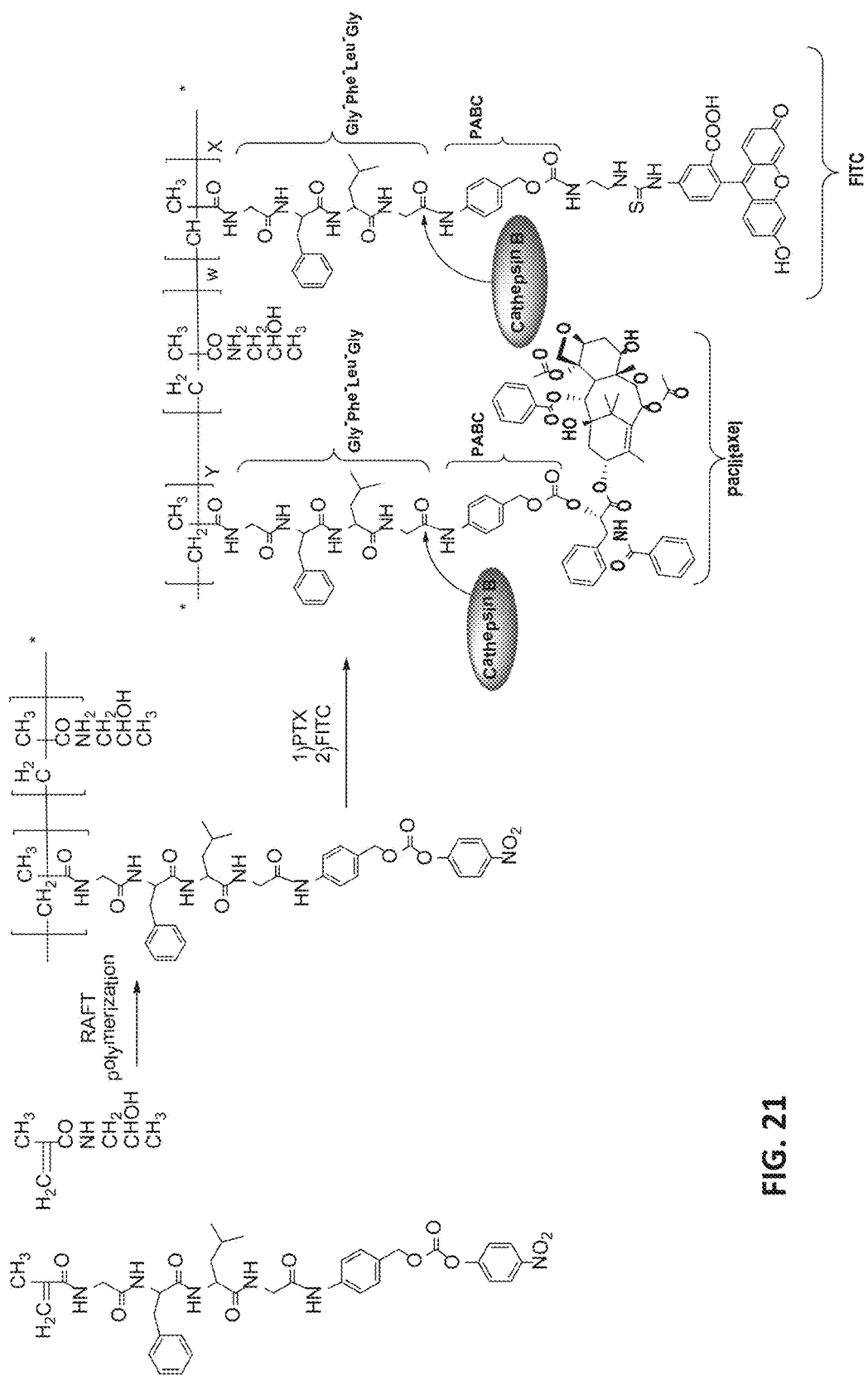

FIG. 21 is a scheme depicting a two-step synthesis of HPMA copolymer-Gly-Phe-Leu-Gly-PABC-FITC-PTX, carried out by RAFT polymerization of the copolymer precursor, followed by coupling with PTX, as an exemplary drug, and FITC, as an exemplary fluorescent moiety.

Figure 22A:
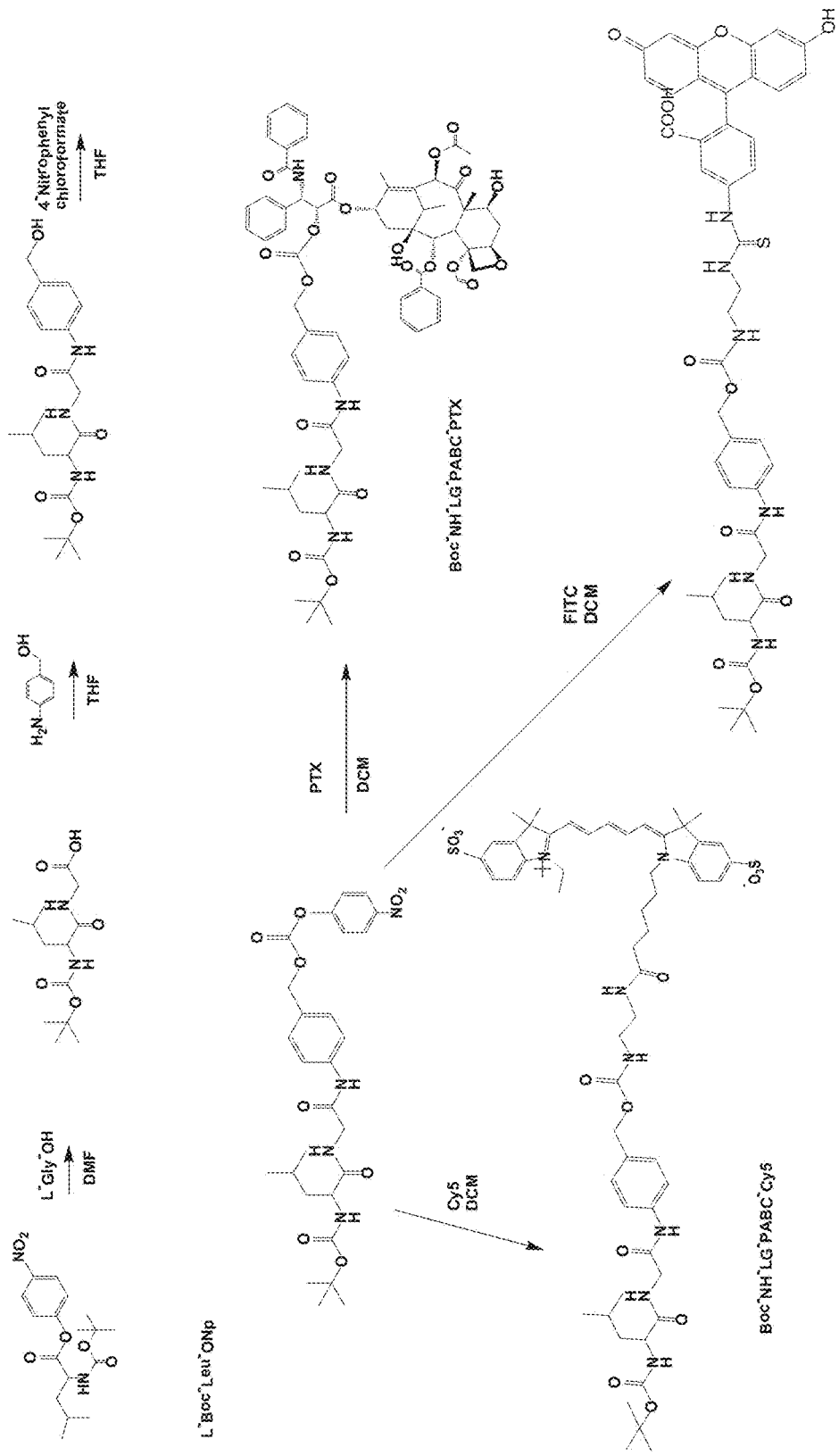
Figure 22B:
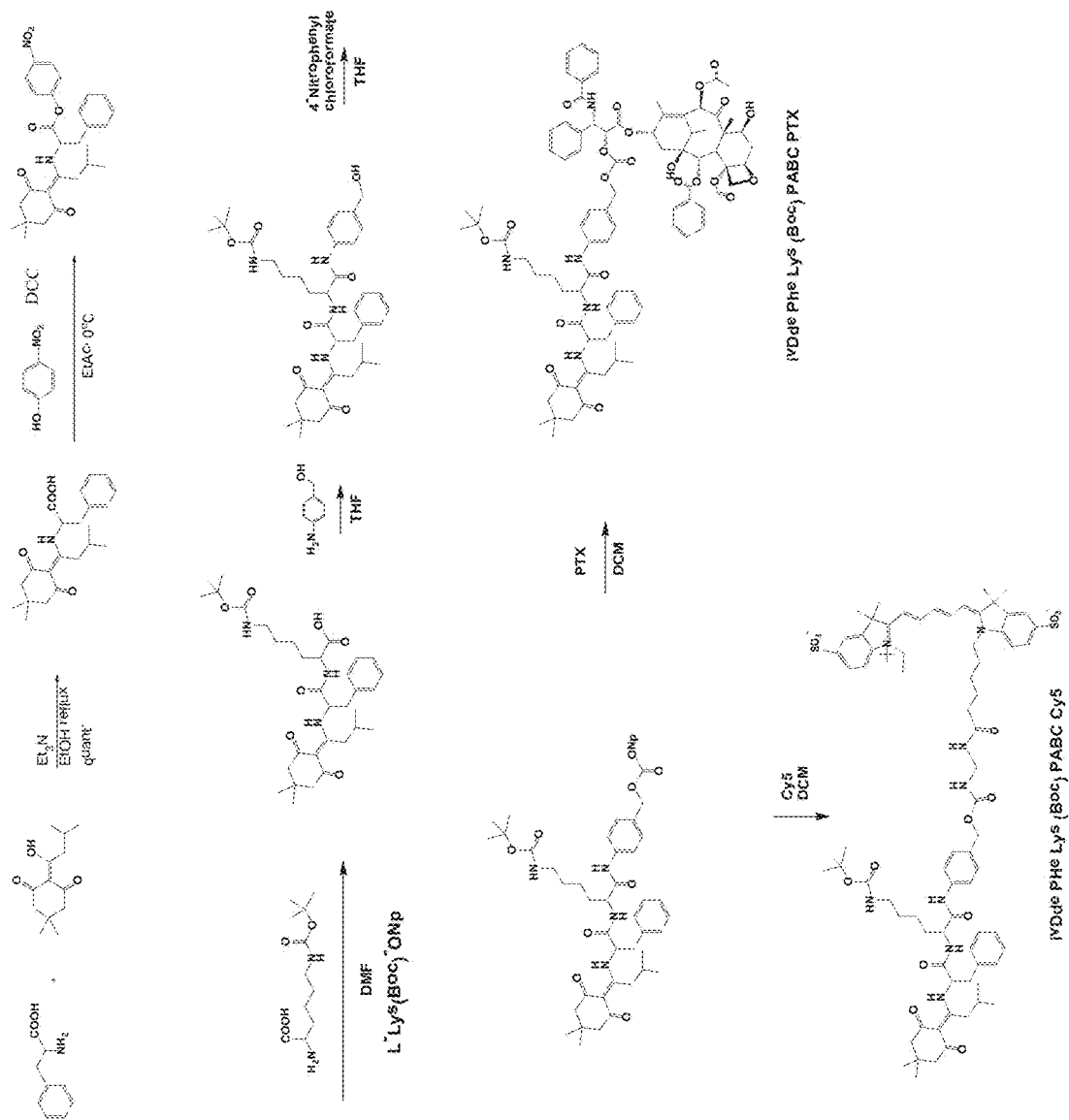

FIGS. 22A-B present schemes depicting the syntheses of exemplary drug and dye dipeptide-PABC moieties: Boc-NH-LG-PABC-PTX, Boc-NH-LG-PABC-Cy5 and Boc-NH-LG-PABC-FITC (FIG. 22A), and ivDde-NH-FK-PABC-PTX and ivDde-NH-FK-PABC-Cy5 (FIG. 22B), useful for further conjugation to HPMA copolymer-dipeptide-ONp (Gly-Gly-ONp).

Figure 23:
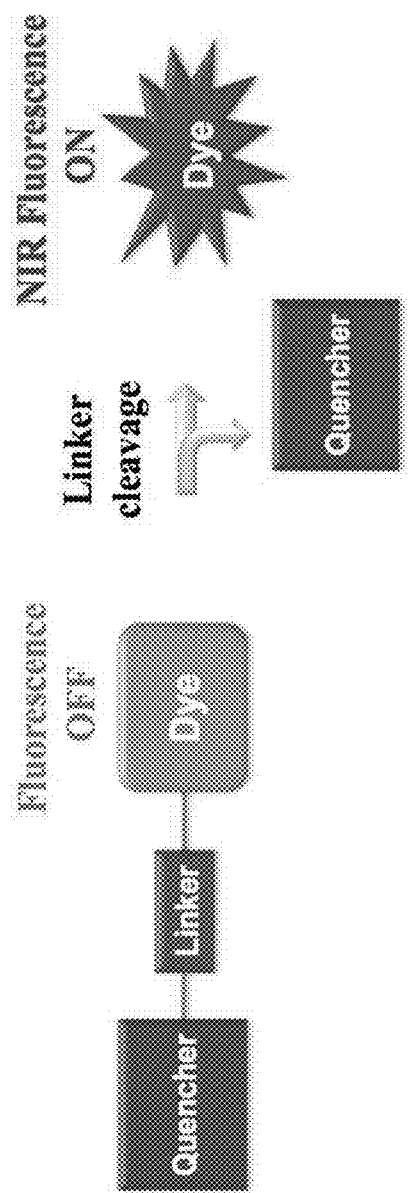

FIG. 23 presents an illustration of the general design and mode of action of a FRET-based turn-ON system.

Figure 24:
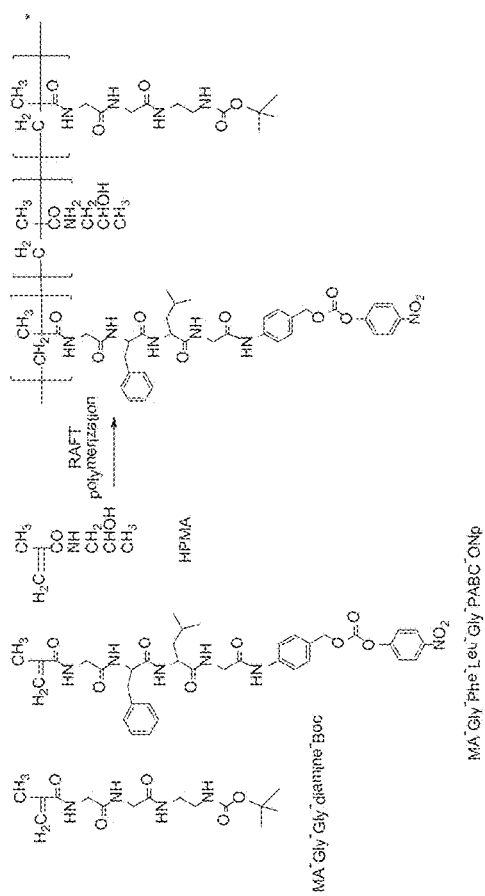
Figure 24:
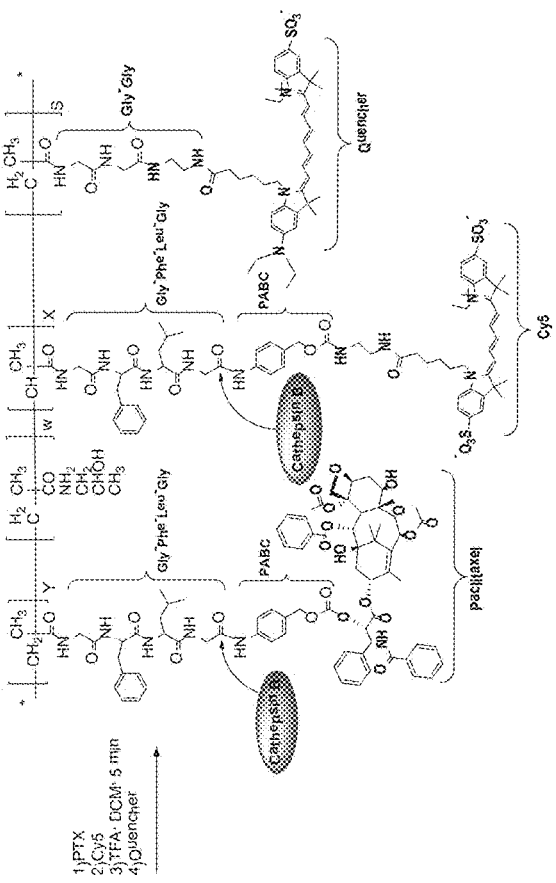

FIG. 24 is a scheme depicting a two-step synthesis of HPMA copolymer-Gly-Phe-Leu-Gly-PABC-Cy5-Quencher-PTX, carried out by RAFT polymerization of the copolymer precursor, followed by coupling with the drug (PTX), dye (Cy5) and finally the quencher.

Figure 25:
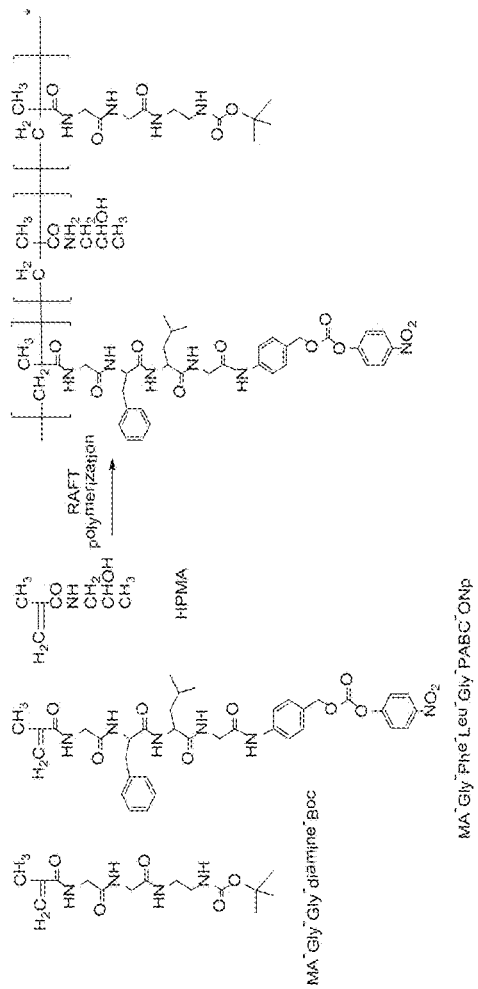
Figure 25:
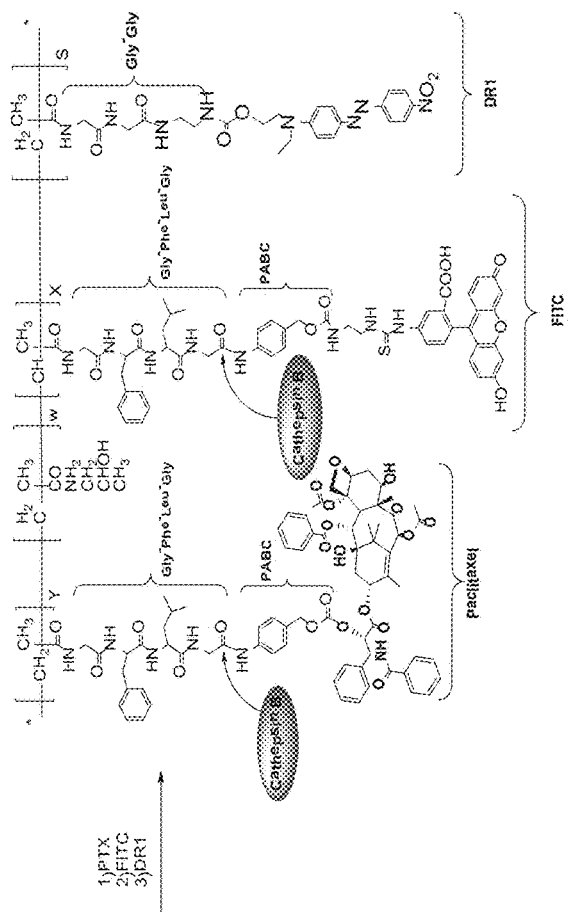

FIG. 25 is a scheme depicting a two-step synthesis of HPMA copolymer-Gly-Phe-Leu-Gly-PABC-FITC-DR1-PTX, carried out by RAFT polymerization of the copolymer precursor, followed by coupling with the drug (PTX), dye (FITC) and finally the quencher, DR1.

Figure 26:
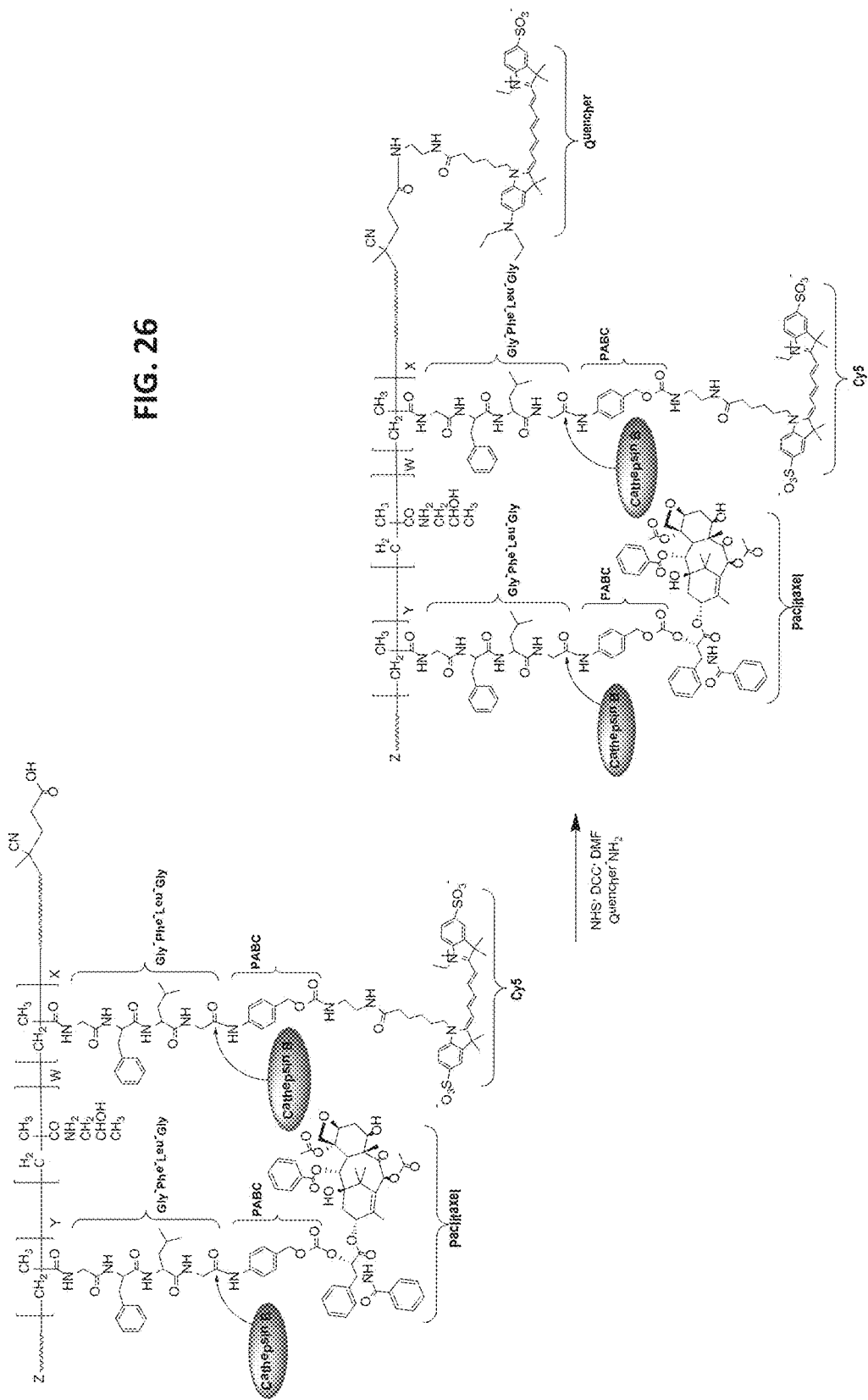

FIG. 26 is a scheme depicting a FRET-based theranostic system in which a quencher-amine is coupled to a COOH end-functionalized HPMA copolymer-PTX-Cy5 conjugate, providing a conjugate with one quencher molecule per polymeric chain.

Figure 27:
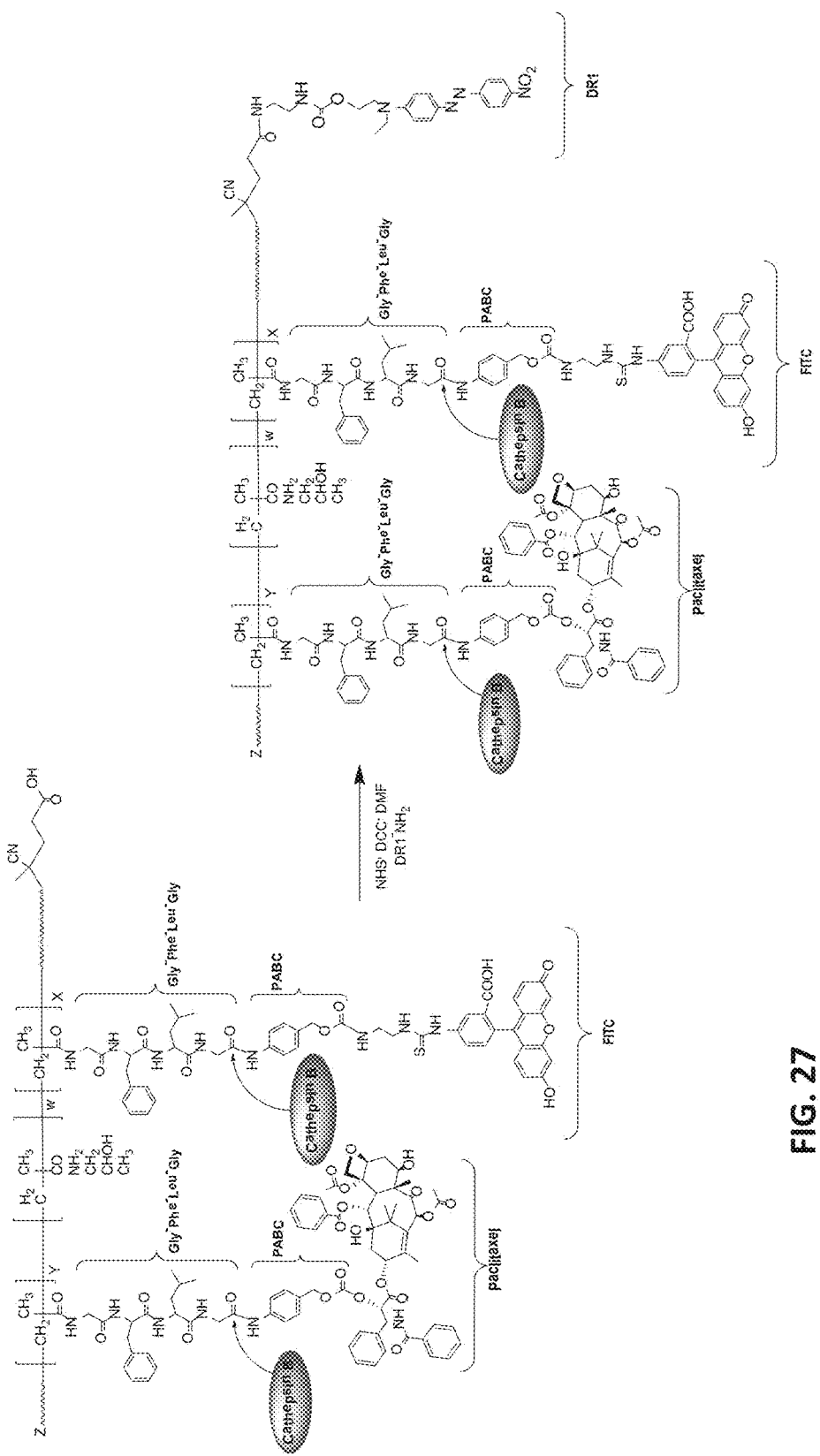

FIG. 27 is a scheme depicting a FRET-based theranostic system in which a DR1-amine is coupled to a COOH end-functionalized HPMA copolymer-PTX-FITC conjugate, providing a conjugate with one quencher molecule per polymeric chain.

Figure 28:
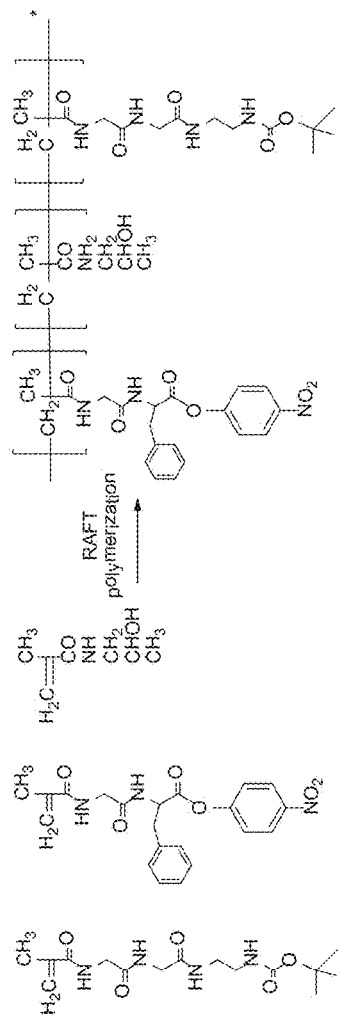
Figure 28:
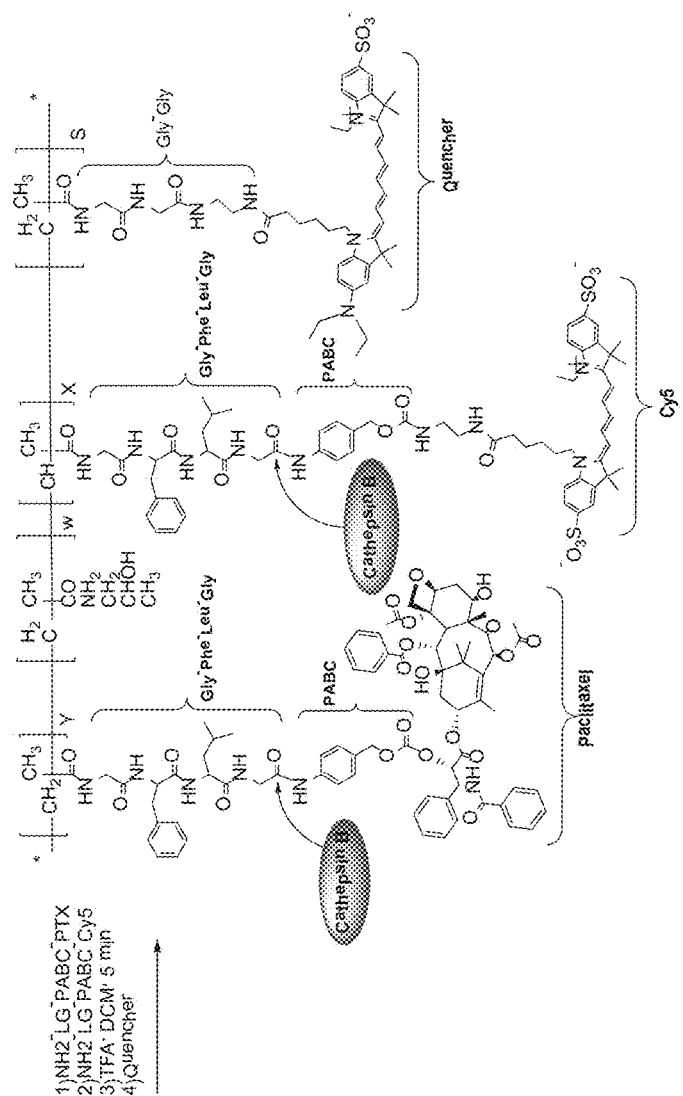

FIG. 28 is a scheme depicting the synthesis of a HPMA copolymer-Gly-Phe-Leu-Gly-PABC-PTX-Cy5-quencher conjugate by RAFT polymerization of a copolymer precursor HPMA-Gly-Phe-ONp/Gly-Gly-diamine-Boc, followed by coupling to the precursor amine-Leu-Gly-PABC-PTX, amine-Leu-Gly-PABC-Cy5 and quencher-COOH.

Figure 29:
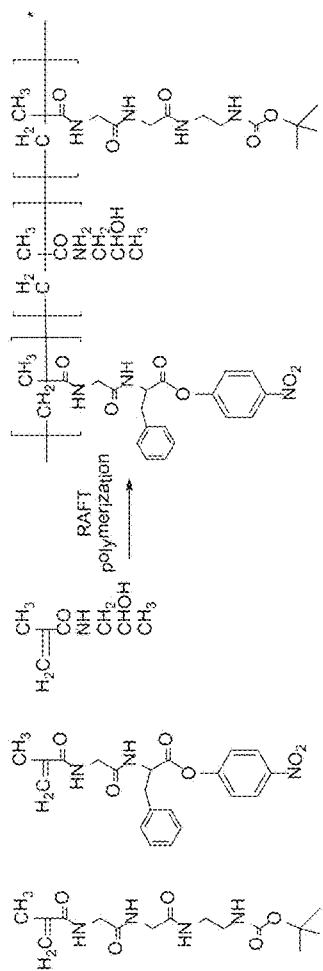
Figure 29:
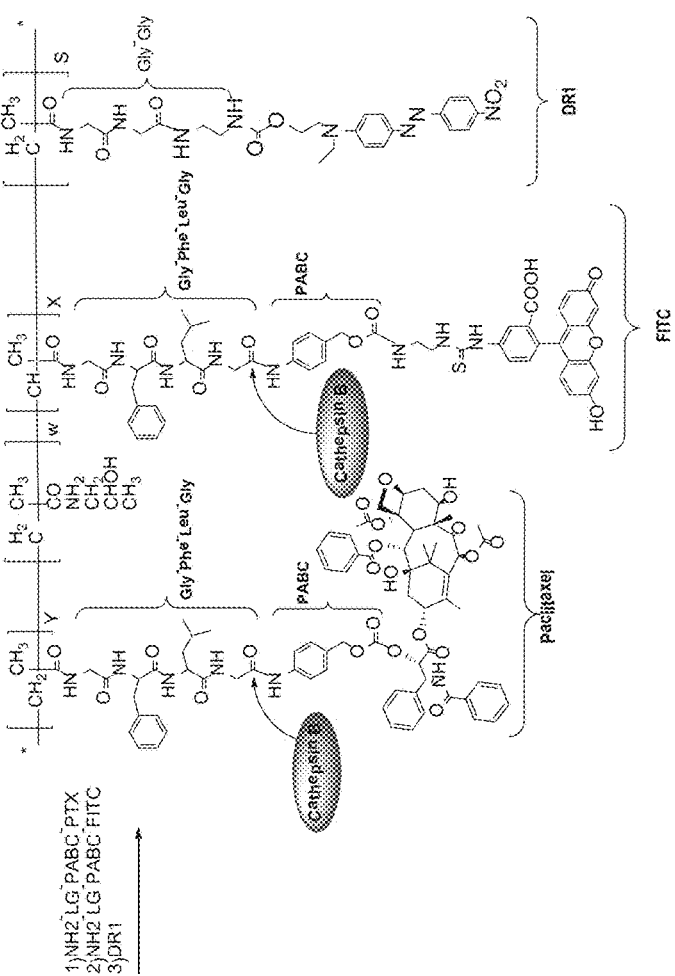

FIG. 29 is a scheme depicting the synthesis of a HPMA copolymer-Gly-Phe-Leu-Gly-PABC-PTX-FITC-DR1 conjugate by RAFT polymerization of a copolymer precursor HPMA-Gly-Phe-ONp/Gly-Gly-diamine-Boc, followed by coupling to the precursor amine-Leu-Gly-PABC-PTX, amine-Leu-Gly-PABC-FITC and DR1-amine.

Figure 30:
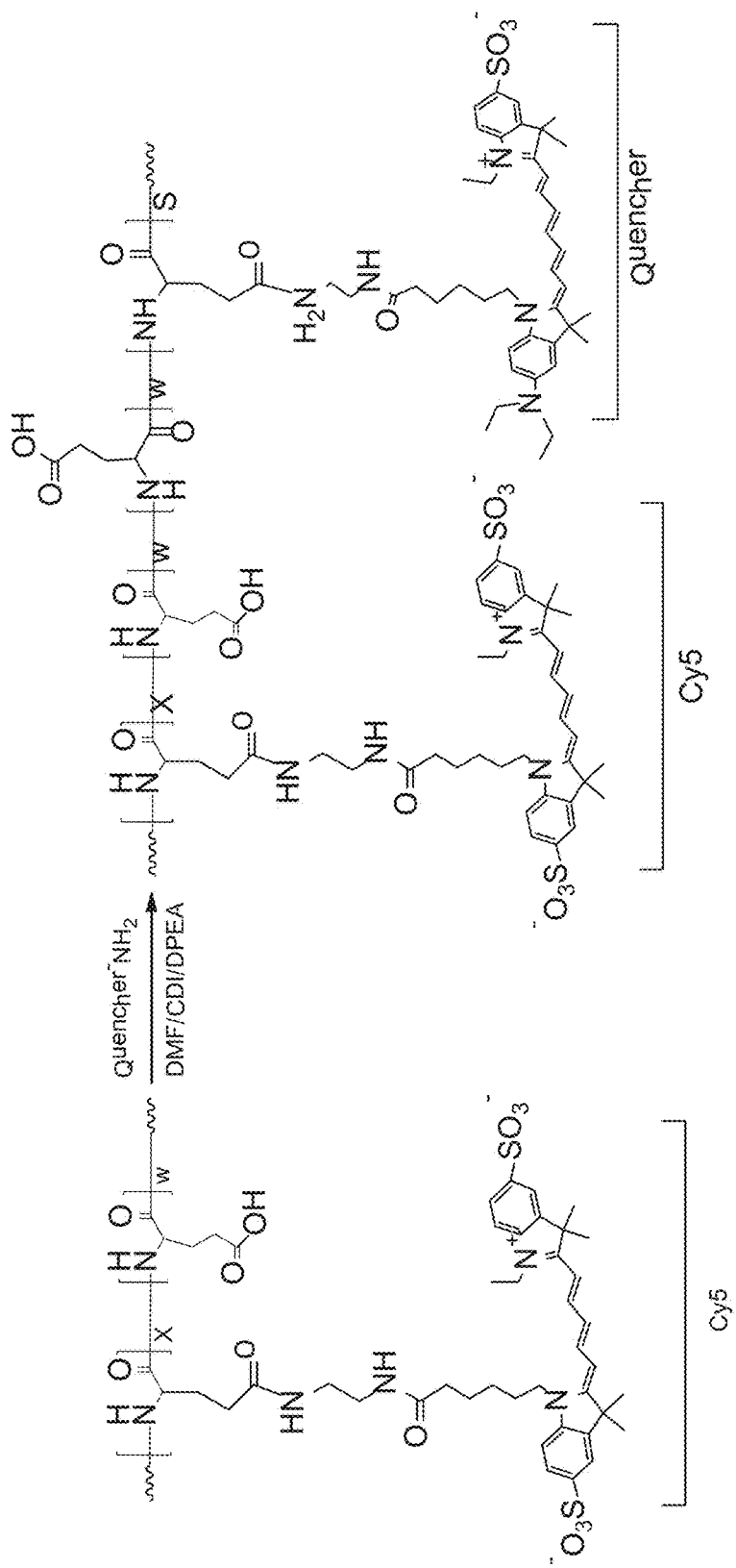

FIG. 30 is a scheme depicting the synthesis of a FRET-based PGA-Cy5-Quencher conjugate. Coupling of PGA to the Cy5-NH$_2$ is carried out by mixing a CDI activated polymer and the fluorophore, followed by the coupling of PGA-Cy5 conjugate to a deprotected Quencher-NH$_2$.

Figure 31A:
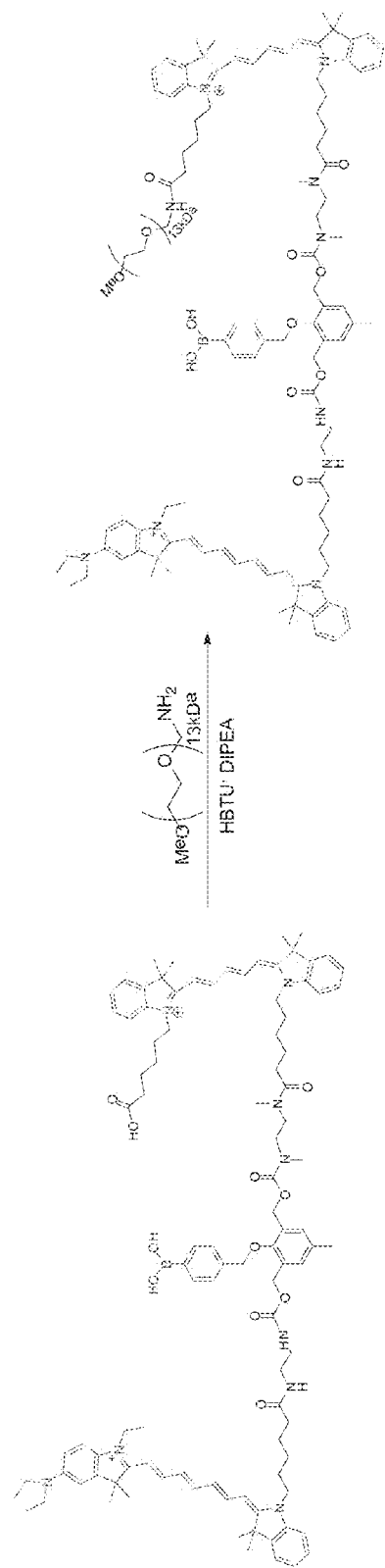
Figure 31B:
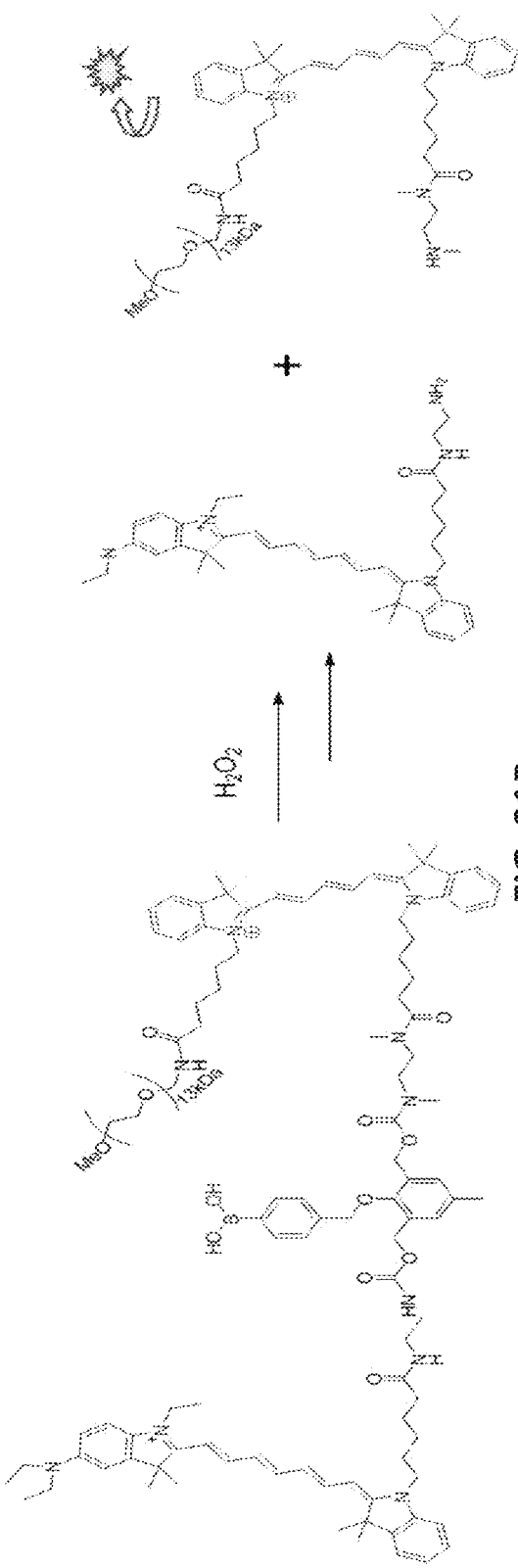
Figure 32B:
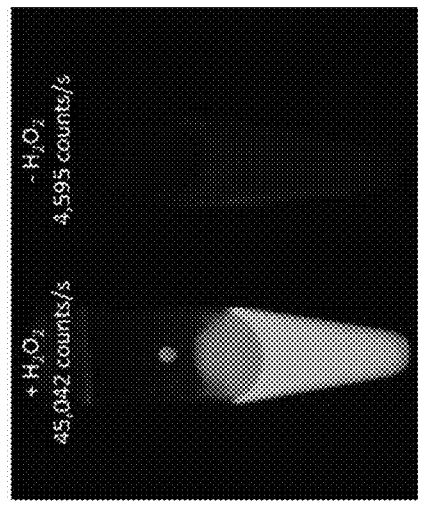

FIGS. 31A-B present a scheme depicting the structure and chemical synthesis of a FRET-based probe-polymer conjugate based on Cy5 conjugated to PEG, a latent central linker conjugated to phenyl-boronic ester as a triggering substrate for hydrogen peroxide, and a quencher (FIG. 31A), and the generation of a fluorescent signal upon contact with hydrogen peroxide (FIG. 32B).

Figure 32A:
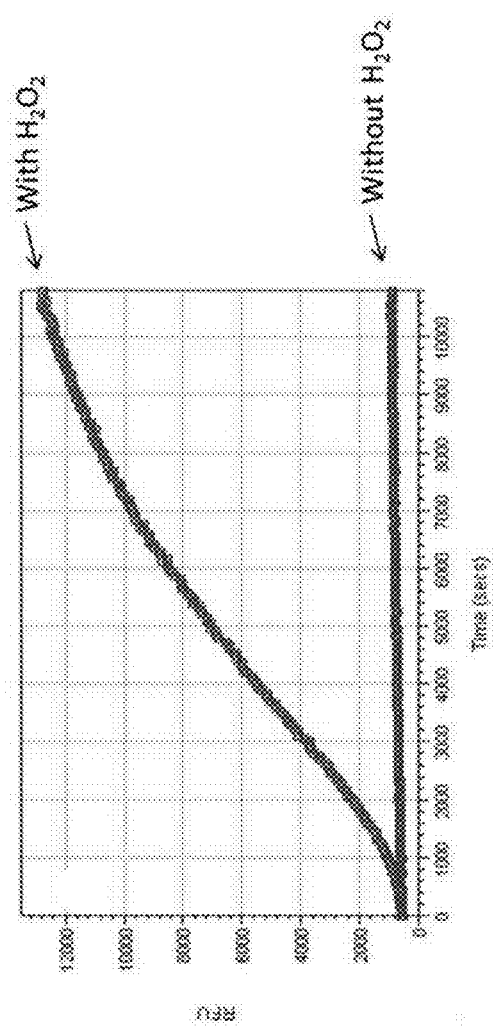

FIGS. 32A-B present comparative plots (FIG. 32A) showing the NIR fluorescence ($\lambda$ex=630 nm, $\lambda$em=670 nm) emitted upon incubation of the Cy5-PEG conjugate [30 μM] in the presence or absence of hydrogen peroxide (5 equivalents) in 0.1 M PBS, pH 7.4, monitored by RP-HPLC; gradient: 10-90% ACN in 0.1% TFA in water; and images acquired using CRI Maestro™ Imaging system (FIG. 32B).

Figure 33:

FIG. 33 presents an image acquired using CRI Maestro™ Imaging system ($\lambda$ex=630 nm, $\lambda$em=670 nm) of SCID mice bearing -U-87 MG tumors, 2 minutes after injection i.v. of 200 μl of a 1 μM solution of a PEG-Cy5 conjugate via the tail vein.

Figure 34:
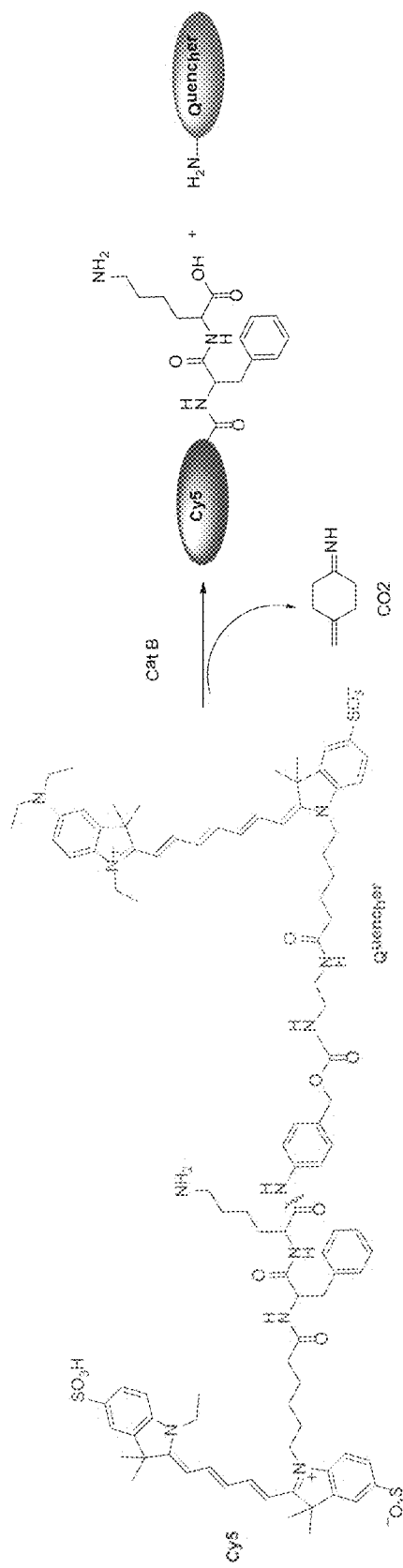

FIG. 34 presents the chemical structure and a schematic illustration of the activation mechanism of a FRET-based cathepsin B fluorescent probe with the cyanine dye Cy5.

Figure 35:
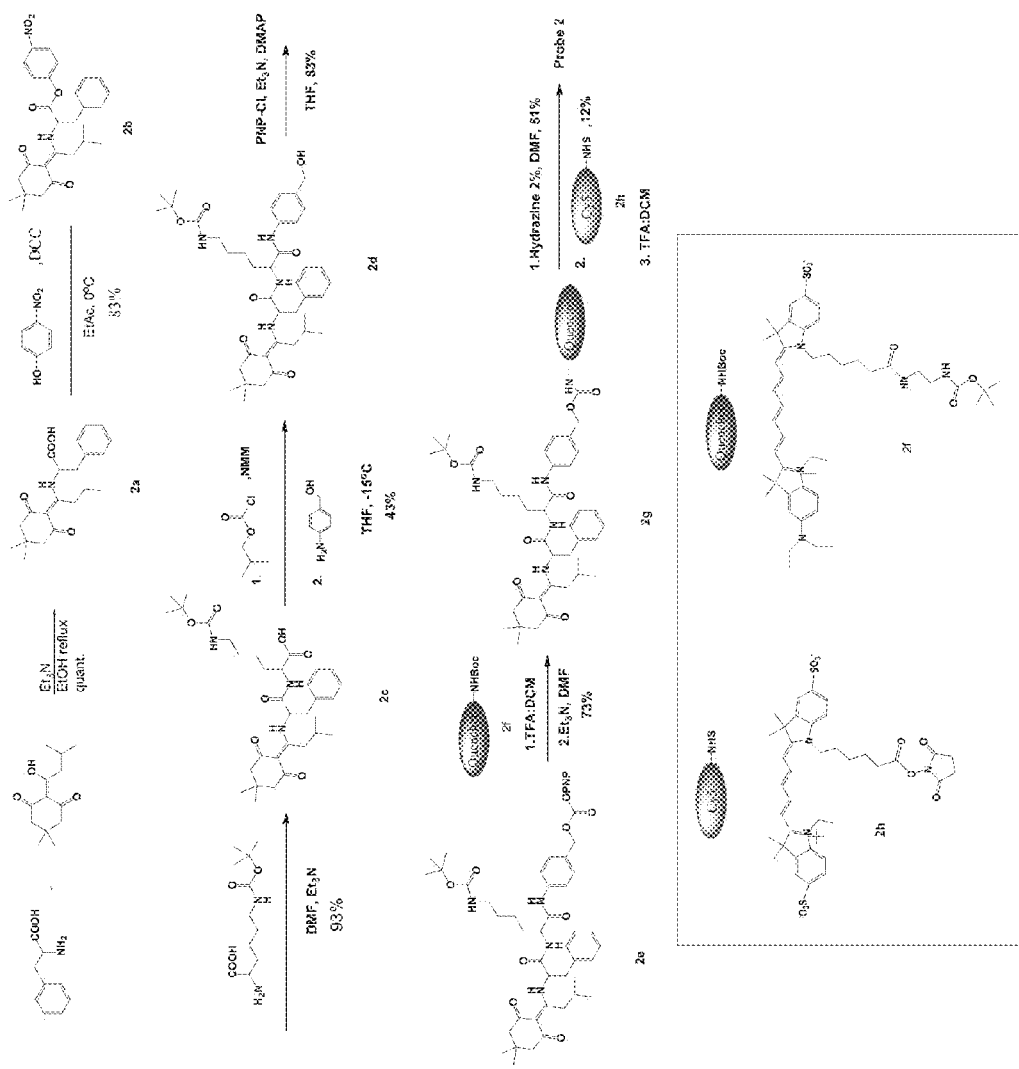

FIG. 35 is a scheme depicting a synthetic pathway for preparing a FRET-based cathepsin B-activated fluorescent probe with the cyanine dye Cy5.

Figure 36:
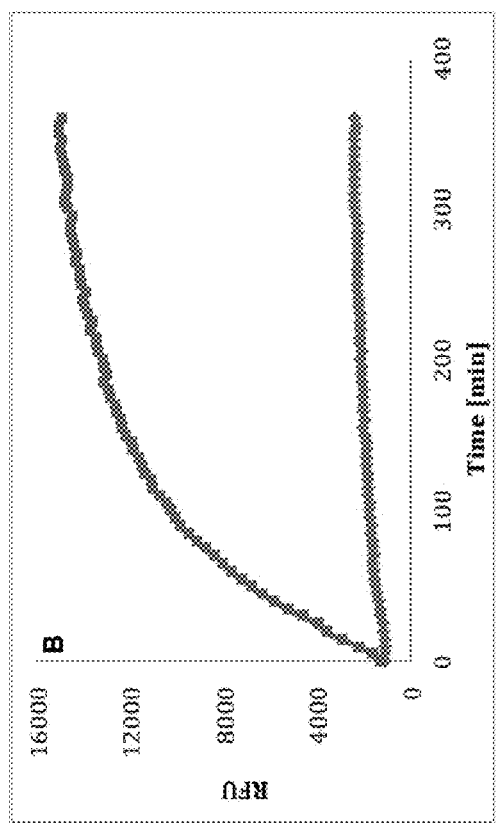

FIG. 36 presents comparative plots showing the NIR fluorescence ($\lambda$ex=620 nm, $\lambda$em=670 nm) emitted upon incubation of a FRET-based cathepsin B fluorescent probe with the cyanine dye Cy5 [25 μM, 10% DMSO] in the presence (red) or absence (blue) of cathepsin B [1.4 U/ml] in activity buffer (pH=6.0) solution.

Figure 37B:
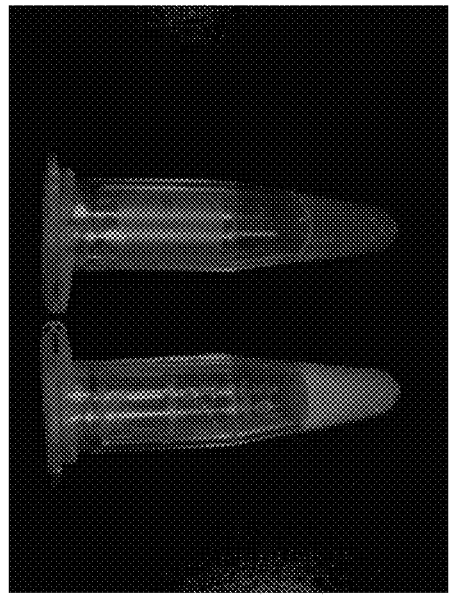
Figure 37A:
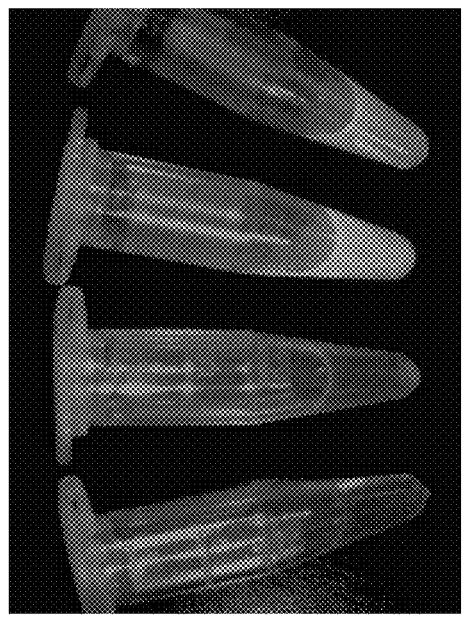

FIGS. 37A-B present comparative images showing the NIR fluorescence turn-ON response of a FRET-based cathepsin B fluorescent probe with the cyanine dye Cy5 upon reaction with cathepsin B (solutions in activity buffer of pH 6.0). FIG. 37A presents images of the probe [0.01 mM] in the presence and in the absence of cathepsin B [10 U/ml] (1 minute after enzyme's addition) (most and second left vials, respectively), and of and Cy5 [0.01 mM] under the same conditions (third and fourth from the left, respectively. FIG. 37B presents images of the probe [0.01 mM] in the presence (4 hours after addition) and in the absence of cathepsin B [10 U/ml]. Images were taken by CRI Maestro™ Imaging system. Filter set: excitation at 635 nm, emission cut-off filter of 675 nm.

Figure 38:
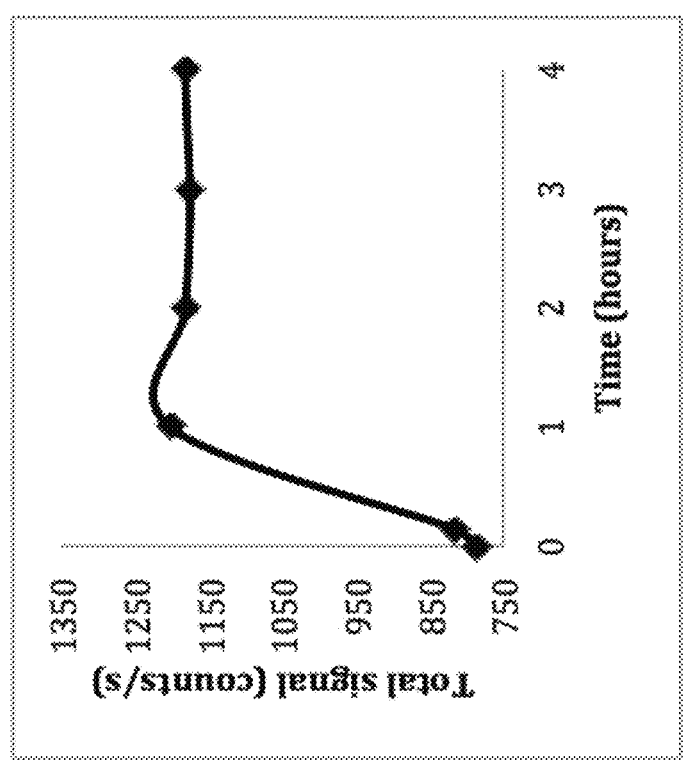

FIG. 38 presents a quantification of time-dependent fluorescence signal upon intratumoral injection of a FRET-based cathepsin B fluorescent probe into cathepsin B-overexpressing 4T1 mammary adenocarcinoma [50 μl; 0.01 mM]. Images were acquired and quantified using non-invasive intravital CRI Maestro™ imaging system. Filter set: excitation at 635 nm, emission cut-off filter of 675 nm.

Figure 39:
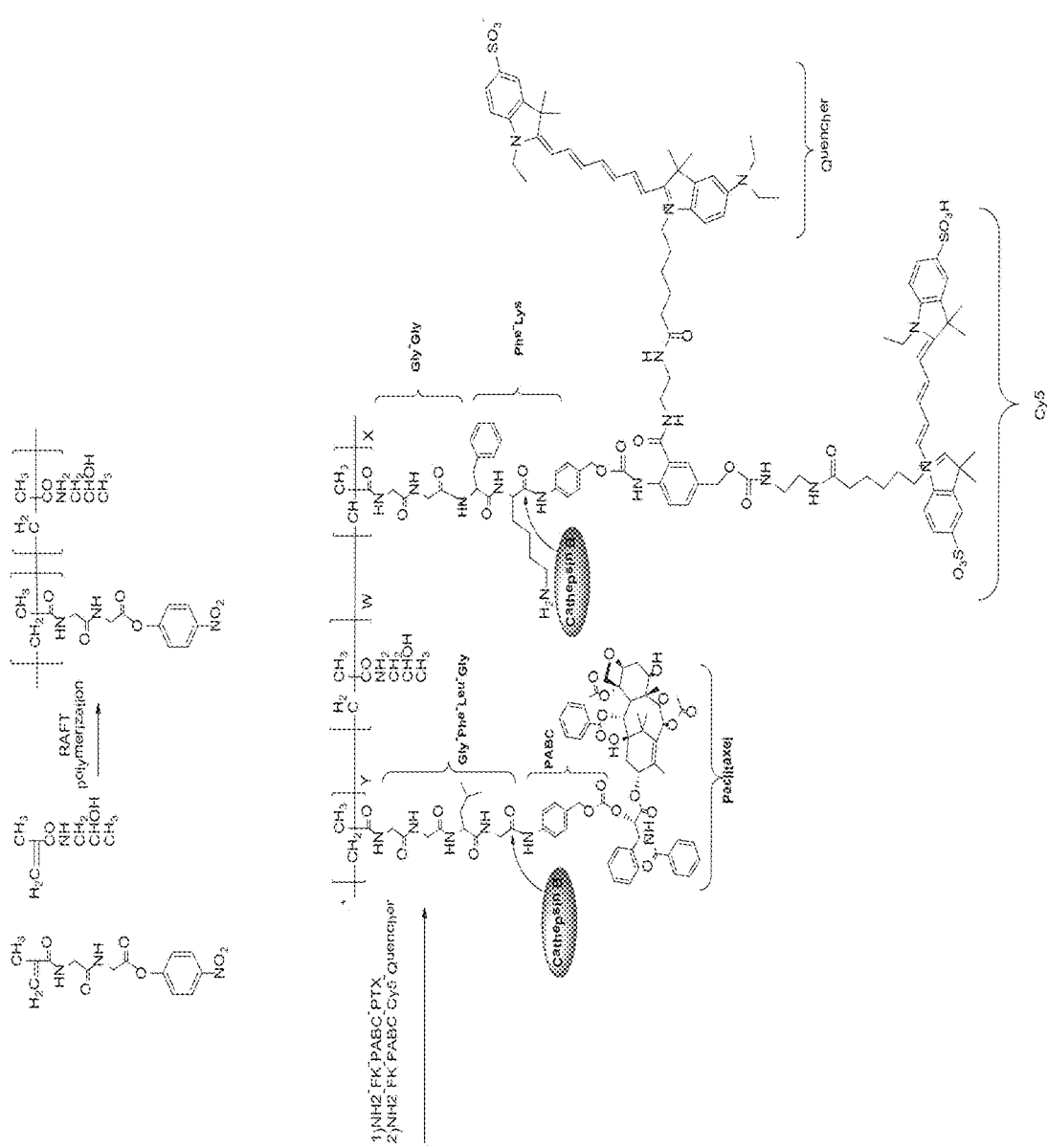

FIG. 39 is a scheme depicting the synthesis of HPMA copolymer-Gly-Gly-Phe-Lys-PABC-PTX-Cy5-Quencher by RAFT polymerization of copolymer precursor HPMA-Gly-Gly-ONp followed by coupling to amine-Phe-Lys-PABC-PTX, amine-Phe-Lys-PABC-Cy5-Quencher as an example for FRET-based fluorescent Turn-On moiety.

Figure 40:
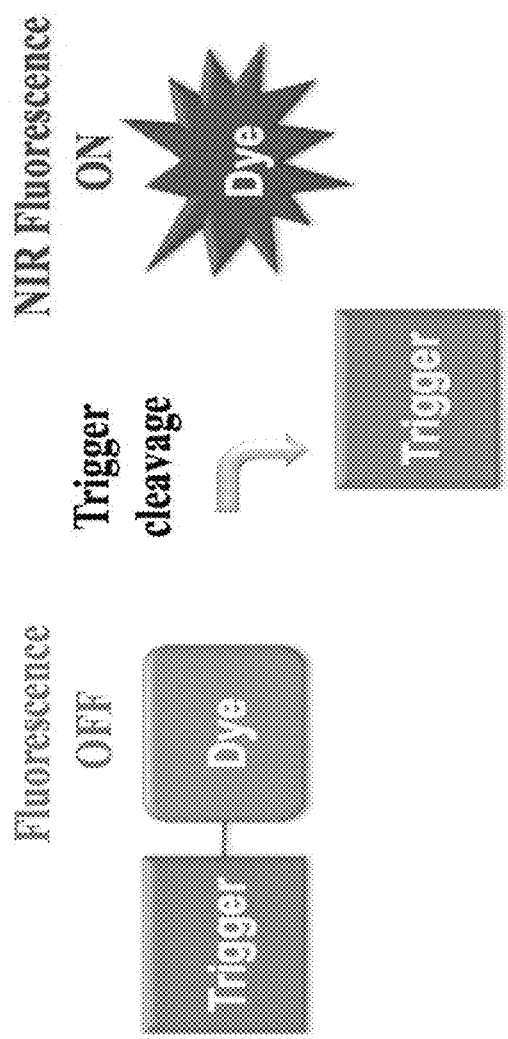

FIG. 40 presents a schematic illustration of a general design and mode of action of an ICT-based fluorescent probe.

Figure 41:
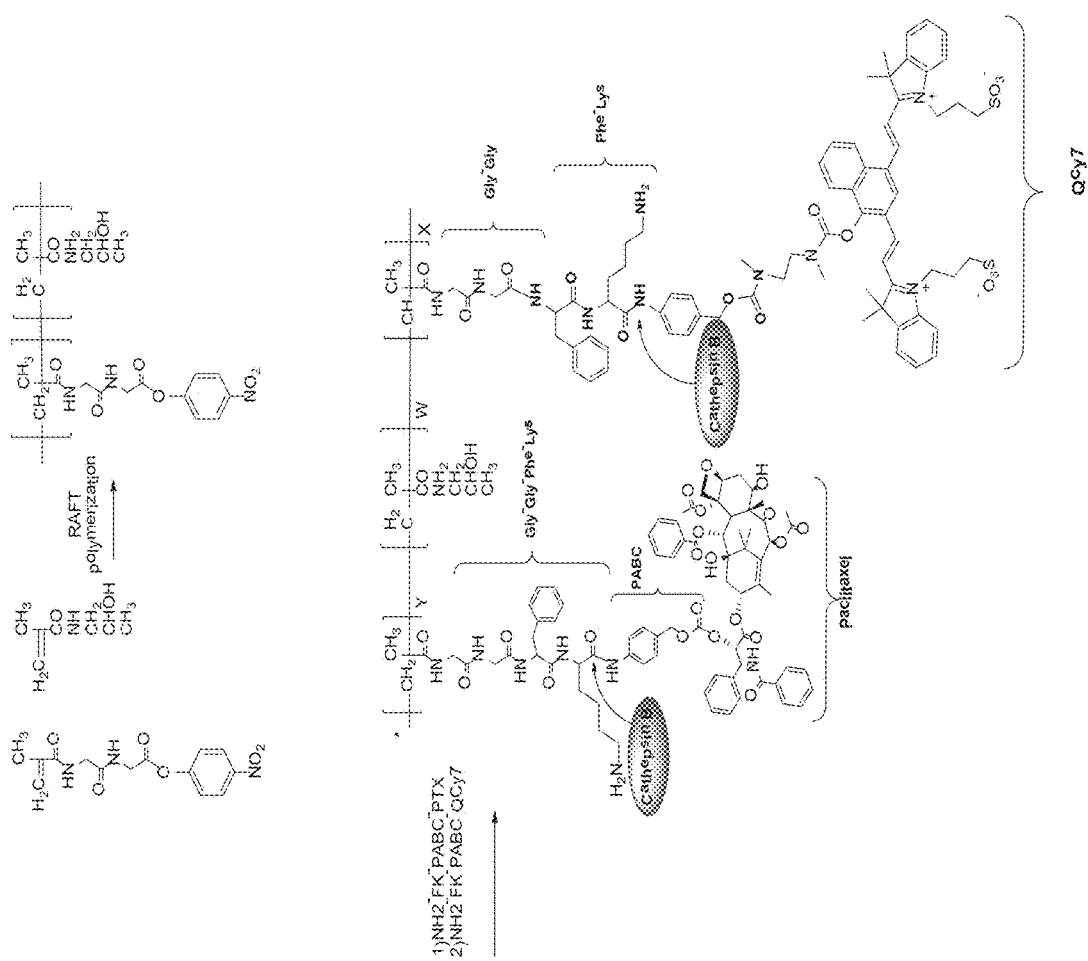

FIG. 41 is a scheme depicting the synthesis of HPMA copolymer-Gly-Gly-Phe-Lys-PABC-PTX-QCy7 by RAFT polymerization of copolymer precursor HPMA-Gly-Gly-ONp followed by coupling to amine-Phe-Lys-PABC-PTX, amine-Phe-Lys-PABC-QCy7 as an example for ICT-based fluorescent Turn-On moiety.

Figure 42:
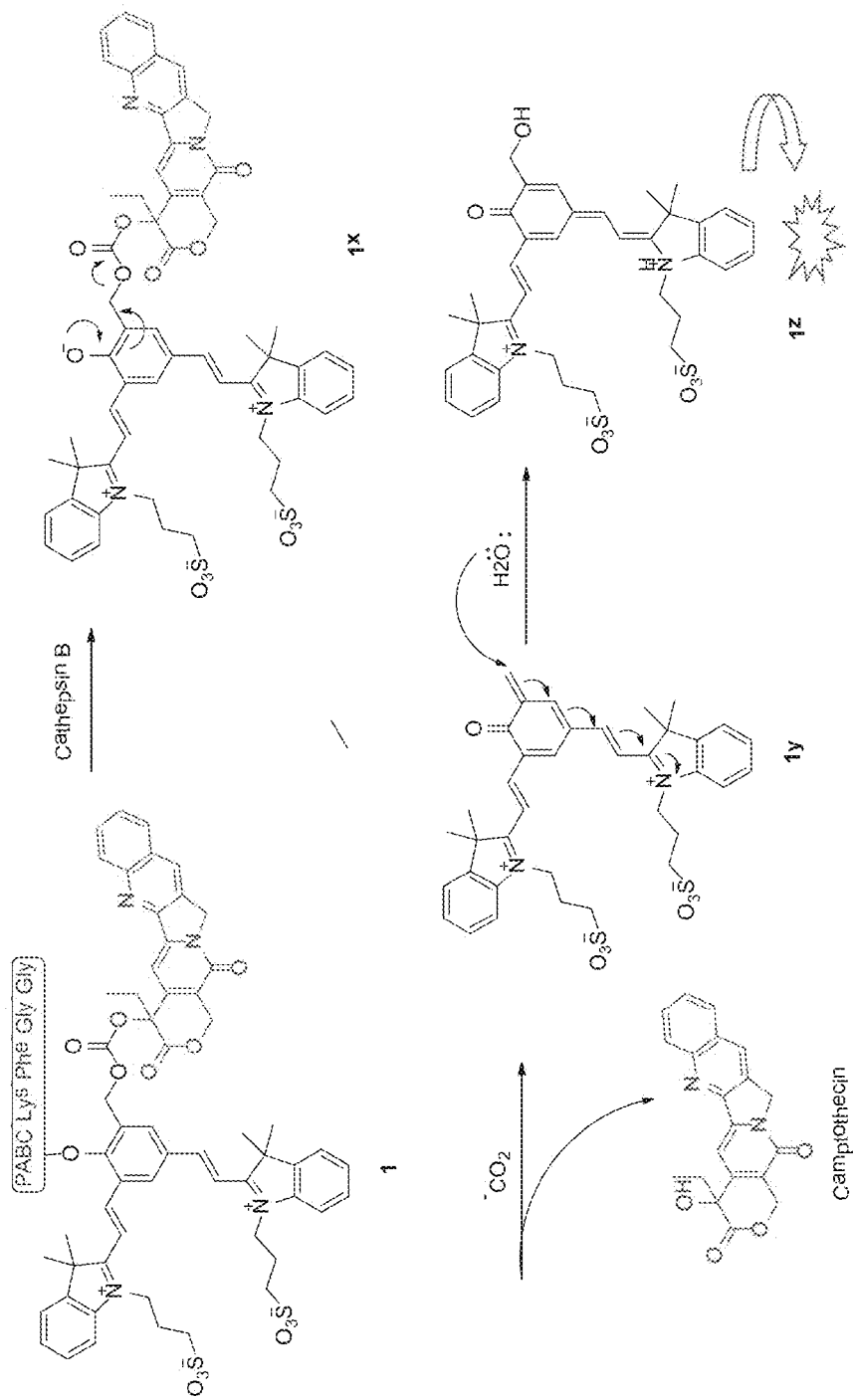

FIG. 42 is a schematic illustration presenting an activation mechanism of QCy7-based probe by cathepsin B to release free Camptothecin drug and produce a fluorescent turn-ON response.

DESCRIPTION OF SPECIFIC EMBODIMENTS OF THE INVENTION

The present invention, in some embodiments thereof, relates to therapy and diagnosis (theranostic) and, more particularly, but not exclusively, to polymeric systems in which a labeling agent or a labeling agent and a therapeutically active agents are attached to a polymeric backbone, to probes useful for inclusion in such polymeric systems, and to uses thereof in diagnostic and theranostic applications.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present invention, in some embodiments thereof, relates to therapy and diagnosis (theranostic) and, more particularly, but not exclusively, to polymeric systems in which a labeling moiety (e.g., a fluorescent or fluorogenic moiety) or a labeling moiety and a therapeutically active agents are attached to a polymeric backbone, and to uses thereof in diagnostic and theranostic applications.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have now devised and successfully practiced two theranostic systems, which permit simultaneous drug release and imaging ability: (i) a polymeric system composed of two separate polymeric moieties, one designed to release a therapeutically active agent and one designed to generate a fluorescent signal; and (ii) a combined polymeric system in which a fluorogenic moiety and therapeutically active agent are attached to a single polymeric backbone.

In some embodiments, the diagnostic system is composed of an efficient high-loading, FRET-based (self-quenched (SQ) or paired) "Turn-ON" system with a NIR fluorescent cyanine dye or an analog thereof. In some embodiments, the therapeutic system includes a therapeutically active agent, such as an anti-cancer agent (e.g., paclitaxel; PTX).

In some embodiments, the polymers are water soluble, non-toxic, biocompatible and stable polymers (e.g., HPMA, PEG or the biodegradable PGA).

In some embodiments, the cyanine dye and/or a therapeutically active agent are conjugated to the polymeric backbone in a manner enabling their site-specific cleavage, for example, by a tumor-specific enzyme such as cathepsin B.

According to an aspect of some embodiments of the present invention there is provided a polymeric system comprising a first polymeric moiety which comprises a first polymeric backbone composed of a plurality of backbone units and having attached to at least a portion of the backbone units a fluorogenic moiety, the fluorogenic moiety being attached to the backbone units via a first cleavable linking moiety such that upon cleavage of the linking moiety, a fluorescent signal is generated. The first polymeric moiety described herein represents the diagnostic part of a theranostic system. The first polymeric moiety described herein is a polymeric conjugate in which a fluorogenic moiety is conjugated to the first polymeric backbone.

According to some of any of the embodiments of the present invention, the polymeric system further comprises a therapeutically active agent.

In some embodiments, the polymeric system comprises a second polymeric moiety which comprises a second polymeric backbone composed of a plurality of backbone units and having attached to at least a portion of the backbone units a therapeutically active agent. This second polymeric moiety represents the therapeutic part of a theranostic system. The second polymeric moiety described herein is a polymeric conjugate in which a therapeutically active agent is conjugated to the second polymeric backbone. The second polymeric backbone can be the same or different from the first polymeric backbone. In some of these embodiments, the therapeutically active agent is attached to the backbone units via a second cleavable linking moiety, which can be the same as or different from the first cleavable linking moiety.

In some embodiments, the therapeutically active agent is attached to a portion of the backbone units of the first polymeric backbone, such that the fluorogenic moiety is attached, via the cleavable linking moiety, to one portion of the backbone units, and the therapeutically active agent is attached to another portion of the backbone units. Such a polymeric system represents a single polymeric theranostic system. In some of these embodiments, the therapeutically active agent is attached to the backbone units via a second cleavable linking moiety, which can be the same as or different from the first cleavable linking moiety. Such a system can be regarded as a polymeric system which comprises two polymeric moieties or polymeric conjugates, each comprising a polymeric backbone, namely, a first and a second polymeric backbone as described herein, whereby the second polymeric backbone forms a part of the first polymeric backbone, resulting in a polymeric backbone in which the fluorogenic moiety is attached, via the cleavable linking moiety, to one portion of the backbone units, and the therapeutically active agent is attached to another portion of the backbone units.

In some embodiments, the therapeutically active agent forms a part of the fluorogenic moiety, such that upon the cleavage of the first cleavable linking moiety, the therapeutically active agent is released and a fluorescent signal is generated. Such a polymeric system represents a single polymer theranostic system.

In some embodiments, the therapeutically active agent and the fluorogenic moiety are both attached to the first cleavable linking moiety, for example, by means of a spacer, as described herein, such that upon cleavage of the first cleavable linking moiety, the therapeutically active is released and a fluorescent signal is generated. Such a polymeric system represents a single polymer theranostic system.

Thus, in some embodiments of the present invention the polymeric system can comprise two (or more) polymeric conjugates, each comprising a polymeric backbone, which can be the same or different. One of the polymeric conjugates, referred to herein as a first polymeric moiety, comprises a fluorogenic moiety attached to a portion of the backbone units of a first polymeric backbone. Another polymeric conjugate, referred to herein as a second polymeric moiety, comprises a therapeutically active agent attached to a portion of the backbone unit of the second polymeric backbone.

In other embodiments of the present invention, the polymeric system comprises one polymeric conjugate, referred to herein as a first polymeric moiety, in which both the fluorogenic moiety and the therapeutically active agent are attached to the same polymeric backbone, each being attached to a portion of the backbone units in the polymeric backbone. In these embodiments, the second polymeric backbone forms a part of the first polymeric backbone, such that the conjugate comprises one polymeric backbone.

According to some embodiments of the invention, the first and the second polymeric backbones are not covalently associated therebetween, such that the system comprises two separate polymeric conjugates (polymeric moieties).

According to some embodiments of the invention, the second polymeric backbone forms a part of the first polymeric backbone, such that the polymeric system comprises a polymeric backbone comprising a plurality of backbone units having the fluorogenic moiety attached to one portion of the backbone units and having the therapeutically active agent attached to another portion of the backbone units, such that the system comprises one polymeric conjugate or moiety as described herein.

In some of any of the embodiments described herein, the fluorogenic moiety is attached to the first cleavable linking moiety via a spacer. In some embodiments, the first cleavable linking moiety is attached to the respective portion of backbone units of the first polymeric backbone via a spacer.

In some of any of the embodiments described herein, the therapeutically active agent is attached to the second cleavable linking moiety via a spacer. In some embodiments, the second cleavable linking moiety, if present, is attached to the respective portion of backbone units of the polymeric backbone via a spacer.

In some of the embodiments described herein, when the therapeutically active agent forms a part of the fluorogenic moiety, the therapeutically active agent is attached to the fluorogenic moiety via a spacer.

In some of any of these embodiments, the spacer is a degradable spacer, as described herein.

In some of any of the embodiments described herein, the first polymeric moiety, which comprises the fluorogenic moiety, further comprises a quenching agent, as described herein.

In some embodiments, the quenching agent is attached to a portion of the backbone units of the first polymeric backbone, such that the fluorogenic moiety is attached to one portion of the backbone units of the first polymeric backbone and the quenching agent is attached to another portion of the backbone units of the first polymeric backbone.

In some embodiments, the quenching agent is attached to a terminus of the first polymeric backbone, that is, the quenching agent is attached to a terminal backbone unit of the first polymeric backbone.

The quenching agent can be attached to the backbone unit(s) via a linking moiety, or via a spacer, which can be degradable or non-degradable.

In some embodiments, the quenching agent forms a part of the fluorogenic moiety. In some of these embodiments, the quenching agent is attached to a fluorescent moiety via a spacer.

The polymeric conjugates described herein can be used each separately or in any combination thereof.

The Polymer:

As used herein, the term "polymer" or "polymeric moiety" describes a substance composed of a plurality of repeating structural units (backbone units) covalently connected to one another and forming a polymeric backbone. The term "polymer" as used herein encompasses organic and inorganic polymers and further encompasses one or more of a homopolymer, a copolymer or a mixture thereof (a blend). The term "homopolymer" as used herein describes a polymer that is made up of one type of monomeric units and hence is composed of homogenic backbone units. The term "copolymer" as used herein describes a polymer that is made up of more than one type of monomeric units and hence is composed of heterogenic backbone units. The heterogenic backbone units can differ from one another by the pendant groups thereof.

The term "polymer" or "polymeric moiety" is used herein to describe the polymeric backbone to which the agents/moieties described herein are attached.

The polymer comprises a polymeric backbone which is comprised of backbone units whereby one or more of the therapeutically active and the fluorogenic moiety, and optionally other agents and/or moieties as described herein, are attached to at least a portion of these backbone units. Some or all of these backbone units are typically functionalized prior to conjugation, so as to have a reactive group for attaching the therapeutically active agent and/or the fluorogenic moiety and/or other agents or moieties. Those backbone units that are not functionalized and/or do not participate in the conjugation of the therapeutically active agent and/or the fluorogenic moiety and/or other agents or moieties, are referred to herein as "free" backbone units.

Polymers which are suitable for use in the context of the present embodiments are biocompatible, non-immunogenic and non-toxic. The polymers serve as carriers that enable targeting to and delivery into tumor tissue, possibly due to the EPR effect.

The polymer may be a biostable polymer, a biodegradable polymer or a combination thereof. The term "biostable", as used in this context of embodiments of the invention, describes a compound or a polymer that remains intact under physiological conditions (e.g., is not degraded in vivo).

The term "biodegradable" describes a substance which can decompose under physiological and/or environmental conditions into breakdown products. Such physiological and/or environmental conditions include, for example, hydrolysis (decomposition via hydrolytic cleavage), enzymatic catalysis (enzymatic degradation), and mechanical interactions. This term typically refers to substances that decompose under these conditions such that 50 weight percents of the substance decompose within a time period shorter than one year.

The term "biodegradable" as used in the context of embodiments of the invention, also encompasses the term "bioresorbable", which describes a substance that decomposes under physiological conditions to break down products that undergo bioresorption into the host-organism, namely, become metabolites of the biochemical systems of the host-organism.

The polymer can be water-soluble or water-insoluble. In some embodiments, the polymer is water soluble at room temperature.

The polymer can further be a charged polymer or a non-charged polymer. Charged polymers can be cationic polymers, having positively charged groups and a positive net charge at a physiological pH; or anionic polymers, having negatively charged groups and a negative net charge at a physiological pH. Non-charged polymers can have positively charged and negatively charged group with a neutral net charge at physiological pH, or can be non-charged.

In some embodiments, the polymer has an average molecular weight in the range of 100 Da to 800 kDa. In some embodiments, the polymer has an average molecular weight lower than 60 kDa. In some embodiments, the polymer's average molecular weight range is 15 to 40 kDa.

Polymeric substances that have a molecular weight higher than 10 kDa typically exhibit an EPR effect, as described herein, while polymeric substances that have a molecular weight of 100 kDa and higher have relatively long half-lives in plasma and an inefficient renal clearance. Accordingly, a molecular weight of a polymeric conjugate can be determined while considering the half-life in plasma, the renal clearance, and the accumulation in the tumor of the conjugate.

The molecular weight of the polymer can be controlled, at least to some extent, by the degree of polymerization (or co-polymerization).

The polymer used in the context of embodiments of the invention can be a synthetic polymer or a naturally-occurring polymer. In some embodiments, the polymer is a synthetic polymer.

The polymeric backbone of a polymeric conjugate as described herein may be derived from, or correspond to, a polymeric backbone of polymers such as, for example, polyacrylates, polyvinyls, polyamides, polyurethanes, polyimines, polysaccharides, polypeptides, polycarboxylates, and mixtures thereof.

Exemplary polymeric backbones which are suitable for use in the context of the present embodiments are polymeric backbones which correspond to the polymeric backbones of polymers such as, but are not limited to, polyglutamic acid (PGA), a poly(hydroxyalkylmethaacrylamide) (HPMA), a polylactic acid (PLA), a polylactic-co-glycolic acid (PLGA), a poly(D,L-lactide-co-glycolide) (PLA/PLGA), a polyamidoamine (PAMAM), a polyethylenimine (PEI), dextran, pollulan, a water soluble polyamino acid, and a polyethylenglycol (PEG).

These polymers can be of any molecular weight, as described herein, and preferably have a molecular weight within the range of 10 to 60 kDa, or of 10 to 40 kDa.

It is to be understood that the polymers as discussed herein describe those polymers that are formed from homogenic or heterogenic, non-functionalized monomeric units, and that the polymeric backbone constituting the polymeric conjugates disclosed herein corresponds to such polymers by being comprised of the same monomeric units, while some of these monomeric backbone units have moieties attached thereto, as described herein. Thus, the polymeric backbone of a polymeric conjugate is similar to that of the polymers described herein, and differs from the polymers by having the above-described agents attached to at least some of the backbone units therein.

In some of any of the embodiments described herein, the polymeric backbone of a polymeric moiety or conjugate corresponds to (as described herein), or is derived from (as described herein), a polymeric backbone of a poly(hydroxyalkylmethaacrylamide) or a copolymer thereof. Such a polymeric backbone comprises methacrylamide backbone units having attached thereto either 2-hydroxypropyl groups or such 2-hydroxypropyl groups that have been modified by attaching thereto (directly or indirectly) the moieties described herein (e.g., therapeutically active agent(s) and/or fluorogenic moiety).

Poly(hydroxyalkylmethacrylamide) (HPMA) polymers are a class of water-soluble synthetic polymeric carriers that have been extensively characterized as biocompatible, non-immunogenic and non-toxic. One advantage of HPMA polymers over other water-soluble polymers is that they may be tailored through relatively simple chemical modifications, in order to regulate their respective drug and targeting moiety content. Further, the molecular weight and charge of these polymers may be manipulated so as to allow renal clearance and excretion from the body, or to alter biodistribution while allowing tumor targeting.

In some of any of the embodiments described herein, the polymeric backbone is derived from, or corresponds to, polyglutamic acid (PGA). PGA is a polymer composed of units of naturally occurring L-glutamic acid linked together through amide bonds. The pendant free γ-carboxyl group in each repeating unit of L-glutamic acid is negatively charged at a neutral pH, which renders the polymer water-soluble. The carboxyl groups also provide functionality for drug attachment. PGA is biodegradable and FDA-approved.

Cysteine proteases, particularly cathepsin B, play key roles in the lysosomal degradation of PGA to its nontoxic basic components, L-glutamic acid, D-glutamic acid and D,L-glutamic acid. The cellular uptake of negatively charged polymers can be hindered due to electrostatic repulsion forces between the polymers and the rather negatively charged surface of the cells. Although PGA is no exception to this rule, it does not diminish the EPR effect and the accumulation and retention of PGA-drug conjugates in solid tumors. Specific receptor-mediated interactions of PGA-drug conjugates containing targeting ligands may also increase the rate of polymer uptake into the target cells.

As used herein, "a polyglutamic acid" or "polyglutamic acid polymer" encompasses poly(L-glutamic acid), poly(D-glutamic acid), poly(D,L-glutamic acid), poly(L-gamma glutamic acid), poly(D-gamma glutamic acid) and poly(D, L-gamma glutamic acid).

PGA is usually prepared from poly(γ-benzyl-L-glutamate) by removing the benzyl protecting group with the use of hydrogen bromide. A sequential copolymer of protected PGA may be synthesized by peptide coupling reactions. For the preparation of high-molecular-weight homopolymers and block or random copolymers of protected PGA, triethylamine-initiated polymerization of the N-carboxyanhydride (NCA) of γ-benzyl-L-glutamate is used.

Water-soluble copolymers such as N-2-hydroxypropyl methacrylamide (HPMA) copolymer and polyglutamic acid (PGA) are biocompatible, non-immunogenic and non-toxic carriers that enable specific delivery into tumor tissue (Satchi-Fainaro et al. *Nat Med* 2004; 10: 255-261). These macromolecules do not diffuse through normal blood vessels but rather accumulate selectively in the tumor site because of the EPR effect. This phenomenon of passive diffusion through the hyperpermeable neovasculature and localization in the tumor interstitium is observed in many solid tumors for macromolecular agents and lipids.

For any of the polymeric moieties or conjugates described herein, the plurality of the backbone units forming the polymeric backbone in the conjugate comprises two or more different portions of backbone units that differ from one another by the presence and/or nature of the moiety or agent attached thereto. For example, one portion of the backbone units are "free" backbone units, and one portion of the backbone units have a fluorogenic moiety attached thereto. In another example, a third portion of the backbone units have a therapeutically active agent attached thereto, or a quenching agent attached thereto.

The different backbone units that have a moiety or agent attached thereto can be randomly dispersed within the polymeric backbone.

Thus, in some embodiments, a polymeric backbone as described herein is formed of a plurality of backbone monomeric units, which are covalently linked to one another so as to form the polymeric backbone. The backbone units are therefore such that, if not having certain moieties attached thereto, as described herein, form a polymeric backbone of a polymer. The plurality of backbone units as described herein, and the polymeric backbone comprised thereof, are therefore also defined herein as derived from, or corresponding to, the polymeric backbone of such a polymer. The plurality of backbone units as described herein, and the polymeric backbone comprised thereof, therefore correspond to, or are derived from, a polymer, whereby one or more moieties or agents, as described herein, are attached to one or more portions of the backbone units. Since once the one or more moieties are attached to one or more portions of the backbone units forming the polymeric backbone, the backbone units forming the polymeric backbone are not identical to one another, as is the case of an "intact" polymer, and hence the polymeric conjugate is actually a copolymer, or has a copolymeric backbone, which is comprised of two or more types of backbone units. The phrase "polymeric backbone" as used herein therefore describes a "copolymeric backbone" comprised of at least two different types of backbone units.

It is to be noted that portions of the backbone units differ from one another by the presence and type of the moiety or agent that are attached to the backbone unit, but maintain the chemical structure of the portion of the backbone unit that forms the polymeric backbone. In analogy to a peptide, where the portions of the backbone units differ from one another by the side chain of the amino acid, the portions of the backbone units differ from one another by the presence and/or nature of the pendant group thereof.

In some of any of the embodiments described herein, a polymeric conjugate or moiety as described herein comprises a polymeric (or copolymeric) backbone formed from a plurality of backbone units, and the plurality of backbone units comprise one or more of the following backbone units:

-$A_1$-, which represents a backbone unit within the polymeric backbone, or, in other words, a backbone unit of the polymer from which the polymeric backbone is derived, and is "free" of moieties that attached thereto;

-$A_2$-, which represents a backbone unit of the polymer from which the polymeric backbone is derived (a backbone unit within the polymeric backbone), having a fluorogenic moiety (F), as described herein, attached thereto via a cleavable linking moiety, as described in further detail hereinafter;

-$A_3$-, which represents a backbone unit of the polymer from which the polymeric backbone is derived (a backbone unit within the polymeric backbone), having a therapeutically active agent (D), as described herein attached thereto, optionally via a cleavable linking moiety, as described in further detail hereinafter;

-A₄-, which represents a backbone unit of the polymer from which the polymeric backbone is derived (a backbone unit within the polymeric backbone), having a quenching agent attached thereto; and optionally -A₅-, which represents a backbone unit of the polymer from which the polymeric backbone is derived (a backbone unit within the polymeric backbone), having a functional/reactive group attached thereto. Such backbone units can be present in a polymeric moiety as described herein, in cases where a polymer comprising a plurality of functionalized backbone units is used for forming a polymeric conjugate as described herein, whereby not all the functionalized backbone units participate in the conjugation reaction to form one or more of A₂, A₃ or A₄ as described herein. Such backbone units can be regarded as "free" backbone units to the extent that they do not contain a moiety or agent as described herein conjugated thereto, yet they contain a reactive/functional pendant group, which is denoted herein as R.

The backbone units can be arranged within the polymeric backbone in any order, such that each of the backbone units can be a terminal backbone unit, which is attached to one other backbone unit, or is attached to two other backbone units, which can be the same or different.

In some of any of the embodiments of the present invention, a polymeric moiety or conjugate as described herein comprises at least backbone units A₂ as described herein, and optionally also backbone units A₁, and further optionally also backbone units A₄ and A₅. Such a polymeric moiety represents a diagnostic part of a theranostic system, and in some embodiments, a polymeric system comprising such a polymeric moiety, further comprises a second polymeric moiety.

In some of these embodiments, the second polymeric moiety comprises backbone units A₃ as described herein, and optionally also backbone units A₁, and further optionally also backbone units A₅.

In some of any of the embodiments of the present invention, a polymeric moiety or conjugate as described herein comprises backbone units A₁, A₂ and A₃ as described herein, and optionally also backbone units A₄ and A₅.

In some of any of the embodiments of the present invention, the moiety or agent attached to the backbone units can be conjugated or attached directly to pendant group of the backbone units, or indirectly, via a spacer or a linker, as described herein.

In some embodiments, the plurality of backbone units forming the polymeric backbone comprises the following portions of backbone units:

-(A₁)w-;
-(A₂-F)x-;
-(A₃-D)y-; and
-(A₄-Q)s,
and optionally -(A₅-R)z
wherein:
A₁ is a backbone unit within the polymeric backbone, as described herein;
A₂-F is a backbone unit within the polymeric backbone having attached thereto, via a cleavable linking moiety, a fluorogenic moiety F, as described herein;
A₃-D is a backbone unit within the polymeric backbone having attached thereto a therapeutically active agent D, as described herein;
A₄-Q is a backbone unit within the polymeric backbone having attached thereto a quenching agent (Q), as described herein;
and A₅ in a functionalized backbone unit within the polymeric backbone, as described herein, wherein R is said reactive or functional group.

The backbone units can further comprise second and third linking moieties, and/or spacers, through which the agents or moieties are attached, as described in further detail hereinafter.

Herein, the phrases "loading onto the polymer", or simply "load", are used to describe the amount of an agent or moiety that is attached to the polymeric backbone of the conjugates described herein, and is represented herein by the mol percent (mol %) of the backbone units having the agent or moiety attached thereto, as defined hereinafter.

Herein "mol percent" represents the number of moles of backbone units having the agent or moiety attached thereto, as defined hereinafter, per 1 mol of the polymeric backbone, multiplied by 100, and hence represents the number of moles of an attached moiety or agent per 1 mol of the polymer, multiplied by 100.

The % loading can be measured by methods well known by those skilled in the art, some of which are described hereinbelow under the Materials and Methods of the Examples section that follows.

The mol percent of each of the backbone units is represented herein by "w", "x", "y", "s", and "z", respectively. "x", "y" and "s" represent the loading of the respective moieties.

In some of any of the embodiments described herein, a load of a therapeutically active agent, when present within the polymeric moiety, denoted herein also as "y", ranges from 0.1 to 100 mol percent, or from 0.1 to 20 mol percent, and can be, for example, 0.1, 0.5, 1, 2, 3, 4, 5, 6, 7, 8, 9, 10, 11, 12, 13, 14, 15, 16, 17, 18, 19 and 20, and even higher values, including any subranges and values therebetween.

In some of any of the embodiments described herein, the load of the fluorogenic moiety, denoted also as "x" herein, ranges from 0.1 to 100 mol percent, or from 0.1 to 20 mol percent, or from 1 to 20 mol percent, and can be, for example, 0.1, 0.5, 1, 2, 3, 4, 5, 6, 7, 8, 9, 10, 11, 12, 13, 14, 15, 16, 17, 18, 19 and 20, and even higher values, including any subranges and values therebetween.

In some of any of the embodiments described herein, the load of the quenching agent, if present within separate backbone units, denoted also as "s" herein, ranges from 0.1 to 50 mol percent, or from 0.1 to 20 mol percent, or from 1 to 20 mol percent, and can be, for example, 0.1, 0.5, 1, 2, 3, 4, 5, 6, 7, 8, 9, 10, 11, 12, 13, 14, 15, 16, 17, 18, 19 and 20, and higher values, including any subranges and values therebetween.

According to some embodiments of the invention, w is an integer having a value such that x/(x+y+w+s+z) multiplied by 100 is in the range of from 70 to 99.9; y is an integer having a value such that y/(x+y+w+s+z) multiplied by 100 is in the range of from 0.01 to 20, as described herein; and x is an integer having a value such that w/(x+y+w+z+x) multiplied by 100 is in the range of from 0.01 to 20, as described herein.

For example w/(x+y+w+z+x) multiplied by 100 may be 71, 72, 73, 74, 75, 76, 77, 78, 79, 80, 81, 82, 83, 84, 85, 86, 87, 88, 89, 90, 91, 92, 93, 94, 95, 96, 97, 98, 99 or 99.9; y/(x+y+w+z+s) multiplied by 100 may be 0.01, 0.02, 0.03, 0.04, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14 or 15; x/(x+y+w+z+s) multiplied by 100 may be 0.01, 0.02, 0.03, 0.04, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14 or 15; s/(x+y+w+z+s) multiplied by 100 may be 0.01, 0.02, 0.03, 0.04, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14 or 15.

It would be appreciated that x, y, s, z and w can be controlled as desired by selecting the mol ratio of the respective monomeric units used for forming the polymeric conjugate, as discussed hereinbelow.

Any of the polymeric systems described herein, in some embodiments, have a large enough hydrodynamic diameter. The term "large enough" is used herein to describe a polymeric moiety having a hydrodynamic diameter which leads to an increase in the ratio of polymer accumulated in tumor tissue as compared to other tissues. The determination of the optimal ratio is well within the capability of those skilled in the art. For example, the ratio may be 1.1, 2, 3, 4, 5 etc. In some embodiments, the hydrodynamic diameter is in the range of from 15 nm to 200 nm. In some embodiments, the hydrodynamic diameter is in the range of from 50 nm to 150 nm. In some embodiments the hydrodynamic diameter is in the range of from 70 nm to 90 nm. In yet another embodiment the hydrodynamic diameter is 95 nm. The hydrodynamic diameter can be measured by methods known in the art.

The polymeric moieties described hereinabove may be administered or otherwise utilized in this and other aspects of the present invention, either as is, or as a pharmaceutically acceptable salt, enantiomer, diastereomer, solvate, hydrate or a prodrug thereof.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound. The neutral forms of the compounds are preferably regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of the present invention.

The phrase "pharmaceutically acceptable salts" is meant to encompass salts of the moieties and/or polymeric backbone which are prepared with relatively nontoxic acids or bases, depending on the particular substituents found on the compounds described herein. When polymeric moieties of the present embodiments contain relatively acidic functionalities, base addition salts can be obtained by contacting the neutral (i.e., non-ionized) form of such conjugates with a sufficient amount of the desired base, either neat or in a suitable inert solvent. Examples of pharmaceutically acceptable base addition salts include sodium, potassium, calcium, ammonium, organic amino, or magnesium salt, or a similar salt. When polymeric moieties of the present invention contain relatively basic functionalities, acid addition salts can be obtained by contacting the neutral form of such polymeric moieties with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Polymeric moieties of the present embodiments may contain both basic and acidic functionalities that allow the conjugates to be converted into either base or acid addition salts.

The neutral forms of the polymeric moieties are preferably regenerated by contacting the salt with a base or acid and isolating the parent polymeric moiety in a conventional manner. The parent form of the polymeric moiety differs from the various salt forms in certain physical properties, such as solubility in polar solvents, but otherwise the salts are equivalent to the parent form of the polymeric moiety for the purposes of the present invention.

The Fluorogenic Moiety:

As generally stated in the art, the term "fluorogenic" encompasses a state or condition of having the capability to be fluorescent (i.e. to absorb and emit light, as defined hereinbelow) following a chemical, biochemical or physical occurrence or event. Thus, a "fluorogenic moiety" or a "fluorogenic compound" describes a non-fluorescent moiety or compound or a weakly fluorescent moiety or compound that becomes more fluorescent (e.g., by at least 10%, at least 20%, at least 30%, at least 40%, at least 50%, at least 60%, at least 70%, at least 80%, at least 90 5, at least 100% (at least 2-fold), optionally at least 3-fold, optionally at least 4-fold more fluorescent, and optionally at 10-fold or higher more fluorescent) upon the occurrence of a chemical, biochemical or physical event.

As used herein, a "chemical event" describes an event that involves a change in the chemical structure of a compound, including, but not limited to, bond cleavage, bond formation, protonation, deprotonation, oxidation, reduction, and more.

In some of any of the embodiments described herein, the chemical event is bond cleavage.

The phrase "fluorogenic moiety" as used herein therefore describes a moiety which changes its fluorescence upon a chemical event, and is therefore regarded, and in also referred to herein interchangeably, as a chemically-activatable fluorogenic moiety, as a probe, as a chemically-activatable probe or as a Turn-ON probe. The fluorogenic moieties described herein throughout are also referred to in the context of the fluorescent (dye) compounds or moieties generated upon said activation.

The phrase "Turn-ON" is used herein to describe a fluorogenic moiety, which upon a chemical event, becomes fluorescent, as defined herein. In the fluorogenic moiety, fluorescence is OFF, yet, upon being subjected to a chemical event, fluorescence turns ON (and a fluorescent signal is generated). The chemical event comprises a cleavage of a linking moiety, as described herein.

The phrase "fluorescent" refers to a compound or moiety that emits light upon return to the base state from a singlet excitation. The fluorescent compounds or moieties disclosed herein are also referred to herein throughout as dye compounds or dye molecules or as fluorophores or as fluorchromes.

In some embodiments, the emitted light is a near infrared light (near IR or NIR), being in the range of from about 700 nm to about 1400 nm. In some embodiments, the emitted light has emission maxima at a wavelength that is suitable for biological applications (e.g., in vivo applications), which ranges from 650 nm to 900 nm, and in some embodiments, from 700 nm to 800 nm.

Thus, a fluorogenic moiety as disclosed herein does not exhibit fluorescence and hence does not emit light at a near infrared range, for example, a light having a wavelength in the range of from about 650 nm to about 900 nm, and is designed such that it is capable of exhibiting fluorescence and thus of emitting light at such a near infrared range upon said cleavage.

In some embodiments, the emitted light is a UV-vis light. Thus, a fluorogenic moiety as disclosed herein does not exhibit fluorescence and hence does not emit light at a UV-vis range, and is designed such that it is capable of exhibiting fluorescence and thus of emitting light at such a UV-vis range upon said cleavage.

In some of any of the embodiments described herein, a fluorogenic moiety comprises a fluorescent moiety or compound, which is attached to said cleavable linking moiety (optionally via a spacer such as a degradable spacer), yet, the fluorescence of the moiety is quenched and hence is OFF. Once the linking moiety is cleaved, and the fluorescent moiety or compound is released from the polymeric moiety, and diffuses away therefrom, quenching is no longer effected, the fluorescence of the moiety turns ON, and a fluorescent signal is generated. A polymeric moiety or system comprising such a fluorogenic moiety is also referred to herein as a FRET system, or FRET-based system, as is discussed in detail hereinafter.

In some of these embodiments, the quenching of the fluorescence is self-quenching (SQ), and is effected by having at least two fluorescent moieties per a polymeric backbone. Once the linking moiety is cleaved, and the fluorescent moieties or compounds are released from the polymeric moiety, and diffuse away therefrom, self-quenching is no longer effected, the fluorescence of the moieties turns ON, and a fluorescent signal is generated.

In some of these embodiments, the quenching of the fluorecsence is effected by means of a quenching agent.

In some embodiments, the quenching agent is attached to one or more backbone units of the first polymeric backbone, and the fluorescent moiety is attached to other, one or more, backbone units of the polymeric backbone units, such that the fluorescence of the fluorescent moiety is quenched and is OFF. Once the linking moiety is cleaved, and the fluorescent moiety or compound is released from the polymeric moiety, and diffuses away therefrom, quenching is no longer effected, the fluorescence of the moiety turns ON, and a fluorescent signal is generated.

In other embodiments, the quenching agent forms a part of the fluorogenic moiety. In these embodiments, the fluorogenic moiety comprises a quenching agent attached to a fluorescent moiety, optionally via a spacer such as a degradable spacer, such that upon the cleavage of the first linking moiety, the fluorescent moiety is released, quenching is no longer effected, the fluorescence of the fluorescent moiety turns ON and a fluorescent signal is generated.

In some of any of the embodiments described herein, the fluorogenic moiety comprises a compound or a moiety which is non-fluorescent (i.e., does not absorb and emit light) or which has weak fluorescence (e.g., have a quantum yield lower by at least 2-fold than a quantum yield of a corresponding fluorescent molecule with the strong fluorescence), when attached to the polymeric backbone, and which becomes more fluorescent, as defined herein, upon a chemical event, due a change (rearrangement) in the structure of the compound or moiety. In some of these embodiments, the change in the structure of the compound or moiety involves relocalization of $\pi$-electrons, as a result of the chemical event (cleavage of the linking moiety), which may generate, for example, a conjugated $\pi$-electron system, which accounts for fluorescence. A polymeric moiety or system comprising such a fluorogenic moiety is also referred to herein as an ICT system, or ICT-based system, as is discussed in detail hereinafter.

In some of any of the embodiments described herein, the fluorogenic moiety has a cyanine-like structure and the fluorescent moiety or compound is a cyanine dye or a cyanine-like dye.

As used herein, the phrase "cyanine-like structure" describes a molecule that has two nitrogen-containing moieties which are joined by a polymethine-containing chain (e.g., a carbomethine chain). One or both nitrogens can be a part of a nitrogen-containing heteroaromatic moiety, or, alternatively, be a secondary or tertiary ammonium.

In some embodiments, the polymethine-containing chain comprises 2 carbon atoms and the cyanine-like structure is of a Cy2 type cyanine structure, as this term is widely recognized in the art.

In some embodiments, the carbomethine-containing chain comprises 3 carbon atoms and the cyanine-like structure is of a Cy3 type cyanine structure.

In some embodiments, the carbomethine-containing chain comprises 5 carbon atoms and the cyanine-like structure is of a Cy5 type cyanine structure.

In some embodiments, the carbomethine-containing chain comprises 7 carbon atoms and the cyanine-like structure is of a Cy7 type cyanine structure.

In some embodiments, the carbomethine-containing chain comprises 5 or 7 carbon atoms.

Thus, in some embodiments, the fluorogenic moiety as described herein is a modified cyanine dye, including any of the known cyanine dyes, which is modified by the means used to attach it to the polymeric backbone.

In some embodiments, a cyanine-like fluorogenic moiety as described herein can be regarded as comprising the same basic chemical arrangement as cyanine dyes, yet, because of its attachment to the polymeric backbone in sufficient amount and in close proximity, the fluorogenic moiety is spectroscopically silenced in the NIR range before activation by said cleavage, due to self-quenching.

In some embodiments, a cyanine-like fluorogenic moiety as described herein can be regarded as comprising the same basic chemical arrangement as cyanine dyes, yet, because of its attachment to the polymeric backbone in close proximity to a quenching agent, the fluorogenic moiety is spectroscopically silenced in the NIR range before activation by said cleavage, due to quenching.

In some embodiments, a cyanine-like fluorogenic moiety as described herein has a chemical arrangement which is different from cyanine dyes (e.g., a delocalized $\pi$-electrons system), and hence the fluorogenic moiety is spectroscopically silenced in the NIR range before activation by said cleavage.

Fluorogenic moieties which have a modified cyanine structure are also referred to herein as cyanine-based fluorogenic moieties, and the fluorescent moieties or compounds generated upon said cleavage are referred to herein as cyanine dyes. Exemplary such moieties are described in further detail hereinafter.

Other fluorogenic or fluorescent moieties are also contemplated.

In embodiments of the present invention where the fluorogenic moiety comprises a fluorescent moiety or compound attached to the cleavable linker or moiety, the fluorescent moiety can be selected from the myriad of known fluorescent moieties. FITC is a non-limiting example. Other examples are listed in "Methods in Molecular Biology, vol. 335: Fluorescent Energy Transfer Nucleic Acid Probes: Designs and Protocols", Edited by: V. V. Didenko © Humana Press Inc., Totowa, N.J., Chapter 2, page 17, by Mary Katherine Johans son, which is incorporated by reference as if fully set forth herein.

The Quenching Agent:

Herein, the phrase "quenching agent" is also referred to interchangeably as "quencher", and describes a moiety or compound which is capable of decreasing the fluorescence intensity of another moiety or compound, as described herein. The decrease in fluorescence intensity by quenching can result from processes such as excited state reactions, energy transfer, complex-formation and the like.

A quencher is selected in accordance with a selected fluorescent moiety or compound, namely, as capable of, for example, absorbing energy emitted from the fluorescent moiety or compound, interacting with the fluorescent moiety or compound which it is in its excited state, etc.

In some of any of the embodiments described herein, the quencher is selected suitable for FRET, which is based on dipole-dipole interactions between the transition dipoles of the fluorescent moiety (which acts as a donor) and the quencher (which acts as an acceptor). A suitable quencher should be positioned at a distance of distances up to 100 Å from the donor, should have a suitable orientation of the dipole moment relative to the donor, and should have a spectral overlap with the donor.

Those skilled in the art would readily recognize which quenching agent or dye is suitable for use for quenching the fluorescence of a selected fluorescent moiety or moiety.

Exemplary quenching agent-fluorescent moiety pairs include, but are not limited to, two cyanine dyes (which can be the same, for SQ, or different, for pair FRET) (NIR), FITC and DR1 (visible), Fluorescein & Cy5 (visible), Cy5 & IR783 (NIR), Cy7 & IR783 (NIR), Cy3 & BHQ2 (visible), Cy5 & BHQ2 (NIR). Additional pairs are listed in "Methods in Molecular Biology, vol. 335: Fluorescent Energy Transfer Nucleic Acid Probes: Designs and Protocols", Edited by: V. V. Didenko © Humana Press Inc., Totowa, N.J., Chapter 2, page 17, by Mary Katherine Johansson, which is incorporated by reference as if fully set forth herein.

The Linking Moiety:

Herein throughout, the phrase "linking moiety" is also referred to herein as "linker".

In any of the embodiments described herein, the fluorogenic moiety is attached to the polymeric backbone (to at least a portion of the backbone units composing the first polymeric backbone), via a linking moiety, which is a cleavable linking moiety (referred to herein as a first cleavable linking moiety).

In some of any of the embodiments described herein, the therapeutically active agent is attached to a polymeric backbone (e.g., to at least a portion of the first or second polymeric backbone) via a linking moiety, preferably, a cleavable linking moiety, referred to herein as a second cleavable linking moiety. The linker linking the therapeutically active agent to the polymeric backbone, if present, and the linker linking the fluorogenic moiety to the polymeric backbone may be the same or different. In some embodiments, the linker is the same and in some embodiments, the linker or either the same or is cleavable under the same conditions (e.g., by the same enzyme).

The linker described herein refers to a chemical moiety that serves to couple the fluorogenic moiety and/or the therapeutically active agent to the polymeric backbone (to the respective portion of backbone units).

The phrase "cleavable linking moiety" or "cleavable linker" describes a chemical moiety which can undergo a bond cleavage upon a chemical event, as described herein.

In some embodiments, the linker is a biodegradable or biocleavable linker.

The phrases "biodegradable linker" and "biocleavable linker" as used herein, describe a linker that is capable of being degraded, or cleaved (undergo bond cleavage), when exposed to certain physiological conditions. Such physiological conditions can be, for example, pH, a presence of a certain enzyme, a presence of chemical substance (e.g., analyte) and the like.

In some embodiments, the linker is designed as being cleavable at conditions characterizing the desired bodily site (e.g., by certain enzymes, chemical substances or pH), as detailed hereinbelow.

According to some embodiments, the biodegradable linker is a pH-sensitive linker, a hydrolysable linker or an enzymatically-cleavable linker.

In some embodiments, the linker is capable of being cleaved by pre-selected cellular enzymes, for instance, those found in osteoblasts, osteoclasts, lysosomes of cancerous cells or proliferating endothelial cells, or in tumor tissues.

Alternatively, an acid hydrolysable linker could comprise an ester or amide linkage.

In some embodiments the biodegradable linker is an enzymatically cleavable linker. Such a linker is typically designed so as to include a chemical moiety, typically, but not exclusively, an amino acid sequence that is recognized by a pre-selected enzyme. Such an amino acid sequence is often referred to in the art as a "recognition motif". A polymeric conjugate comprising such a linker typically remains substantially intact in the absence of the pre-selected enzyme in its environment, and hence does not cleave or degrade so as to the release the moiety attached thereto via the linker until contacted with the enzyme.

In some embodiments, the enzymatically cleavable linker is cleaved by an enzyme which is overexpressed in tumor tissues. A polymeric conjugate comprising such a linker ensures, for example, that a substantial amount of a conjugated moiety is released from the conjugate only at the tumor tissue.

Exemplary such enzymes include, but are not limited to, Cathepsins (cysteine proteases) such as Cathepsin B, Cathepsin K, Cathepsin D, Cathepsin H, Cathepsin L, and Cathepsin S, legumain, matrix metalloproteinases such as MMP-2 and MMP-9, as well as MMP1, MMP3, MMP7, MMP13 and MMP14, KLK6 (kallikrein-related peptidase-6 which encodes a trypsin-like serine peptidase), PIM serine/threonine kinases such as PIM 1, PIM 2 and PIM 3, histone deacetylases (HDAC) such as HDAC1, HDAC2, HDAC3, HDAC6 AND kdac8.

Suitable linking moieties having a Cathepsin K cleavable site include amino acid sequences such as, but not limited to, -[Asn-Glu-Val-Ala]- and -[Lys-Lys]-. Suitable linking moieties having cathepsin-B cleavable sites include amino acid sequences such as, but not limited to, -[Gly-Phe-Lys]-, -[Cit-Val]-, -[Arg]-, -[Arg-Arg]-, -[Val-Arg]-, -[Phe-Lys]-, -[Phe-Arg]-, [Gly-Phe-Leu-Gly], -[Gly-Phe-Ala-Leu]- and -[Ala-Leu-Ala-Leu]-, -[Gly-Leu-Gly]-, -[Gly-Phe-Gly]-, -[Gly-Phe-Leu-Gly-Phe-Lys]-, -[(Glu)$_6$-(Asp)$_8$]- and combinations thereof.

In some embodiments the linking moiety comprises the amino acid sequences -[Gly-Phe-Lys]-, -[Gly-Leu-Gly]-, -[Gly-Phe-Gly]-, -[Gly-Leu-Phe-Gly]-, -[Gly-Phe-Leu- Gly]-, -[Phe-Lys]- and -[Gly-Phe-Leu-Gly-Phe-Lys]-. In some embodiments, the trigger unit consists of these amino acid sequences or a combination thereof.

Suitable linking moieties having cathepsin-D cleavable sites include an amino acid sequence such as, but are not limited to, -[Gly-Pro-Ile-Cys(Et)-Phe-Phe-Arg-Leu]-.

Suitable linking moieties having cathepsin-K cleavable sites include an amino acid sequence such as, but are not limited to, -[Gly-Gly-Pro-Nle]-.

Suitable linking moieties having cathepsin-L cleavable sites include an amino acid sequence such as, but are not limited to, -[Phe-Arg]-.

Suitable linking moieties having Legumain cleavable sites include an amino acid sequence such as, but are not limited to, -[Ala-Ala-Asn]-, -[Asn-Glu-Val-Ala]- and -[(Glu)$_6$-(Asp)$_8$]-, and any combination thereof.

Suitable linking moieties having MMP cleavable sites include an amino acid sequence such as, but are not limited to, -[Cys-Gly-Leu-Asp-Asp]-, -[Gly-Pro-Leu-Gly-Val]-, -[Gly-Pro-Leu-Gly-Ala-Gly]-, -[Cys-Asp-Gly-Arg]-, -[Gly-Pro-Leu-Gly-Val-Arg-Gly-Cys]- and -[Pro-Leu-Gly-Met-Thr-Ser]-, and any combination thereof. In some embodiments, the linking moieties have only a part of the above-described amino acid sequences. In some embodiments, the linking moiety consists of 3 amino acids of the above-described sequences.

Suitable linking moieties having MMP-2 and MMP-9 cleavable sites include an amino acid sequence such as, but are not limited to, -[Gly-Pro-Gln-Gly-Ile-Ala-Gly-Gln]-, -[Gly-Pro-Leu-Gly-Ile-Ala-Gly-Gln]-, -[Gly-Pro-Gln-Gly-Ile-Trp-Gly-Gln]-, -[Pro-Leu-Gly-Val-Arg]-, [Pro-Leu-Gly-Leu-Tyr-Leu]-, -[Pro-Leu-Gly-Leu-Tyr-Ala-Leu]-, -[Gly-Pro-Leu-Gly-Ile-Ala-Gly-Gln]-, -[Gly-Pro-Leu-Gly-Leu-Trp-Ala-Gln]-, -[Gly-Pro-Leu-Gly-Val-Arg-Gly-Lys]-, -[His-Pro-Val-Gly-Leu-Leu-Ala-Arg]-, -[Gly-Gly-Pro-Leu-Gly-Leu-Trp-Ala-Gly-Gly]-, -[Ala-Ala-Ala-Pro-Leu-Gly-Leu-Trp-Ala]- and combinations thereof. In some embodiments, the linking moieties have only a part of the above-described amino acid sequences. In some embodiments, the linking moiety consists of 3 amino acids of the above-described sequences.

Suitable linking moieties having MMP-7 cleavable sites include an amino acid sequence such as, but are not limited to, -[Gly-Val-Pro-Leu-Ser-Leu-Thr-Met-Gly-Cys]- and -[Arg-Pro-Leu-Ala-Leu-Trp-Arg-Ser]- and combinations thereof. In some embodiments, the linking moieties have only a part of the above-described amino acid sequences. In some embodiments, the linking moiety consists of 3 amino acids of the above-described sequences.

Suitable linking moieties having MMP-13 cleavable sites include an amino acid sequence such as, but are not limited to, -[Gly-Pro-Leu-Gly-Met-Arg-Gly-Leu-Gly-Lys]-. In some embodiments, the linking moieties have only a part of the above-described amino acid sequence. In some embodiments, the linking moiety consists of 3 amino acids of the above-described sequence.

Suitable linking moieties having KLK6 cleavable sites include amino acid sequences such as, but are not limited to, -[Gly-Ala-Arg-Arg-Arg-Gly]-, -[Trp-Ala-Arg-Arg-Ser]-, -[Trp-Ala-Arg-Lys-Arg]-, -[Les-Arg-Lys-Arg-Trp]-, -[Ala-Lys-Arg-Arg-Gly]-, abd -[Trp-Lys-Lys-Lys-Arg]. In some embodiments, the linking moieties have only a part of the above-described amino acid sequences. In some embodiments, the linking moiety consists of 3 amino acids of the above-described sequences.

Suitable linking moieties having PIM cleavable sites include an amino acid sequence such as, but are not limited to, -[(Arg/Lys)$_3$-AA$_1$-[Ser/Thr-AA$_2$]-, with AA$_1$ and AA$_2$ being independently any amino acid residue except basic or large hydrophobic residues. An exemplary amino acid sequence include: -[Ala-Arg-Lys-Arg-Arg-Arg-His-Pro-Ser-Gly-Pro-Pro-Thr-Ala]-.

Suitable linking moieties having HDAC cleavable sites include acetylated Lysine.

Suitable linking moieties having caspase cleavable sites include an amino acid sequence such as, but not limited to, -[Asn-Glu-Val-Ala]-, -[(Glu)$_6$-(Asp)$_8$]-, -[Asp-Glu-Val-Asp]-, and [Asp-Glu-Val-Asp-Ala-Pro-Lys]-.

In some embodiments, the linker is a Cathepsin B-cleavable linker.

Cathepsin B is a lysosomal enzyme over-expressed in both epithelial and endothelial tumor cells. Suitable exemplary linkers having cathepsin-B cleavable sites include amino acid sequences such as, but are not limited to, -[Gly-Phe-Leu-Gly]-, -[Gly-Phe-Ala-Leu]-, -[Ala-Leu-Ala-Leu]-, -[Gly-Leu-Gly]-, -[Gly-Phe-Gly]-, -[Gly-Phe-Leu-Gly-Phe-Lys]-, -[Cit-Val]-, -[Arg]-, -[Arg-Arg]-, -[Phe-Lys]-, -[Val-Arg]-, -[Phe-Arg]-, -[6-Glu-8-Asp]-, and any combination thereof.

In some embodiments the enzymatically cleavable linker is cleaved by cathepsin K.

Cathepsin K is a lysosomal cysteine protease involved in bone remodeling and resorption and is predominantly expressed in osteoclasts. Its expression is stimulated by inflammatory cytokines that are released after tissue injury and in bone neoplasms [Pan et al. 2006, J Drug Target 14:425-435; Husmann et al. 2008, Mol Carcinog 47: 66-73; Segal et al. PLoS One 2009, 4(4):e5233].

A non-limiting example of a linker having cathepsin K cleavable sites is -[Gly-Gly-Pro-Nle]-.

In some embodiments the linker comprises the amino acid sequences -[Gly-Leu-Gly]-, -[Gly-Phe-Gly]-, -[Gly-Leu-Phe-Gly]-, -[Gly-Phe-Leu-Gly]-, -[Phe-Lys]-, -[Gly-Phe-Leu-Gly-Phe-Lys]- and -[Gly-Gly-Pro-Nle]-. In some embodiments, the linker consists of these amino acid sequences or a combination thereof.

Other suitable linkers include, but are not limited to, alkyl chains; alkyl chains optionally substituted with one or more substituents and in which one or more carbon atoms are optionally interrupted by nitrogen, oxygen and/or sulfur heteroatom.

Other suitable linkers include amino acids and/or oligopeptides.

Such alkyl chains and/or oligopeptides can optionally be functionalized so as allow their covalent binding to the moieties linked thereby (e.g., the polymeric backbone units and the fluorogenic moiety, the polymeric backbone units and the therapeutically active agent). Such a functionalization may include incorporation or generation of reactive groups that participate in such covalent bindings, as detailed hereinunder.

In some embodiment, the linker is a biodegradable oligopeptide which contains, for example, from 2 to 10 amino acid residues.

An oligopeptide linker which contains the pre-selected amino acid sequence (recognition motif) can also be constructed such that the recognition motif is repeated several times within the linker, to thereby enhance the selective release of the attached agent or moiety. Various recognition motifs of the same or different enzymes can also be incorporated within the linker.

Similarly, the linker may comprise multiple pH sensitive bonds or moieties. Linkers comprising such multiple cleavable sites can enhance the selective release of the therapeutically active agent at the desired bodily site, thereby reducing adverse side effects, and further enhance the relative concentration of the released drug at the bodily site when it exhibits its activity.

In some embodiments of the present invention, the fluorogenic moiety and/or the therapeutically active agent(s) is/are bound directly to the polymeric backbone units, whereby the bond linking these moieties to the polymeric backbone is biodegradable, for example, a hydrolysable bond, an enzymatically-cleavable bond or a pH-sensitive bond. Such a bond can be formed upon functionalizing the polymeric backbone units, the fluorogenic moiety and/or the therapeutically active agent, so as to include compatible reactive groups, as defined herein, for forming the required bond. Such a bond is also referred to herein as a cleavable or biocleavable linker.

According to some embodiments, the biodegradable linker is a pH-sensitive linker or an enzymatically-cleavable linker.

A pH-sensitive linker comprises a chemical moiety that is cleaved or degraded only when subjected to a certain pH condition, such as acidic pH (e.g., lower than 7), neutral pH (6.5-7) or basic pH (higher than 7).

Such a linker may, for example, be designed to undergo hydrolysis under acidic or basic conditions, and thus, the conjugate remains intact and does not release the agents or moieties attached to the polymeric backbone in the body, until it reaches a physiological environment where a pH is either acidic or basic, respectively.

Exemplary pH-sensitive linkers include, but are not limited to, a hydrazone bond, ester (including orthoester) bond, amide bond of cis-aconytil residue, a trityl group, acetals, ketals, Gly-ester and a -[Gly-Phe-Gly]-moiety.

The peptide linker may also include a peptide sequence which serves to increase the length of the linker. Longer peptides may be advantageous due to a more efficient steric interaction of the linker with the cleaving enzyme due to enhanced accessibility.

In some embodiments, the linker is -[Gly-Phe-Leu-Gly-Phe-Lys]-. Such a linker comprises two "recognition motifs" of Cathepsin B, and a cleavage thereof so as to release the moiety attached thereto is effected only in the presence of high enzyme concentration. This feature enhances the selective release of the attached moiety at a site where the enzyme is over-expressed.

In some embodiments, the linker is -[Gly-Phe-Leu-Gly]-.

In some embodiments, the linker is or comprises -[Phe-Lys]-.

In some of any of the embodiments described herein, the first and second cleavable linking moieties, if present, are the same or are cleavable by the same chemical event.

A Spacer:

In some of any of the embodiments described herein, the fluorogenic moiety is attached to the first cleavable linker via a spacer.

In some of any of the embodiments described herein the first cleavable linker is attached to the respective backbone units via a spacer.

In some of any of the embodiments described herein, the therapeutically active agent is linked to the respective polymeric backbone units and/or to the second cleavable linker via a spacer. The spacers can be the same or different.

In some of the embodiments described herein, the quenching agent, if present, is linked to the respective polymeric backbone units via a spacer.

In some of the embodiments described herein, when the quenching agent forms a part of the fluorogenic moiety, it is linked to the fluorescent moiety via a spacer.

In some of the embodiments described herein, when the therapeutically active agent forms a part of the fluorogenic moiety, it is linked to the fluorescent moiety via a spacer.

The term "spacer" as used herein describes a chemical moiety that is covalently attached to, and interposed between, two other moieties, or a moiety/agent and a polymeric backbone unit, thereby forming a bridge-like.

In some cases, a spacer is utilized for enabling a more efficient and simpler attachment of the fluorogenic moiety and/or therapeutically active agent and/or quenching agent to the polymeric backbone units or linker or to one another, in terms of steric considerations (e.g., renders the site of the polymeric backbone to which coupling is effected less hindered) or chemical reactivity considerations (adds a compatible reactive group to facilitate coupling). In some cases, the spacer may contribute to the performance of the resulting polymeric conjugate. For example, the spacer may render an enzymatically cleavable linker less sterically hindered and hence more susceptible to enzymatic interactions.

In some embodiments, the spacer facilitates the attachment of the moiety or agent to the polymeric backbone units or the linker. This may be effected by imparting a reactive group to the moiety to be attached, which is chemically compatible with functional groups in the polymeric backbone units and/or the linker attached to the polymeric backbone, and/or by modifying the solubility of the moiety to be attached to the polymer, so as to facilitate the reaction between the polymer (or co-polymer) and the moiety.

Suitable spacers include, but are not limited to, alkylene chains, optionally substituted by one or more substituents and which are optionally interrupted by one or more nitrogen, oxygen and/or sulfur heteroatom.

Other suitable spacers include amino acids and amino acid sequences, optionally functionalized with one or more reactive groups for being coupled to the respective portion or moiety of the polymeric conjugate.

In some embodiments, a spacer has the formula G-(CH$_2$)n-K, wherein n is an integer from 1 to 10; and G and K are each a reactive group such as, for example, NH, O or S. In some embodiments, G and K are each NH and n is 2.

An exemplary spacer is —[NH—(CH$_2$)$_m$NH$_2$]— wherein "m" stands for an integer ranging from 1-10. Preferably m is 2.

In some embodiments, the spacer is or comprises an amino acid sequence, optionally an inert amino acid sequence (namely, does not affect the affinity or selectivity of the polymeric conjugate). Such a spacer can be utilized for elongating or functionalizing the linker.

Exemplary such sequences include, for example, -[Gly-Gly-].

In some embodiments, the spacer is a degradable spacer, which is capable of undergoing degradation reactions so as to release an agent attached thereto. In some embodiments, the spacer is biodegradable, as defined herein.

In some embodiments the spacer is a substituted or unsubstituted aryl group and substituted or unsubstituted heteroaryl group whereby the substituents can be carbonate, C-amido, N-amido and amine, whereby the spacer may be linked to the desired agent or moiety or to the polymeric backbone units either directly, through the aromatic group or alternatively, via one or more of the substituents.

In some embodiments, the spacer is a degradable spacer selected such that it undergoes a spontaneous degradation once it is cleaved from the polymeric conjugate. Such spacers are also referred to herein as self-immolative spacers.

Such a spacer can be, for example, attached to a biodegradable linker at one end and to another moiety or agent (e.g., the fluorogenic moiety) at another end, such that once the biodegradable linker is cleaved, so as to release the spacer and the moiety attached thereto, the spacer undergoes a spontaneous degradation so as to release the moiety attached thereto.

Exemplary spacers that can undergo such a spontaneous degradation include, but are not limited, chemical moieties that can undergo a spontaneous 1,4-, 1,6-, 1,8-, etc. elimination, via a cascade of immolative electronic reactions. Such chemical groups are known in the art, or, otherwise, can be devised by those skilled in the art.

In an exemplary embodiment, the spacer is such that can undergo a spontaneous 1,6-benzyl elimination. An example of such a spacer is p-aminobenzyl carbonate (PABC).

In some embodiments, the spacer comprises one or more of the exemplary spacers described herein.

In some embodiments, a spacer is used to connect 3 moieties to one another, or to connect 2 moieties to a cleavable linking moiety or to respective polymeric backbones.

For example, a spacer can connect a fluorescent moiety and a quenching agent and/or a therapeutically active agent to one another, so as to form a fluorogenic moiety, and to connect the fluorogenic moiety to a cleavable linking moiety. Such a spacer can include a bi- or tri-functional moiety (e.g., an aryl moiety as described herein), which is also referred to herein as a branching spacer. Such a spacer can combine also spacers which are attached to the branching spacer, and connect the moieties/agents to the branching spacer unit.

Exemplary such multi-functional spacers are shown, for example, in FIGS. 31A-B, 34, 35, 39 and 42.

The spacer may be varied in length and in composition. A spacer as defined herein encompasses also any combination of the spacers described herein.

The following describes exemplary polymeric conjugates and polymeric systems comprising same according to some embodiments of the present invention.

The First Polymeric Moiety:

According to an aspect of some embodiments of the present invention there is provided a polymeric conjugate, also referred to herein as a first polymeric moiety or a first polymeric conjugate, which comprises a (first) polymeric backbone composed of a plurality of backbone units and having attached to at least a portion of the backbone units a fluorogenic moiety, as described herein, the fluorogenic moiety being attached to the portion of backbone units via a cleavable linking moiety such that upon cleavage of the linking moiety, a fluorescent signal is generated (e.g., upon release and/or generation of a fluorescent moiety).

According to some embodiments of this aspect of the invention, the fluorescent moiety emits near infrared light.

According to some embodiments of this aspect of the invention, the fluorescent moiety is a cyanine dye.

According to some of any of the embodiments of the invention, the first cleavable linking moiety is a first biocleavable linking moiety, as described herein.

In some of any of the embodiments described herein, the fluorogenic moiety is such that when it is attached to the polymeric backbone via the first cleavable linking moiety, it does not emit light, whereby when the first linking moiety is cleaved, the generated fluorescent moiety emits light (e.g., near infrared light), thus featuring a Turn-ON mechanism, as described herein.

According to some of any of the embodiments described herein, the fluorogenic moiety is attached to the cleavable linking moiety via a spacer, as described in any of the respective embodiments.

According to some embodiments, the spacer is selected degradable such that it allows releasing or generating the fluorescent moiety, as described herein, upon cleavage of the linking moiety.

According to some embodiments, the spacer is selected degradable such that it allows generating the fluorescent signal upon cleavage of the linking moiety.

Spacers usable in the context of a fluorogenic moiety can be selected to act via ICT or FRET mechanism, as described herein.

In some of any of the embodiments described herein, the first polymeric moiety further comprises a quenching agent, either attached to one or more polymeric backbone units of the first polymeric backbone or forming a part of the fluorogenic moiety, as described herein.

In some of any of the embodiments described herein, the fluorogenic moiety is a fluorescent moiety, which is attached directly or via a spacer (e.g., a degradable or self-immolative spacer as described herein) to the cleavable linking moiety.

In some of any of the embodiments described herein, the first polymeric moiety is a homo-FRET system, and is devoid of a quenching agent.

In some of these embodiments, a loading of the fluorescent moiety is such that allows self-quenching, namely, the loading results in a distance between the fluorescent moieties attached to the backbone units which is up to 100 angstroms.

In some of these embodiments, the loading of the fluorescent moiety is at least 1 mol %, preferably at least 2 mol %, at least 3 mol % or at least 4 mol % and/or ranges from 1 to 10 mol %.

In some of any of the embodiments described herein, the first polymeric moiety is a pair-FRET system, which further comprises a quenching agent, as described herein.

In some of these embodiments, the quenching agent is attached to the respective backbone units via a spacer, for example, a non-degradable spacer, such as, for a non-limiting example, a spacer that comprises a -[Gly-Gly]- moiety.

In some of any of the embodiments described herein, the quenching agent is attached to a terminal backbone unit of the polymeric backbone. In some of these embodiments, the polymeric backbone is functionalized or is designed so as to feature a reactive group, or a spacer featuring a reactive group, for attaching the quenching agent. An exemplary such group can be generated while synthesizing a HPMA copolymer by RAFT polymerization, as exemplified in the Examples section that follows.

A first polymeric moiety as described herein can be represented by Formula IA:

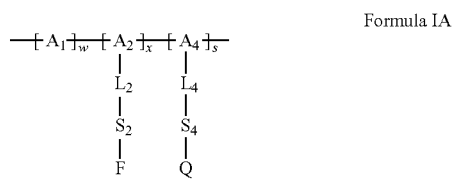

Formula IA wherein:

$A_1$, $A_2$ and $A_4$ are polymeric backbone units as described herein;

$L_2$ is the first cleavable lining moiety, as described herein, $S_2$ is a first spacer, linking the fluorogenic moiety to $L_2$, as described herein, or is absent;

$L_4$ is a third linking moiety, linking the quenching agent to the backbone units, and which can be cleavable or non-cleavable, or is absent;

$S_4$ is a third spacer linking the quenching agent to the linking moiety, or is absent;

F is a fluorogenic moiety as described in any one of the respective embodiments herein;

Q is a quenching agent as described in any one of the respective embodiments herein;

w is an integer having a value such that w/(x+s+w) multiplied by 100 is in the range of from 0 to 99.9;

x is an integer having a value such that x/(x+s+w) multiplied by 100 is in the range of from 0.1 to 100; and s is an integer having a value such that s/(x+s+w) multiplied by 100 is in the range of from 0 to 99.9.

Each [$A_2$-$L_2$-$S_2$-F] independently represents a backbone unit having attached thereto the fluorogenic moiety; and Each [$A_4$-$L_4$-$S_4$-Q] independently represents a backbone unit having attached thereto the quenching agent.

Optionally, the polymeric moiety further comprises backbone units -[$A_5$]z- as described herein, wherein z is an integer having a value such that z/(x+s+w+z) multiplied by 100 is in the range of from 0 to 99.9.

When z is other than 0, w, x and s in Formula I are divided by "x+w+z+s" instead of "x+s+w".

In some of any of the embodiments described herein:

w is an integer having a value such that w/(x+s+w) multiplied by 100 is in the range of from 0.1 to 99.9, or from 10 to 99.9, or from 20 to 99.9, or from 30 to 999, or from 40 to 99.9, or from 50 to 99.9, or from 60 to 99.9, or from 70 to 99.9, or as further described herein;

x is an integer having a value such that x/(x+s+w) multiplied by 100 is in the range of from 0.1 to 99.9, or from 0.1 to 20, or from 0.1 to 15, or from 1 to 15, or from 2 to 15, or from 3 to 15 or from 4 to 15, as is further described herein; and s is an integer having a value such that s/(x+s+w) multiplied by 100 is in the range of from 0 to 100, or from 0 to 20, or from 0 to 15, or from 0 to 1, as is further described herein.

In some embodiments, s is 0, and the polymeric moiety is a homo-FRET system, as described herein.

In some embodiments, s is a positive integer and is such that a single molecule of a quenching agent is attached to the polymeric backbone. In some of these embodiments, $A_4$ is a terminal backbone unit in the polymeric backbone.

In some embodiments, s is a positive integer and is in a ratio to x which is in a range of from 20:1 to 1:20, or from 10:1:10, or from 5:1 to 1:5, or from 2:1 to 1:2, or is 1:1, including any subratios therebetween.

In some of these embodiments, each of the backbone units $A_1$, $A_2$ and $A_4$ can be a terminal unit, attached to one other unit, or is attached to two other units, which can be the same of different.

In some of any of the embodiments described herein, the fluorogenic moiety is, or comprises a fluorescent moiety, as described herein.

The fluorescent moiety is also referred to herein as F*.

In some of any of the embodiments described herein, the fluorogenic moiety is, or comprises a fluorescent moiety which is, or comprises, a cyanine dye, or a cyanine-like moiety, as described herein.

In cyanine-like dye molecules, one nitrogen is positively charged (e.g., in a form of an ammonium ion) and one nitrogen atom is neutral (e.g., in a form of an amine) and thus has a lone pair of electrons. The positive charge in cyanine-like dyes therefore resonates between the two nitrogen atoms via the polymethine chain.

In some of these embodiments, the fluorogenic moiety is represented by, or comprises a moiety represented by, formula II:

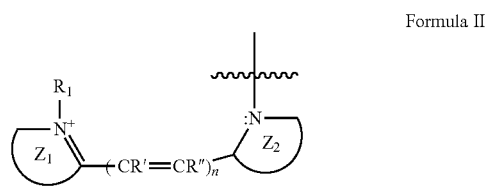

Formula II wherein:

$Z_1$ and $Z_2$ are each independently a substituted or unsubstituted heterocylic moiety;

$R_1$ is hydrogen, a substituted or unsubstituted alkyl or a substituted or unsubstituted cycloalkyl;

n is an integer of from 1 to 10; and

R' and R" are each independently hydrogen, a substituted or unsubstituted alkyl and a substituted or unsubstituted cycloalkyl, or, alternatively, R' and R" form together an aryl.

In cyanine-like fluorescent moiety, two heterocylic moieties are linked therebetween via a substituted or unsubstituted polymethine chain, such that one heterocylic moiety acts as a donor moiety ($Z_2$) and one acts as an acceptor moiety ($Z_1$).

The phrase "polymethine chain" describes a chain of methine groups (e.g., —CH=CH— groups) each can independently be substituted, as long as the substituent does not interfere with the optical properties of the disclosed moiety, as defined herein.

The polymethine-containing moiety forms a chain that can comprise from 2 to 13 carbon atoms, preferably from 2 to 7 carbon atoms.

Exemplary heterocyclic moieties suitable for inclusion in the fluorogenic compounds disclosed herein as donor moieties include, but are not limited to, imidazoline ring, imidazole ring, benzimidazole ring, α-naphthoimidazole ring, β-naphthoimidazole ring, indole ring, isoindole ring, indolenine ring, isoindolenine ring, benzindolenine ring, pyridinoindolenine ring, oxazoline ring, oxazole ring, isoxazole ring, benzoxazole ring, pyridinooxazole ring, α-naphthoxazole ring, β-naphthoxazole ring, selenazoline ring, selenazole ring, benzoselenazole ring, α-naphthselenazole ring, β-naphthselenazole ring, thiazoline ring, thiazole ring, isothiazole ring, benzothiazole ring, α-naphthothiazole ring, β-naphthothiazole ring, tellulazoline ring, tellulazole ring, benzotellulazole ring, α-naphthotellulazole ring, β-naphthotellulazole ring, isoquinoline ring, isopyrrole ring, imidaquinoxaline ring, indandione ring, indazole ring, indoline ring, oxadiazole ring, carbazole ring, xanthene ring, quinazoline ring, quinoxaline ring, thiodiazole ring, thiooxazolidone ring, tetrazole ring, triazine ring, naphthyridine ring, piperazine ring, pyrazine ring, pyrazole ring, pyrazoline ring, pyrazolidine ring, pyrozolone ring, pyridine ring, pyridazine ring, pyrimidine ring, pyrylium ring, pyrrolidine ring, pyrroline ring, pyrrole ring, phenazine ring, phenanthridine ring, phthalazine ring, furazan ring, benzoxazine ring, morpholine ring, and rhodanine ring.

Acceptor moieties can be an ammonium form of any of the foregoing.

In some embodiments, $Z_1$ and $Z_2$ are each independently a substituted or unsubstituted heteroaryl, whereby the acceptor moiety is positively charged.

In some embodiments, one of acceptor and donor moieties comprises a pyridine ring and the other is an indolenine ring, as defined herein.

In some embodiments, the donor moiety is an indolenine ring, and the acceptor moiety is an ammonium form thereof.

The phrase "indolenine ring" describes a ring having an aromatic portion having fused thereto a 5-membered aromatic.

In some embodiments, the fluorogenic moiety is, or comprises, a moiety represented by Formula IIA:

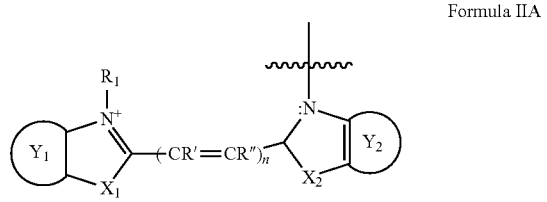

Formula IIA wherein:

$Y_1$ and $Y_2$ are each independently a substituted or unsubstituted aromatic moiety; and $X_1$ and $X_2$ are each independently selected from the group consisting of $CR_3R_4$, $NR_3$, and S, wherein $R_3$ and $R_4$ are each independently selected from the group consisting of hydrogen, alkyl, cycloalkyl, aryl, heteroalicyclic, heteroaryl, alkoxy, hydroxy, thiohydroxy, thioalkoxy, aryloxy, thioaryloxy, amino, nitro, halo, trihalomethyl, cyano, amide, carboxy, sulfonyl, sulfoxy, sulfinyl, sulfonamide, and a saccharide.

Whenever the carbon, nitrogen or sulfur representing X in the above formula, are substituted, the substituents can be independently an alkyl, cycloalkyl, alkyl, cycloalkyl, aryl, heteroalicyclic, heteroaryl, alkoxy, hydroxy, thiohydroxy, thioalkoxy, aryloxy, thioaryloxy, amino, nitro, halo, trihalomethyl, cyano, amide, carboxy, sulfonyl, sulfoxy, sulfinyl, sulfonamide, and a saccharide.

In some embodiments, $Y_1$ and $Y_2$ are each a substituted or unsubstituted phenyl.

In some embodiments, $X_1$ and $X_2$ are each independently $CR_3R_4$.

In some embodiments, $R_3$ and $R_4$ are each an alkyl.

In some embodiments, $R_1$ is hydrogen or alkyl.

In some embodiments, the fluorogenic moiety is represented by, or comprises, a moiety represented by, Formula IIB:

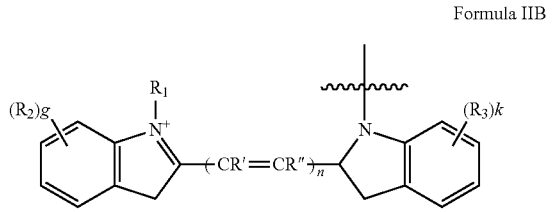

Formula IIB wherein:

g and k are each independently an integer of from 0 to 5; and $R_2$ and $R_3$ are each independently selected from the group consisting of hydrogen, alkyl, cycloalkyl, aryl, heteroalicyclic, heteroaryl, alkoxy, hydroxy, thiohydroxy, thioalkoxy, aryloxy, thioaryloxy, amino, nitro, halo, trihalomethyl, cyano, amide, carboxy, sulfonyl, sulfoxy, sulfinyl, sulfonamide, and a saccharide.

In some embodiments, $R_1$ is hydrogen or a substituted or unsubstituted alkyl.

In some embodiments, one or both $R_2$ and $R_3$ is an alkyl substituted by a sulfonyl or sulfinyl.

It is to be noted that fluorogenic compounds in which one or more of the indolenine-like rings is replaced by any of the acceptor or donor moieties described herein, for example, any of the ammonium acceptor moieties described herein (e.g., a pyridinium moiety), are also contemplated.

In some of any of the embodiments described herein, the quenching agent forms a part of the fluorogenic moiety.

In some of these embodiments, s is 0.

In some embodiments, a FRET-based modular system is used as a fluorogenic moiety, in which both the fluorescent moiety and the quenching agent are linked to one another, and/or to the first cleavable linking moiety.

In some embodiments, such a system can be generally represented, according to some embodiments of the invention, by formulae III or III*:

Formula III

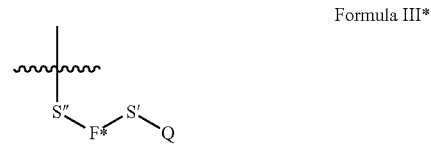

Formula III* wherein F* is a fluorescent moiety, as described herein; Q is the quenching agent;

S' and S''' (if present) are each independently a spacer, preferably one or more of which is degradable, or absent; and S'' is a multifunctional spacer, as described herein, for example, a self-immolative spacer, which connects the fluorogenic moiety to the first cleavable moiety, or to an additional spacer which is connected to the cleavable linking moiety.

In some embodiments, at least S'' in Formula III is a degradable spacer, e.g., a self-immolative spacer, as described herein, which, upon cleavage of the linking moiety, degrades so as to no longer have the quenching agent linked to the fluorescent moiety. As a result, a fluorescent signal is generated.

In some embodiments, at least S'' and S' in Formula III* is a degradable spacer, e.g., a self-immolative spacer, as described herein, which, upon cleavage of the linking moiety, degrades so as to no longer have the fluorescent moiety linked to the quenching agent and to the polymeric moiety. As a result, a fluorescent signal is generated.

In some of any of the embodiments described herein, the fluorescent moiety is a cyanine-like structure or moiety, as described herein, and the fluorogenic moiety can represented by one or more of the following formulae:

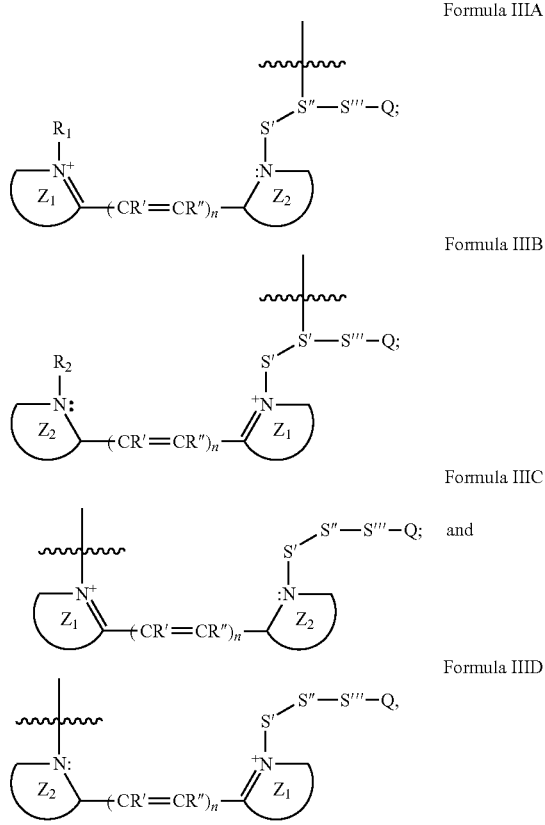

Formula IIIA

Formula IIIB

Formula IIIC

Formula IIID wherein:

$Z_1$, $Z_2$, R', R" and n are as described herein for Formula II, and can form any of the cyanine structures depicted and described herein in Formulae IIA and IIB; and $R_1$ and $R_2$, if present, are each independently hydrogen, a substituted or unsubstituted alkyl or a substituted or unsubstituted cycloalkyl;

In some embodiments, $Z_1$ and $Z_2$ are each independently a substituted or unsubstituted heterocylic moiety, as described herein.

Exemplary such system is presented in FIG. 39.

Herein throughout, the curled line indicates an attachment point to the first cleavable linking moiety, either directly, or via spacer (e.g., degradable spacer, as described herein).

In some of any of the embodiments described herein, an ICT modular system is used as a fluorogenic moiety. In these embodiments, the fluorogenic moiety is a modified fluorescent moiety which exhibits reduced fluorescence, as described herein, due to an alteration in its chemical structure. Upon cleavage of the linking moiety, the fluorogenic undergoes rearrangement and a fluorescent moiety is generated. Thus, a fluorescent signal is generated.

In some of these embodiments, s is 0.

In some of these embodiments, a cyanine-like fluorogenic moiety as described herein has a chemical arrangement which is different from cyanine dyes (e.g., a delocalized π-electrons system), and hence the fluorogenic moiety is spectroscopically silenced in the NIR range before activation by said cleavage.

In some embodiments, such a fluorogenic moiety is represented by Formula IV:

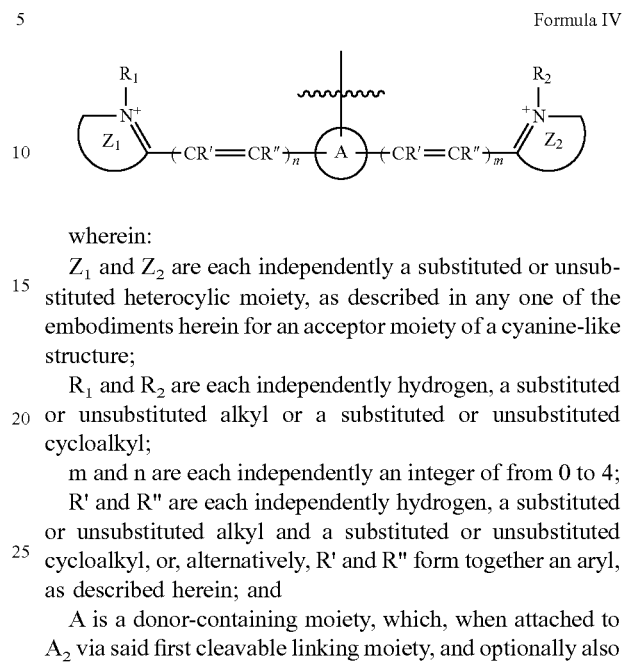

Formula IV wherein:

$Z_1$ and $Z_2$ are each independently a substituted or unsubstituted heterocylic moiety, as described in any one of the embodiments herein for an acceptor moiety of a cyanine-like structure;

$R_1$ and $R_2$ are each independently hydrogen, a substituted or unsubstituted alkyl or a substituted or unsubstituted cycloalkyl;

m and n are each independently an integer of from 0 to 4;

R' and R" are each independently hydrogen, a substituted or unsubstituted alkyl and a substituted or unsubstituted cycloalkyl, or, alternatively, R' and R" form together an aryl, as described herein; and A is a donor-containing moiety, which, when attached to $A_2$ via said first cleavable linking moiety, and optionally also via a spacer (e.g., a degradable spacer) interferes with a conjugation of π electrons between $Z_1$ and $Z_2$, and upon cleavage, participates in said conjugation of π electrons.

The curled line denotes an attachment point.

As shown in Formula IV, both $Z_1$ and $Z_2$ moieties are acceptor moieties, and the donor moiety A is inactivated by its linkage to the linking moiety. Thus, the conjugation of π electrons in the moiety is disrupted. Once the linking moiety is cleaved, the donor-containing moiety functions as a donor, and a conjugated π electron system is generated, resulting in a fluorescent moiety and generation of a fluorescent signal.

Unlike cyanine dyes, in the modified cyanine structures disclosed herein, the presence of a donor moiety interferes with the resonance (the delocalization of π electrons) between the two nitrogen atoms, and both nitrogen atoms are positively charged (e.g., in a form of an ammonium ion). As such, there is no delocalization of π-electrons (no resonating electrons) between the nitrogen-containing moieties.

Thus, in some embodiments, the fluorogenic moiety disclosed herein has a cyanine-like structure, modified so as to include two positively charged nitrogen (e.g., ammonium)-containing moieties (instead of two nitrogen-containing moieties with one positive charge resonating therebetween) and a donor moiety that forms a conjugated π-electron system with the two ammonium-containing moieties, whereby the donor-moiety interferes with the delocalization of the π-electrons system of a non-modified cyanine-like molecule, by restricting delocalization of π-electrons to portions of the molecule that do not involve the nitrogen-containing moieties, and thus reduces or abolishes the delocalization of the positive charge that is present in non-modified cyanine-like molecules.

Such a fluorogenic moiety is designed such that upon the cleavage of the first linking moiety, delocalization of the positive charge is restored.

Thus, the fluorogenic moieties described in these embodiments follow a design in which the inclusion of the donor moiety results in delocalization of π electrons through a smaller portion of the molecule (smaller number of overlapping p-orbitals), as compared to non-modified cyanine structures, and hence the moiety is incapable of interacting with light so as to emit NIR light.

The fluorogenic moiety disclosed herein, however, further follows a design in which upon the cleavage of the linking moiety, rearrangement of the donor moiety occurs and results in a structure in which π electrons are relocalized such that one of the ammonium-containing moieties becomes an amine-containing moiety, and thus a resonating positive charge between two nitrogen-containing moieties, as in cyanine dyes, is restored. The π electrons relocalization thus results in a moiety that has spectroscopic behavior similar to cyanine dyes, and is thus capable of emitting NIR light.

Accordingly, the cyanine-based fluorogenic moieties described in these embodiments are designed after known cyanine dyes, by having two nitrogen-containing moieties and a carbomethine-containing chain linking therebetween, yet differ from cyanine dyes by the presence of two positively charged (e.g., ammonium) nitrogen-containing moieties (instead of one positively charged nitrogen-containing moiety), and further by the presence of a donor moiety as described herein.

Fluorogenic moieties which are equivalent to such fluorogenic moieties, but in which the donor-containing moiety is attached to cleavable moiety Y are disclosed in WO 2012/123916. Each of these moieties can be used in these embodiments, upon the modification explained herein.

An exemplary such a system is presented in FIG. 41.

Any of the fluorogenic moieties described herein can be attached to a terminal or non-terminal backbone unit of the first polymeric backbone.

In some of any of the embodiments described herein, the backbone units form a polymeric backbone of a HPMA copolymer, as described herein.

In some of these embodiments, the polymeric moiety can be represented by Formula IA:

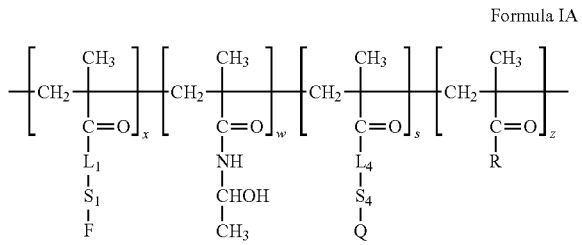

Formula IA wherein the variables are as defined herein, and R represents a reactive group, as described herein.

In some of these embodiments, x and s are other than 0.

In some of these embodiments, the backbone units containing the quenching agent is a terminal backbone unit, and the quenching agent Q is attached to the backbone unit via a spacer ($S_4$).

In some of any of the embodiments described herein, the backbone units form a polymeric backbone of a PGA polymer, as described herein.

In some of these embodiments, the polymeric moiety can be represented by Formula IB:

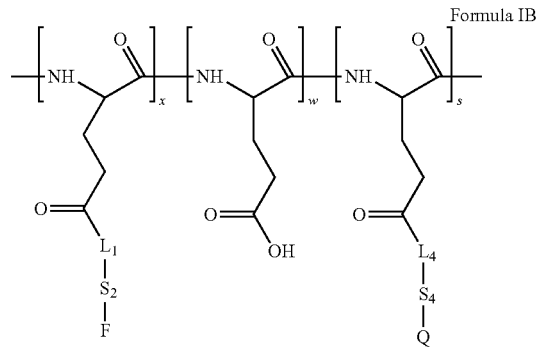

Formula IB wherein the variables are as defined herein.

In some of these embodiments, x and s are other than 0.

In some of any of the embodiments described herein, the backbone units form a polymeric backbone of a PEG polymer, as described herein. In some of these embodiments, the quenching agent forms a part of the fluorogenic moiety, and the fluorogenic moiety is attached to a terminal backbone unit of the polymer.

A Second Polymeric Moiety:

According to some of any of the embodiments described herein, the fluorogenic moiety is attached to one portion of the backbone units and the therapeutically active agent is attached to another portion of the backbone units.

According to some of any of the embodiments described herein, the system further comprises a second polymeric moiety comprising a second polymeric backbone composed of a plurality of backbone units and having attached to at least a portion of the backbone units a therapeutically active agent.

According to some of any of the embodiments described herein, the therapeutically active agent is attached to the backbone units via a second cleavable linking moiety.

According to some of any of the embodiments described herein, the second linking moiety is a biocleavable linking moiety.

According to some of any of the embodiments described herein, the second linking moiety is an enzymatically-cleavable linking moiety.

According to some of any of the embodiments described herein, the first and second cleavable linking moieties are the same or are cleavable by the same mechanism (e.g., the same enzyme).

In some embodiments, the therapeutically active is attached to the backbone units or to the linking moiety, if present, via a spacer, as described in any one of the respective embodiments.

In some embodiments, the backbone units in the second polymeric backbone form a HPMA copolymer backbone.

In some embodiments, the backbone units in the second polymeric backbone form a PGA polymer backbone.

The backbone units if the second polymeric backbone can be the same or different from the backbone units of first polymeric backbone, and are preferably the same.

A System with a Single Polymeric Backbone:

According to some of any of the embodiments described herein, the therapeutically active agent forms a part of the fluorogenic moiety, or is attached to the first cleavable linking moiety, such that upon the cleavage of the first linking moiety, as described herein, the therapeutically active agent is released. According to some embodiments, upon the cleavage, a fluorescent moiety is generated, as described herein.

According to some of any of the embodiments described herein, the fluorescent moiety is or comprises a cyanine dye, as described herein.

According to some of any of the embodiments described herein, the therapeutically active agent is attached to the first linking moiety, preferably via a degradable spacer, as described herein.

According to some of any of the embodiments described herein, the therapeutically active agent forms a part of the fluorogenic moiety, and the fluorogenic moiety is represented by Formula VIA, VIB, VIC, or VID, as depicted herein.

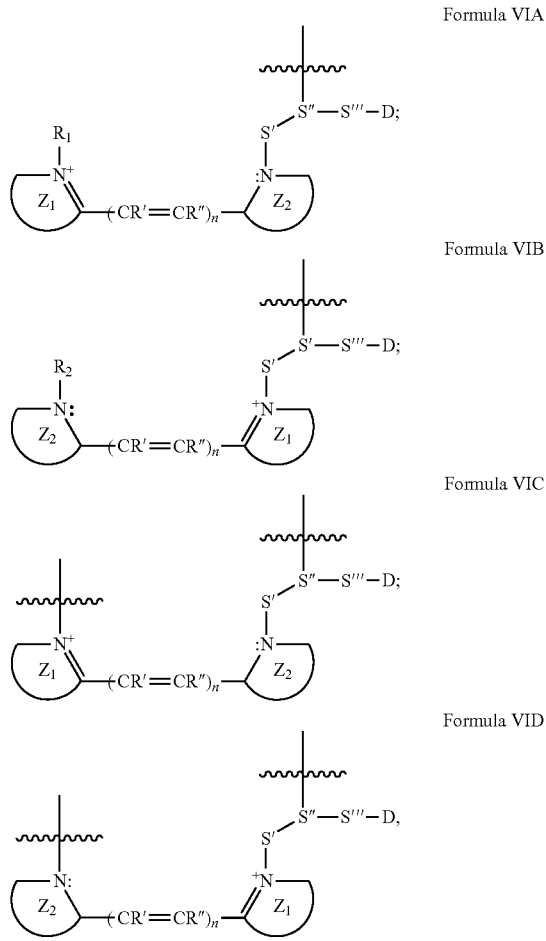

wherein:

$Z_1$ and $Z_2$ are each independently a substituted or unsubstituted heterocylic moiety, as described herein;

$R_1$ and $R_2$ are each independently hydrogen, a substituted or unsubstituted alkyl or a substituted or unsubstituted cycloalkyl;

n is an integer of from 1 to 10;

R' and R" are each independently hydrogen, a substituted or unsubstituted alkyl and a substituted or unsubstituted cycloalkyl, or, alternatively, R' and R" form together an aryl;

S', S" and S' are each independently a degradable spacer, or absent, as described herein for Formulae IIIA, IIIB, IIIC and IIID; and D is the therapeutically active agent, wherein the curled line indicates an attachment point.

According to some of any of the embodiments described herein, both the therapeutically active agent and the quenching agent form a part of the fluorogenic moiety, and the fluorogenic moiety is represented by Formula IIIA, IIIB, IIIC or IIID, and wherein the therapeutically active agent is attached to one of the spacers shown therein or to the cleavable linking moiety.

According to some of any of the embodiments described herein, the therapeutically active agent forms a part of the fluorogenic moiety, and the fluorogenic moiety is represented by Formula IV, wherein the therapeutically active is attached to the donor moiety or to the cleavable linking moiety.

A polymeric system according to some of these embodiments can be represented by Formula I:

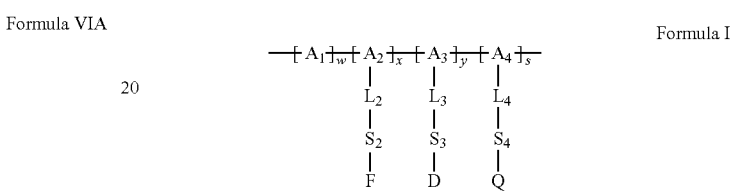

wherein:

D is a therapeutically active agent, as described herein;

F is a fluorogenic moiety as described in any one of its respective embodiments;

Q is a quenching agent, as described in any one of its respective embodiments;

$L_2$ is said first linking moiety;

$L_3$ is said second linking moiety or absent;

$L_4$ is a linking moiety linking the quenching agent, as described herein, or absent;

each of $S_2$, $S_3$ and $S_4$ is independently a spacer, as described in any one of its respective embodiments, or absent;

w is an integer having a value such that w/(x+y+w+s) multiplied by 100 is in the range of from 0 to 99.9;

x is an integer having a value such that x/(x+y+w+s) multiplied by 100 is in the range of from 0.1 to 100;

y is an integer having a value such that y/(x+y+w+s) multiplied by 100 is in the range of from 0 to 100; and s is an integer having a value such that s/(x+y+w+s) multiplied by 100 is in the range of from 0 to 99.9.

$A_1$, $A_2$, $A_3$ and $A_4$ are each backbone units covalently linked to one another and forming a polymeric backbone, such that each [$A_3$-$L_3$-$S_3$-D] independently represents a backbone unit having attached thereto said therapeutically active agent;

each [$A_2$-$L_2$-$S_2$-F] independently represents a backbone unit having attached thereto said fluorogenic moiety; and each [$A_4$-$L_4$-$S_4$-Q] independently represents a backbone unit having attached thereto said quenching agent.

According to some embodiments, $A_4$ is a terminal backbone unit, as described herein.

According to some embodiments, the quenching agent forms a part of the fluorogenic moiety, as described herein, in which case, "s" is 0.

According to some embodiments, the therapeutically active agent forms a part of the fluorogenic moiety, as described herein, in which case, "y" is 0.

According to some embodiments, the polymeric system further comprises backbone units $A_5$ as described herein, and the mol percent is defined accordingly, as shown herein for Formula IA.

According to some of any of the embodiments described herein, the backbone units form a polymeric backbone of HPMA co-polymer.

In some of these embodiments, the polymeric system is represented by the Formula 1A as described herein, and further comprises suitable backbone units comprising the therapeutically active agent, as described herein.

According to some of any of the embodiments described herein, the backbone units form a polymeric backbone of a PGA polymer.

In some of these embodiments, the polymeric system is represented by the Formula 1B as described herein, and further comprises suitable backbone units comprising the therapeutically active agent, as described herein.

Processes of Preparing a Polymeric System:

According to an aspect of some embodiments of the present invention there is provided a process of preparing a polymeric system which comprises a first and a second polymeric moieties, as described herein, the process comprising:

conjugating the fluorogenic compound to a first polymeric backbone in which at least a portion of the backbone units have the first cleavable linking moiety attached thereto and terminate with a first reactive group, thereby preparing the first polymeric backbone; and conjugating the therapeutically active agent to a second polymeric backbone in which at least a portion of the backbone units terminate with a second reactive group, thereby preparing the second polymeric backbone.

According to some embodiments, the therapeutically active agent is attached to the second polymeric backbone via a cleavable linking moiety, the process comprising conjugating the therapeutically active agent to a second polymeric backbone in which the portion of the backbone units have the second cleavable linking attached thereto, thereby preparing the second polymeric backbone.

According to some embodiments, conjugating the therapeutically active agent and/or to the fluorogenic moiety to the backbone units comprises attaching a spacer to the therapeutically active agent and/or to the fluorogenic moiety, and conjugating the spacer to the backbone units.

According to an aspect of some embodiments of the present invention there is provided a process of preparing a polymeric system which comprises a single polymeric moiety, the process comprising:

polymerizing a first plurality of monomers, at least one portion of the monomers have the first linking moiety attached to and terminate with a first reactive group for reacting with the fluorogenic moiety or with a fluorogenic moiety conjugated to a spacer, to thereby form the first polymeric backbone in which a portion of the backbone units terminate with the first reactive group;

polymerizing a second plurality of monomers, at least a portion of the monomers terminate with a second reactive group for reacting with the therapeutically active agent or with the therapeutically active agent conjugated to a spacer, to thereby form the second polymeric backbone in which a portion of the backbone units terminate with the second reactive group; and attaching the fluorogenic moiety to the first reactive group and the therapeutically active agent to the second reactive group, thereby providing the polymeric system.

The copolymerization of the various monomers can be effected by any polymerization method known in the art, using suitable polymerization initiators and optionally chain transfer agents. Such suitable polymerization initiators and chain transfer agents can be readily identified by a person skilled in the art.

Using the RAFT approach enables to perform the copolymerization at room temperature.

The "reversible addition-fragmentation chain transfer" (RAFT) polymerization technique typically involves the use of thiocarbonylthio compounds, such as dithioesters, dithiocarbamates, trithiocarbonates, and xanthates in order to mediate the polymerization via a reversible chain-transfer process. This allows access to polymers with low polydispersity and high functionality.

In some embodiments, the reactive groups can be protected prior to the respective conjugation thereto. In such cases, the process further comprises deprotecting the reactive group prior to the respective conjugation.

This allows a regio-controlled conjugation of, for example, the anti-angiogenesis agent to those backbone units that comprises a biodegradable linker.

According to some embodiments, the polymerizing or co-polymerizing is performed via RAFT polymerization.

Exemplary processes are described in detail in the Examples section that follows. These processes can be utilized with any of the fluorogenic moieties, therapeutically active agents and quenching agents as described herein.

The exemplary processes described in the Examples section that follows and accompanying figures, can be manipulated as desired to suit the selected cleavable linking moiety or moieties, therapeutically active agent and fluorogenic/fluorescent moiety (and the selected Turn-ON mechanism).

Additional Polymeric Systems:

According to an aspect of some embodiments of the present invention there is provided a polymeric system which comprises a fluorogenic cyanine moiety covalently attached via a cleavable linking moiety to a quenching agent, such that upon cleavage of the linking moiety, a fluorescent cyanine moiety is generated. In some embodiments, the system further comprising a polymeric moiety attached to the fluorogenic cyanine moiety.

According to some of any of the embodiments described herein, the polymeric system is represented by a formula selected from Formula VA or VB:

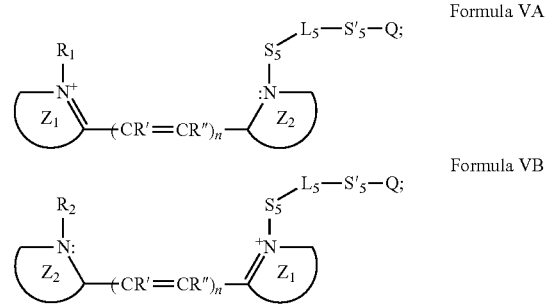

wherein:

$Z_1$ and $Z_2$ are each independently a substituted or unsubstituted heterocylic moiety, as described herein;

$R_1$ and $R_2$ are each independently a polymeric moiety;

n is an integer of from 1 to 10;

R' and R'' are each independently hydrogen, a substituted or unsubstituted alkyl and a substituted or unsubstituted cycloalkyl, or, alternatively, R' and R'' form together an aryl;

$S_5$ and $S'_5$ are each independently a degradable spacer, as described herein, or absent;

$L_5$ is the cleavable linking moiety; and

Q is the quenching agent.

The cleavable moiety can be any of the cleavable moieties described herein.

According to some of any of the embodiments described herein, the cyanine moiety is attached to the polymeric moiety via a spacer, preferably a degradable spacer as described herein.

In some embodiments, the fluorogenic moiety described herein is a FRET-based system, as described herein, preferably a pair-FRET system.

Modular FRET systems previously described in the art (e.g., Redy et al. supra), can be conjugated according to these embodiments, via a degradable spacer, to a polymeric moiety.

In some of these embodiments, the polymeric moiety is PEG. Other polymeric moieties, for example, as described herein, are contemplated.

According to some of any of the embodiments described herein, the polymeric system further comprises a therapeutically active agent, wherein:

(i) the therapeutically active agent is attached to the cleavable linking moiety, such that upon its cleavage, the therapeutically active agent is released;

(ii) the therapeutically active agent is attached to the degradable spacer, such that upon its cleavage, the therapeutically active agent is released; or (iii) the therapeutically active agent is attached to a second polymeric moiety, for forming a combined polymeric system, similarly to any of the other embodiments described herein.

Applications:

According to an aspect of some embodiments of the present invention there is provided a polymeric system as described in any one of the embodiments described herein, where the system comprises a therapeutically active agent, for use in the treatment and diagnosis of a medical condition treatable by the therapeutically active agent, or for use in the preparation of a medicament for treating the medical condition.

According to an aspect of some embodiments of the present invention there is provided a method of treating a medical condition, the method comprising administering to a subject in need thereof a polymeric system as described herein, which comprises a therapeutically active agent that is usable in treating the medical condition.

According to some of any of the embodiments described herein, the medical condition is cancer.

According to some embodiments of the invention, the therapeutically active agent is an anti-cancer agent.

In some of these embodiments, the therapeutically active agent is an anti-tumor agent (an anti-cancer agent, an anti-proliferative agent, an anti-angiogenesis agent, a chemotherapeutic agent), such as paclitaxel (PTX), as exemplified herein.

According to an aspect of some embodiments of the present invention there is provided a polymeric system according to any one of the embodiments described herein, for use in the treatment and diagnosis of a medical condition treatable by the therapeutically active agent.

According to an aspect of some embodiments of the present invention there is provided a method of treating and monitoring a medical condition treatable by the therapeutically active agent.

According to an aspect of some embodiments of the present invention there is provided a method of treating and monitoring a medical condition treatable by the therapeutically active agent, by administering the polymeric system as described herein to a subject in need of such treatment.

According to an aspect of some embodiments of the present invention there is provided a use of a polymeric system as described herein for preparing a medicament for treating and monitoring a medical condition treatable by the therapeutically active agent.

According to some embodiments of the invention, the medical condition is cancer, the therapeutically active agent is an anti-tumor agent and the cleavable linking moiety/moieties are cleavable by an enzyme expressed or overexpressed in tumor tissues.

According to some embodiments of the present invention, treatment and monitoring or diagnosis are performed simultaneously, and thus may allow real-time monitoring and evaluation of the treatment.

The terms "cancer" and "tumor" are used interchangeably herein to describe a class of diseases in which a group of cells display uncontrolled growth (division beyond the normal limits). The term "cancer" encompasses malignant and benign tumors as well as disease conditions evolving from primary or secondary tumors. The term "malignant tumor" describes a tumor which is not self-limited in its growth, is capable of invading into adjacent tissues, and may be capable of spreading to distant tissues (metastasizing). The term "benign tumor" describes a tumor which is not malignant (i.e. does not grow in an unlimited, aggressive manner, does not invade surrounding tissues, and does not metastasize). The term "primary tumor" describes a tumor that is at the original site where it first arose. The term "secondary tumor" describes a tumor that has spread from its original (primary) site of growth to another site, close to or distant from the primary site.

Non-limiting examples of therapeutically active agents that can be efficiently incorporated in the herein described polymeric systems include amino containing chemotherapeutic agents such as daunorubicin, doxorubicin, N-(5,5-diacetoxypentyl)doxorubicin, anthracycline, mitomycin C, mitomycin A, 9-amino camptothecin, aminopertin, aminomycin, $N^8$-acetyl spermidine, 1-(2-chloroethyl)-1,2-dimethanesulfonyl hydrazine, bleomycin, tallysomucin, and derivatives thereof; hydroxy containing chemotherapeutic agents such as etoposide, camptothecin, irinotecaan, topotecan, 9-amino camptothecin, paclitaxel, docetaxel, esperamycin, 1,8-dihydroxy-bicyclo[7.3.1] trideca-4-ene-2,6-diyne-13-one, anguidine, morpholino-doxorubicin, vincristine and vinblastine, and derivatives thereof, sulfhydryl containing chemotherapeutic agents and carboxyl containing chemotherapeutic agents. Any other anti-cancer agents are also contemplated.

Other therapeutically active agents that can be beneficially incorporated in the herein described polymeric systems include, for example, antihistamines, anesthetics, analgesics, anti-fungal agents, antibiotics, anti-inflammatory agents, vitamins and anti-infectious agents.

It is expected that during the life of a patent maturing from this application many relevant cyanine dyes, fluorogenic moieties, therapeutically active agent and/or polymers will be developed and the scope of the terms cyanine dye, cyanine-like structure, polymeric backbone and therapeutically active agent, is intended to include all such new technologies a priori.

General:

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it means that the group, in this case the alkyl group, may contain 1 carbon atom, 2 carbon atoms, 3 carbon atoms, etc., up to and including 20 carbon atoms. In some embodiments, the alkyl group has 1-10 carbon atoms. In some embodiments, the alkyl group has 1-4 carbon atoms. Exemplary alkyl groups include, but are not limited to methyl, ethyl, propyl, butyl, pentyl, hexyl, heptyl, octyl, nonyl, decyl, undecyl, dodecyl, tridecyl, tetradecyl, pentadecyl, heptadecyl, octadecyl and nonadecyl.

The term "cycloalkyl" describes an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane.

The term "aryl" describes an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system.

The term "hydroxy" describes an —OH group.

The term "alkoxy" describes both an —O-alkyl and an —O-cycloalkyl group, as defined herein.

The term "thiol" describes a —SH group.

The term "thioalkoxy" describes both an —S-alkyl group, and an —S-cycloalkyl group, as defined herein.

The term "cyano" describes a —C≡N group.

The term "carbonyl" describes a —C(=O)—R' group, where R' is hydrogen, alkyl, cycloalkyl, aryl, heteroaryl (bonded through a ring carbon) or heteroalicyclic (bonded through a ring carbon) as defined herein.

The term "thiocarbonyl" describes a —C(=S)—R' group, where R' is as defined herein.

The term "O-carbamyl" describes an —OC(=O)—NR'R" group, where R' is as defined herein and R" is hydrogen, alkyl, cycloalkyl, aryl, heteroaryl (bonded through a ring carbon) or heteroalicyclic (bonded through a ring carbon) as defined herein.

The term "N-carbamyl" describes an R'OC(=O)—NR"— group, where R' and R" are as defined herein.

The term "O-thiocarbamyl" describes an —OC(=S)—NR'R" group, where R' and R" are as defined herein.

The term "N-thiocarbamyl" describes an R"OC(=S)NR'— group, where R' and R" are as defined herein.

The term "C-amido" describes a —C(=O)—NR'R" group, where R' and R" are as defined herein.

The term "N-amido" describes an R'C(=O)—NR" group, where R' and R" are as defined herein.

The term "C-carboxy" describes a —C(=O)—O—R' groups, where R' is as defined herein.

The term "O-carboxy" describes an R'C(=O)—O— group, where R' is as defined herein.

The term "nitro" group describes an —NO$_2$ group.

The term "amino" group describes an —NH$_2$ group.

The term "sulfonyl" group describes an —S(=O)$_2$—R' group, where R' is as defined herein.

The term "halogen" or "halo" describes fluoro, chloro, bromo or iodo atom.

Herein, the phrase "therapeutically active agent" is also referred to herein as "drug".

The polymeric moieties described herein may possess asymmetric carbon atoms (optical centers) or double bonds; the racemates, diastereomers, geometric isomers and individual isomers are encompassed within the scope of the present invention.

As used herein, the term "enantiomer" describes a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems.

The polymeric moieties described herein can exist in unsolvated forms as well as solvated forms, including hydrated forms. In general, the solvated forms are equivalent to unsolvated forms and are encompassed within the scope of the present invention.

The term "solvate" refers to a complex of variable stoichiometry (e.g., di-, tri-, tetra-, penta-, hexa-, and so on), which is formed by a solute (the conjugate described herein) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

As used herein, a "reactive group" describes a chemical group that is capable of reacting with another group so as to form a chemical bond, typically a covalent bond. Optionally, an ionic or coordinative bond is formed.

A reactive group is termed as such if being chemically compatible with a reactive group of an agent or moiety that should be desirably attached thereto. For example, a carboxylic group is a reactive group suitable for conjugating an agent or a moiety that terminates with an amine group, and vice versa.

A reactive group can be inherently present in the monomeric units forming the backbone units, or be generated therewithin by terms of chemical modifications of the chemical groups thereon or by means of attaching to these chemical groups a spacer or a linker that terminates with the desired reactive group.

The term "subject" (alternatively referred to herein as "patient") as used herein refers to an animal, preferably a mammal, most preferably a human, who has been the object of treatment, observation or experiment.

In any of the methods and uses described herein, any of the polymeric moieties described herein can be provided to an individual either per se, or as part of a pharmaceutical composition where it is mixed with a pharmaceutically acceptable carrier.

As used herein a "pharmaceutical composition" refers to a preparation of one or more of the polymeric moieties described herein (as active ingredient), or physiologically acceptable salts or prodrugs thereof, with other chemical components including but not limited to physiologically suitable carriers, excipients, lubricants, buffering agents, antibacterial agents, bulking agents (e.g. mannitol), antioxidants (e.g., ascorbic acid or sodium bisulfite), anti-inflammatory agents, anti-viral agents, chemotherapeutic agents, anti-histamines and the like. The purpose of a pharmaceutical composition is to facilitate administration of a compound to a subject. The term "active ingredient" refers to a compound, which is accountable for a biological effect.

The terms "physiologically acceptable carrier" and "pharmaceutically acceptable carrier" which may be interchangeably used refer to a carrier or a diluent that does not cause significant irritation to an organism and does not abrogate the biological activity and properties of the administered compound.

Herein the term "excipient" refers to an inert substance added to a pharmaceutical composition to further facilitate administration of a drug. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the compounds into preparations which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p.1).

The pharmaceutical composition may be formulated for administration in either one or more of routes depending on whether local or systemic treatment or administration is of choice, and on the area to be treated. Administration may be done orally, by inhalation, or parenterally, for example by intravenous drip or intraperitoneal, subcutaneous, intramuscular or intravenous injection, or topically (including ophthalmically, vaginally, rectally, intranasally).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

The pharmaceutical composition may further comprise additional pharmaceutically active or inactive agents such as, but not limited to, an anti-bacterial agent, an antioxidant, a buffering agent, a bulking agent, a surfactant, an anti-inflammatory agent, an anti-viral agent, a chemotherapeutic agent and an anti-histamine.

According to an embodiment of the present invention, the pharmaceutical composition described hereinabove is packaged in a packaging material and identified in print, in or on the packaging material, for use in the treatment and/or monitoring of a disease or disorder or medical condition as described herein.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

In any of the methods, uses and compositions described herein, the polymeric systems described herein can be utilized in combination with additional therapeutically active agents. Such additional agents include, as non-limiting examples, chemotherapeutic agents, anti-angiogensis agents, hormones, growth factors, antibiotics, anti-microbial agents, anti-depressants, immunostimulants.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Methods

Materials:

HPMA copolymer-Gly-Phe-Leu-Gly-ONp incorporating 10 mol % of the methacryloyl-Gly-Phe-Leu-Gly-p-nitrophenol ester monomer units and HPMA copolymer-Gly-Phe-Leu-Gly-ethylenediamine (HPMA-GFLG-en) incorporating 10 mol % of the methacryloyl-Gly-Phe-Leu-Gly-ethylenediamine were obtained from Polymer Laboratories (Church Stretton, U.K.). The HPMA copolymers have a molecular weight of 31,600 Da and a polydispersity of 1.66.

PTX was purchased from Petrus Chemicals and Materials 1986 (LTD) (China).

Dulbecco's modified Eagle's medium (DMEM) and PBS, RPMI 1640, fetal bovine serum (FBS), penicillin, streptomycin, nystatin, 1-glutamine, Hepes buffer, sodium pyruvate, and fibronectin were purchased from Biological Industries Ltd. (Kibbutz Beit Haemek, Israel).

EGM-2 medium was purchased from Cambrex, USA and endothelial cells growth supplement (ECGS) from Zotal (Israel).

All other chemical reagents, including salts and solvents, were purchased from Sigma-Aldrich (Rehovot, Israel).

All reactions requiring anhydrous conditions were performed under Argon or $N_2$ atmosphere. Chemicals and solvents were either AR grade or purified by standard techniques.

Thin layer chromatography (TLC): silica gel plates Merck 60 $F_{254}$: compounds were visualized by irradiation with UV light.

Flash chromatography (FC): silica gel Merck 60 (particle size 0.040-0.063 mm), eluent given in parentheses.

High pressure liquid chromatography (HPLC): C18 5u, 250×4.6 mm, eluent given in parentheses.

Preparative HPLC: C18 5u, 250×21 mm, eluent given in parentheses.

$^1$H-NMR spectra were measured using Bruker Avance operated at 400 MHz as mentioned. $^{13}$C-NMR spectra were measured using Bruker Avance operated at 400 MHz as mentioned.

Absorption and fluorescence spectra were recorded on Spectramax-M2 fluorescent spectrometer using quartz cuvettes or quartz 96-wells plate reader.

Some Abbreviations:

ACN—Acetonitrile, DCM—Dichloromethane, DMAP—4-Dimethylaminopyridine, DMF—N,N-Dimethylformamide, EtOAc—Ethylacetate, Hex—n-Hexanes, MeOH—Methanol, THF—Tetrahydrofurane, TFA—Trifluoroacetic acid, $Et_3N$—Triethylamine, EtOH—Ethyl alcohol, NaOAc—Sodium acetate, $Ac_2O$—Acetic anhydride, DCC—N,N'-Dicyclohexylcarbodiimide, AcOH—Acetic acid.

Dynamic Light Scattering (DLS) Analysis and Surface Charge Measurements:

The mean hydrodynamic diameter of the HPMA copolymer-PTX conjugate and the zeta-potential measurements were performed using a ZetaSizer Nano ZS instrument with an integrated 4Mw He—Ne laser ($\lambda$=532 nm; Malvern Instruments Ltd., Malvern, Worcestershire, UK). HPMA copolymer-PTX sample were prepared by dissolving 1 mg of polymer conjugate in 1 ml of 15.5 mM phosphate buffer, pH=7.4. The polymer solution was vortexed and then filtered through 0.2 μM filter. All measurements were performed at 25° C. using polystyrol/polystyrene (10×4×45) mm cell for DLS analysis and folded capillary cell (DTS 1070) for zeta-potential measurements.

Cathepsin B Activity Assays:

PTX and Cy5 enzymatically-directed release from the conjugates was studied in vitro, upon incubation at 37° C. with Cathepsin B (1 unit/ml) in freshly prepared activity phosphate buffer (0.1 M, pH=6.0), containing 0.05 M NaCl, 1 mM Ethylenediaminetetraacetic acid (EDTA) and 5 mM reduced glutathione (GSH). As a control, conjugates were incubated in the absence of Cathepsin B in activity phosphate buffer (0.1 M, pH=6.0), containing 0.05 M NaCl, 1 mM Ethylenediaminetetraacetic acid (EDTA) and 5 mM reduced glutathione (GSH), and/or in Dulbecco's PBS (pH 7.4). Release of Cy5 from HPMA copolymer-Cy5 conjugate: Free Cy5 release was monitored by measuring the change in the fluorescence intensity at sequential time points. The fluorescence measurements were carried out at excitation wavelengths of 600 nm using SpectraMax M5$^e$ multi-detection reader. Samples (50 μl) were collected every 24 hours (up to 105 hours) and immediately analyzed.

Release of PTX from HPMA Copolymer-PTX-FK Conjugate:

The free PTX release was monitored by reversed phase (RP) HPLC. UltiMate® 3000 Nano LC systems (Dionex)

was used, equipped with 3000 pump, VWD-3000 UV-Vis detector and Chromeleon® 6.80 software. The column in use was Phenomenex Jupiter 5µ 250×4.60 mm C-18 300A. Chromatographic conditions were: flow: 1.0 ml/min, gradient: 20% to 100% solution B in 20 minutes (sol. A—0.1% TFA in water; sol. B—0.1% TFA in acetonitrile (MeCN)).

Samples (100 µl) were collected every 24 hours, until a plateau was observed (up to 50 hours). For PTX extraction, sodium carbonate buffer solution (0.2 M, pH=9.6) was added to each sample, followed by ethyl acetate. Samples were vigorously vortex and centrifuged. The organic layer was carefully removed and evaporated. The residue was dissolved in MeCN and analyzed.

Release of PTX from HPMA Copolymer-PTX Conjugate:

The free PTX release was monitored by reversed phase (RP) HPLC. UltiMate® 3000 Nano LC systems (Dionex) was used, equipped with 3000 pump, VWD-3000 UV-Vis detector and Chromeleon® 6.80 software. The column in use was Phenomenex Jupiter 5µ 250×4.60 mm C-18 300A. Chromatographic conditions were: flow: 1.0 ml/min, gradient: 20% to 100% solution B in 20 minutes (sol. A—0.1% TFA in water; sol. B—0.1% TFA in acetonitrile (MeCN)).

Samples (100 µl) were collected every 24 hours, until a plateau was observed (up to 50 hours). For PTX extraction, sodium carbonate buffer solution (0.2 M, pH=9.6) was added to each sample, followed by ethyl acetate. Samples were vigorously vortex and centrifuged. The organic layer was carefully removed and evaporated. The residue was dissolved in MeCN and analyzed.

Release of Cy5 from PGA-PTX-Cy5 Conjugate:

Cy5 release was monitored by measuring the change in the fluorescence intensity at sequential time points. The fluorescence measurements were carried out at excitation wavelengths of 650 nm using SpectraMax M5$^e$ multi-detection reader. Samples (50 µl) were collected every 24 hours (up to 160 hours) and immediately analyzed.

Cell Cultures:

MDA-MB-231 human mammary adenocarcinoma cell line, 4T1 murine mammary adenocarcinoma cell line and WA239A human melanoma cell line were purchased from the American Type Culture Collection (ATCC, Manassas, Va., USA).

MDA-MB-231 cells were cultured in DMEM supplemented with 10% FBS, 100 µg/mL penicillin, 100 µl/mL streptomycin, 12.5 µl/mL nystatin and 2 mM L-glutamine.

4T1 cells were cultured in RPMI 1640 supplemented with 10% FBS, 100 mg/mL Penicillin, 100 µl/mL Streptomycin, 12.5 µl/mL Nystatin, and 2 mM L-glutamine, 1 mM Sodium pyruvate, 10 mM HEPES buffer and 2.5 g/L D-glucose.

WM239A cells were cultured in RPMI 1640 supplemented with 10% FBS, 100 mg/ml Penicillin, 100 µl/ml Streptomycin, 12.5 µl/mg Nystatin, and 2 mM L-glutamine.

Cells were grown at 37° C.; 5% $CO_2$.

Human umbilical vein endothelial cells (HUVEC) were purchased from Lonza, Switzerland and were cultured in EGM-2 medium (Lonza, Switzerland). Cells were grown at 37° C.; 5% $CO_2$.

For the study of in vitro degradation of HPMA copolymer-Cy5 conjugate, MDA-MB-231 cells (30,000 cells/ml) were seeded to 24-well culture plates with DMEM supplemented with 10% FBS, 100 µg/mL penicillin, 100 U/mL streptomycin, 12.5 U/mL nystatin and 2 mM L-glutamine. 24 hours later, HPMA-copolymer-Cy5 (3.8%) at a final concentration of 10 µM eq. Cy5 was added. At 0.5, 24 and 48 hours after the addition of the substrate, DMEM was replaced with PBS and the degradation of the conjugate was monitored using SpectraMax M5$^e$ multi-detection reader. Non-treated MDA-MB-231 cells were used as a control.

Cell Viability Assay:

For the study of HPMA copolymer-PTX conjugate antitumor activity:

4T1 cells (3,000 cells/well), HUVEC (10,000 cells/well) and MDA-MB-231 cells (10,000 cells/well) were plated onto 24-well culture plates in RPMI supplemented with 2% FBS, EBM-2 supplemented with 5% FBS or in DMEM supplemented with 10% FBS respectively, and incubated for 24 hours (37° C.; 5% CO2). The medium was then replaced with RPMI 1640 supplemented with 10% FBS, EGM-2 or DMEM supplemented with 10% FBS. Cells were exposed to PTX and PTX bound-conjugates at serial dilutions, at equivalent dose of the free PTX. Number of viable cells was counted by a Z1 Coulter Counter® Cell and Particle Counter (Beckman Coulter®) following 96 hours of incubation.

For the study of PGA-PTX-Cy5 conjugate antitumor activity:

4T1 cells (8,000 cells/wells), WM239A cells (15,000 cells/well) and MDA-MB-231 cells (10,000/well) were plated onto 24-well culture in RPMI supplemented with 10% FBS, or in DMEM supplemented with 10% FBS respectively, and incubated for 24 hours (37° C.; 5% $CO_2$). The medium was then replaced with RPMI 1640 supplemented with 10% FBS or DMEM supplemented with 10% FBS.

Cells were exposed to PTX and PTX-bound conjugates at serial dilutions, at equivalent dose of free PTX. Number of viable cells was counted by a Z1 Coulter Counter® Cell and Particle Counter (Beckman Coulter®) following 72 hours of incubation.

Animals and Tumor Cell Inoculation:

4T1 cells ($3 \times 10^6$) were injected subcutaneously (s.c.) into the flank of female BALB/C mice aged 6-8 weeks). Tumor volume was calculated using the standard formula: length× width×0.52.

Intravital Non-Invasive Imaging of Cy5 Cathepsin B-Dependent Release:

BALB/c mice bearing subcutaneous 4T1 tumors (about 100 $mm^3$) were injected intra-tumorally with HPMA copolymer-Cy5 (0.1 mM; 30 µl) or with equivalent dose of free Cy5. Fluorescent signal within tumor was assessed at different time points 30 hours following injection using non-invasive imaging system CRI Maestro™ Multispectral image-cube were acquired through 650-800 nm spectral range in 10 nm steps using excitation (635 nm longpass) and emission (675 nm longpass) filter set. Mice auto-fluorescence and undesired background signals were eliminated by spectral analysis and linear unmixing algorithm.

Body Distribution of HPMA Copolymer-SQ-Cy5:

BALB/c mice bearing sub-cutaneous 4T1 tumors (about 300 $mm^3$) were injected intravenously (i.v.) with HPMA copolymer-SQ-Cy5 (10 µM; 200 µl). Accumulation of the conjugate in the tumor and organs was assessed at different time points for 12 hours. At termination, tumors and organs were excised and imaged. Organs were imaged using non-invasive imaging system CRI Maestro™ (filter set—Ex/Em 635/675). Mice auto-fluorescence and undesired background signals were eliminated by spectral analysis and linear unmixing algorithm. Time dependent tumor contrast profile was determined by the ratio between fluorescence intensities of tumors and those of normal skin.

Statistical Methods:

Data is expressed as mean±standard deviation (s.d.) for in vitro assays or ±standard error of the mean (s.e.m.) for in vivo. Statistical significance was determined using an unpaired t-test. All statistical tests were two-sided. All experiments were performed in triplicates and repeated at least three times.

Example 1

Chemical Syntheses of HPMA Copolymer Conjugates

Figure 1A:
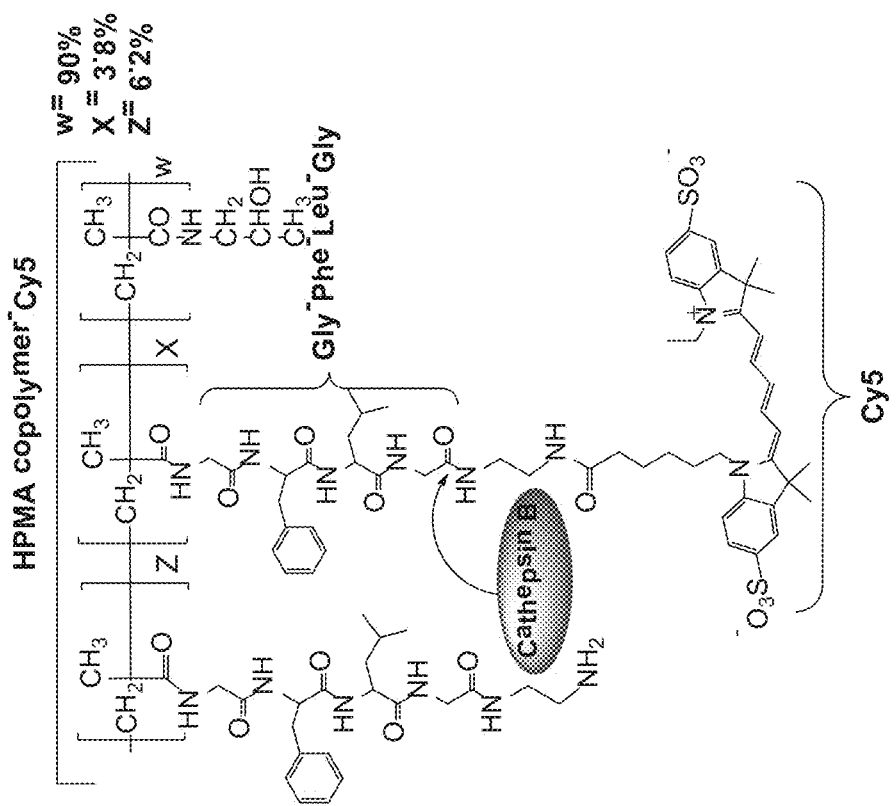

Synthesis of HPMA Copolymer-Cy5 Conjugate:

The structure of an exemplary HPMA copolymer-Cy5 conjugate is depicted in FIG. 1A. An exemplary synthesis of a HPMA Copolymer-Cy5 conjugate is depicted in FIG. 2.

Cy5-COOH was synthesized as previously described [Redy, O., et al., Org. Biomol. Chem., 2012. 10(4): p. 710-5].

Cy5-COOH fluorophore was conjugated with HPMA copolymer-GFLG-en in two-step synthesis, as follows. First, Cy5-COOH (15.1 mg, 0.023 mmol) was dissolved in 0.7 mL anhydrous N,N-Dimethylformamide (DMF). N-Hydroxysuccinimide (NHS) (5.3 mg, 0.046 mmol) and N,N'-dicyclohexylcarbodiimide (DCC) (9.5 mg, 0.046 mmol) were added in order to activate the free carboxylic group of the fluorophore, for further coupling to the HPMA copolymer. The reaction mixture was stirred at room temperature (rT) in dark for 12 hours. Then, HPMA-GFLG-en copolymer (21.1 mg, 0.114 mmol) was dissolved in 0.5 mL anhydrous DMF and added to the reaction mixture. Following the reaction by High Pressure Liquid Chromatography (HPLC) (UltiMate® 3000 Nano LC systems, Dionex), the precipitate was washed with acetone and dried under vacuum.

Purification of the conjugate by size exclusion chromatography (SEC) was performed using AKTA/FPLC system (Pharmacia/GE Healthcare), HiTrap Desalting columns (Sephadex G-25 Superfine) in DDW, flow rate 1.0 ml/min; UV detection.

In order to remove all excess of free fluorophore, the residue was dissolved in water and dialyzed for 1 day at 4° C. (MWCO 6-8 kDa) against DI water. The conjugate was isolated by freeze-drying.

Cy5 loading was determined using SpectraMax M5$^e$ multi-detection reader. The absorbance of conjugated Cy5 was measured and compared to that of free Cy5.

Quenching efficiency was expressed as a percentage of the fluorescence intensity of the HPMA copolymer-Cy5 conjugate ($\lambda_{Em}$=670 nm) compared with the emission of the free Cy5 at the equivalent concentration, as shown in Example 5 below and FIG. 11A.

Figure 1B:
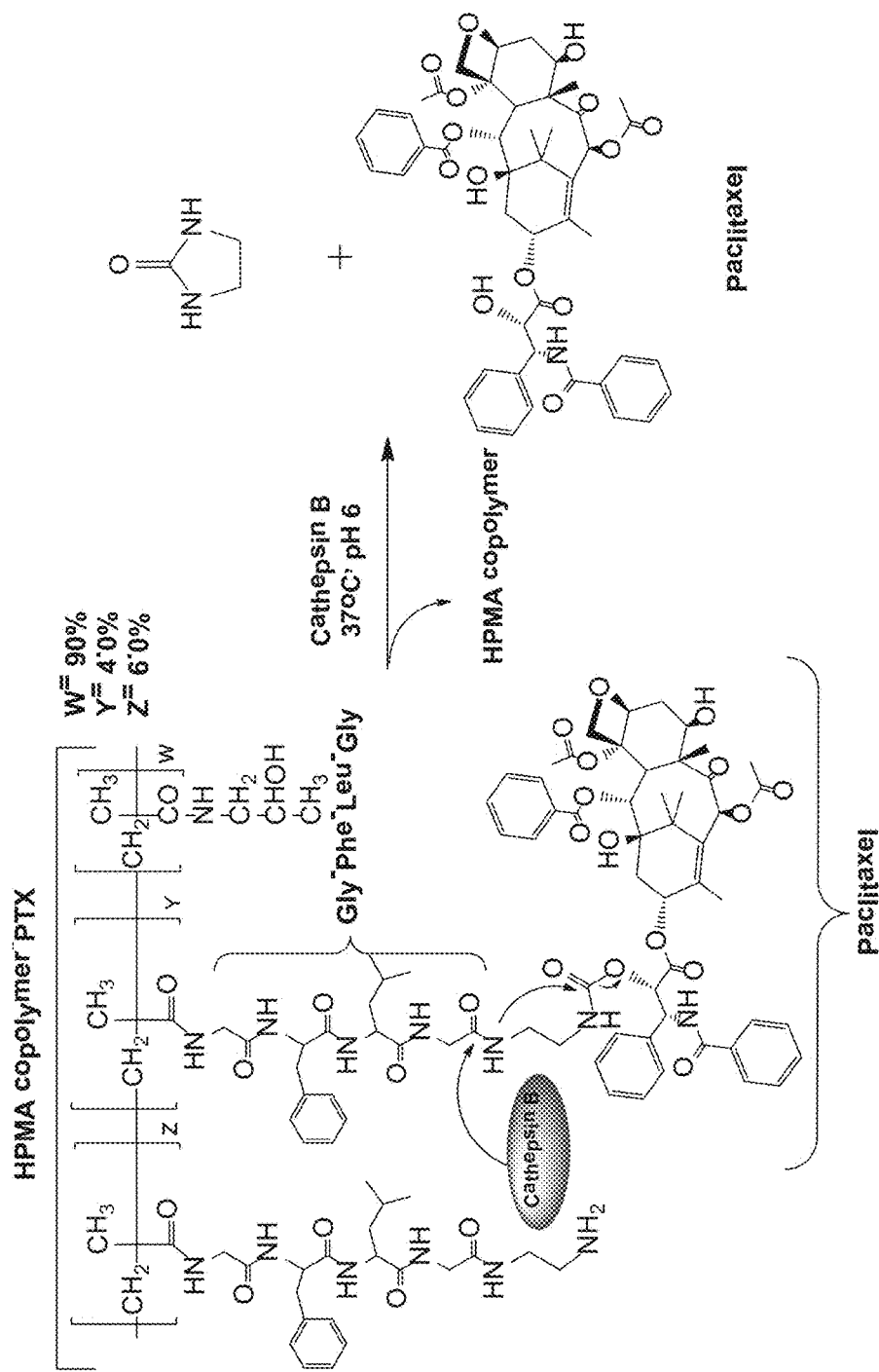

Synthesis of HPMA Copolymer-PTX Conjugate:

The structure of an exemplary HPMA copolymer-PTX conjugate is depicted in FIG. 1B. Paclitaxel (PTX) was conjugated with HPMA copolymer-GFLG-en in two-step synthesis, as depicted in FIG. 3. First, PTX was activated using 4-Nitrophenyl chloroformate (PNP-Cl) in order to form PTX-ONp. PTX (107.2 mg, 0.125 mmol) was dissolved in 1 ml pre-distilled Tetrahydrofuran (THF) and was stirred at −30° C. Triethylamine (Et$_3$N) (140 µl, 1.0 mmol) and a grain of 4-Dimethylaminopyridine (DMAP) were dissolved in the dry solvent and added to the reaction mixture. PNP-Cl (151.2 mg, 0.750 mmol) was dissolved in another 1 ml of THF and added to the reaction. The reaction was followed by Thin Layer Chromatography (TLC) and quenched with 1M HCl at −30° C. The product was extracted from the aqueous media using ethyl acetate and purified by silica gel column.

Then, PTX-ONp was conjugated to the HPMA-GFLG-en copolymer in the presence of Et$_3$N and Nitrogen atmosphere. The PTX content of the HPMA copolymer-PTX conjugate was determined by HPLC analysis, at $\lambda$=270 nm, against a calibration curve for free PTX.

Figure 1C:
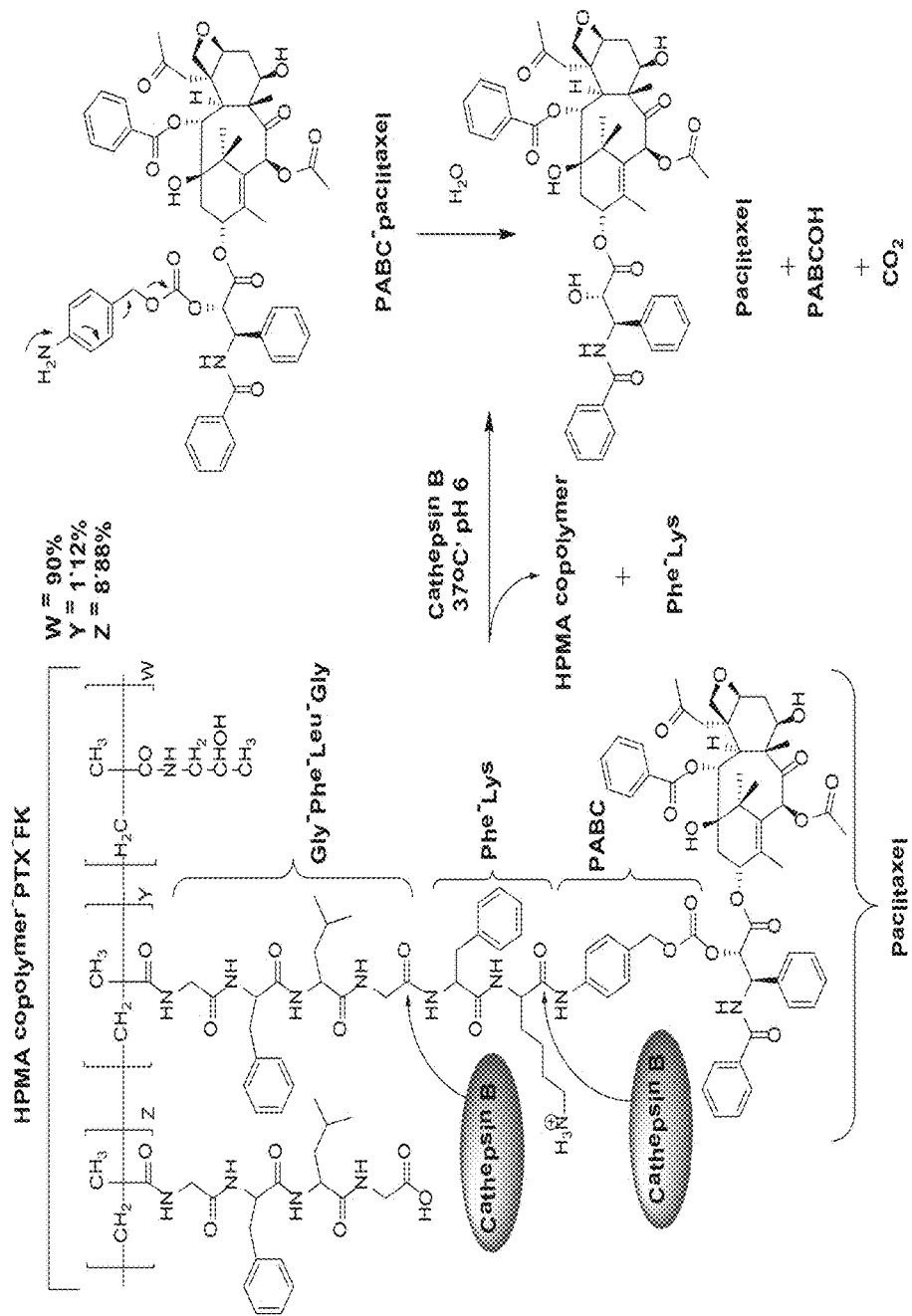

Synthesis of HPMA Copolymer-PTX-FK Conjugate:

The structure of an exemplary HPMA copolymer-PTX-FK conjugate is depicted in FIG. 1C. The synthesis of HPMA copolymer-PTX-FK conjugate is illustrated in FIG. 4.

The conjugation of PTX with HPMA copolymer was performed as previously described [Duncan, R., et al., J Control Release, 2001. 74(1-3): p. 135-46]. Briefly, PTX (168.5 mg, 0.197 mmol) was first attached to an FK-PABC linker (147.5 mg, 0.197 mmol) and the obtained FK-PABC-PTX was conjugated to HPMA copolymer-GFLG-ONp. L-Boc-Phe-ONp was conjugated to L-Lys (alloc)-OH to afford Compound 2. Amidation with 4-aminobenzyl alcohol (PABA) afforded Compound 3, and was followed by activation with p-nitrophenol to afford Compound 4, which was then reacted with PTX to afford Compound 5. Deprotection of the Boc group afforded the free amine, which was then conjugated with HPMA copolymer-GFLG-ONp, as depicted in FIG. 4. Finally, deprotection of the alloc group of the amine residue of Lys afforded the desired HPMA copolymer-PTX-FK, the structure of which is depicted as the final product in FIG. 4 and in FIG. 1C.

The PTX-FK content of the HPMA copolymer-PTX-FK conjugate was determined by HPLC analysis. The PTX-FK content was determined against a calibration curve for free PTX-FK.

Preparation of Compound 2:

L-Boc-Phe-ONp (104.3 mg, 0.27 mmol) was dissolved in 2 mL DMF. Then commercially available L-Lys(alloc)-OH (62 mg, 0.27 mmol) and Et$_3$N (100 µL) were added. The reaction mixture was stirred for 12 hours and was monitored by TLC (AcOH:MeOH:EtOAc 0.5:10:89.5). Upon completion of the reaction the solvent was removed under reduced pressure and the crude product was purified using column chromatography on silica gel (AcOH:MeOH:EtOAc 0.5:10:89.5) to give compound 2 (107 mg, 83%) as a white solid (FIG. 4).

Preparation of Compound 3:

Compound 2 (832.1 mg, 1.74 mmol) was dissolved in dry THF and the solution was cooled to −15° C. Then NMM (0.19 mL, 1.74 mmol) and isobutyl chloroformate (0.27 mL, 2.09 mmol) were added. The reaction was stirred for 20 minutes and a solution of 4-aminobenzyl alcohol (321.85 mg, 2.61 mmol) in dry THF was added. The reaction mixture was stirred for 2 hours and was monitored by TLC (EtOAc 100%). Upon completion of the reaction, the solvent was removed under reduced pressure and the crude product was purified using column chromatography on silica gel (EtOAc 100%) to give compound 3 (835 mg, 82%) as a yellow solid (FIG. 4).

Preparation of Compound 4:

Compound 3 (353.6 mg, 0.60 mmol) was dissolved in dry THF and the solution was cooled to 0° C. Then DIPEA (0.42 mL, 2.42 mmol), PNP-chloroformate (367 mg, 1.82 mmol) and a catalytic amount of pyridine were added. The reaction was stirred for 2 hours and monitored by TLC (EtOAc:Hex 3:1). Upon completion of the reaction, the solvent was removed under reduced pressure. The crude product was diluted with EtOAc and washed with saturated NH4Cl. The organic layer was dried over magnesium sulfate and the solvent was removed under reduced pressure. The crude product was purified using column chromatography on silica gel (EtOAc:Hex 3:1) to give compound 4 (453.2 mg, 79%) as a white solid (FIG. 4).

Preparation of Compound 5:

Compound 4 (360.3 mg, 0.48 mmol) was dissolved in dry DCM. Then PTX (494.06 mg, 0.57 mmol) and DMAP (70.61 mg, 0.57 mmol) were added. The reaction mixture was stirred for 8 hours and monitored by TLC (EtOAc 100%). Upon completion of the reaction, the solvent was removed under reduced pressure and the crude product was purified using column chromatography on silica gel (EtOAc 100%) to give compound 5 (662 mg, 94%) as a white solid (FIG. 4).

Preparation of HPMA Copolymer-PTX-FK (Alloc):

Compound 5 (12 mg, 7.57 µmol) was dissolved in 0.5 mL TFA and stirred for 2 minutes at 0° C. The excess of acid was removed under reduced pressure and the crude amine salt was dissolved in 0.5 mL DMF. HPMA copolymer (26.3 mg, ONp=8.32 µmol) was added, followed by the addition of $Et_3N$ (3 µL). The reaction mixture was stirred for 12 hours and the solvent was removed under reduced pressure.

Free PTX, FK and ONp were removed by FPLC using XK26/70 column with Sephadex LH20 column (MeOH 100%, 1 mL/1 minute) to give the alloc protected HPMA copolymer-PTX-FK as a white solid (20 mg) (FIG. 4).

Preparation of HPMA Copolymer-PTX-FK:

Alloc protected HPMA copolymer-PTX-FK (30 mg, alloc=max. 9.9 µmol) was dissolved in DMF (1 mL). Then acetic acid (2.71 µL, 47.4 µmol), $Bu_3SnH$ (30.6 µL, 113 µmol) and a catalytic amount of $Pd(PPh_3)_4$ were added. The reaction mixture was stirred for 2 hours and was concentrated under reduced pressure, followed by addition of 10 mL of acetone. The precipitate was filtered out and washed with acetone several times. The crude product was purified by HPLC using XK26/70 column with Sephadex LH2O (MeOH 100%, 1 mL/1 minute) to give HPMA copolymer-PTX-FK (20 mg) as a white solid (FIGS. 1D and 4).

Figure 1D:
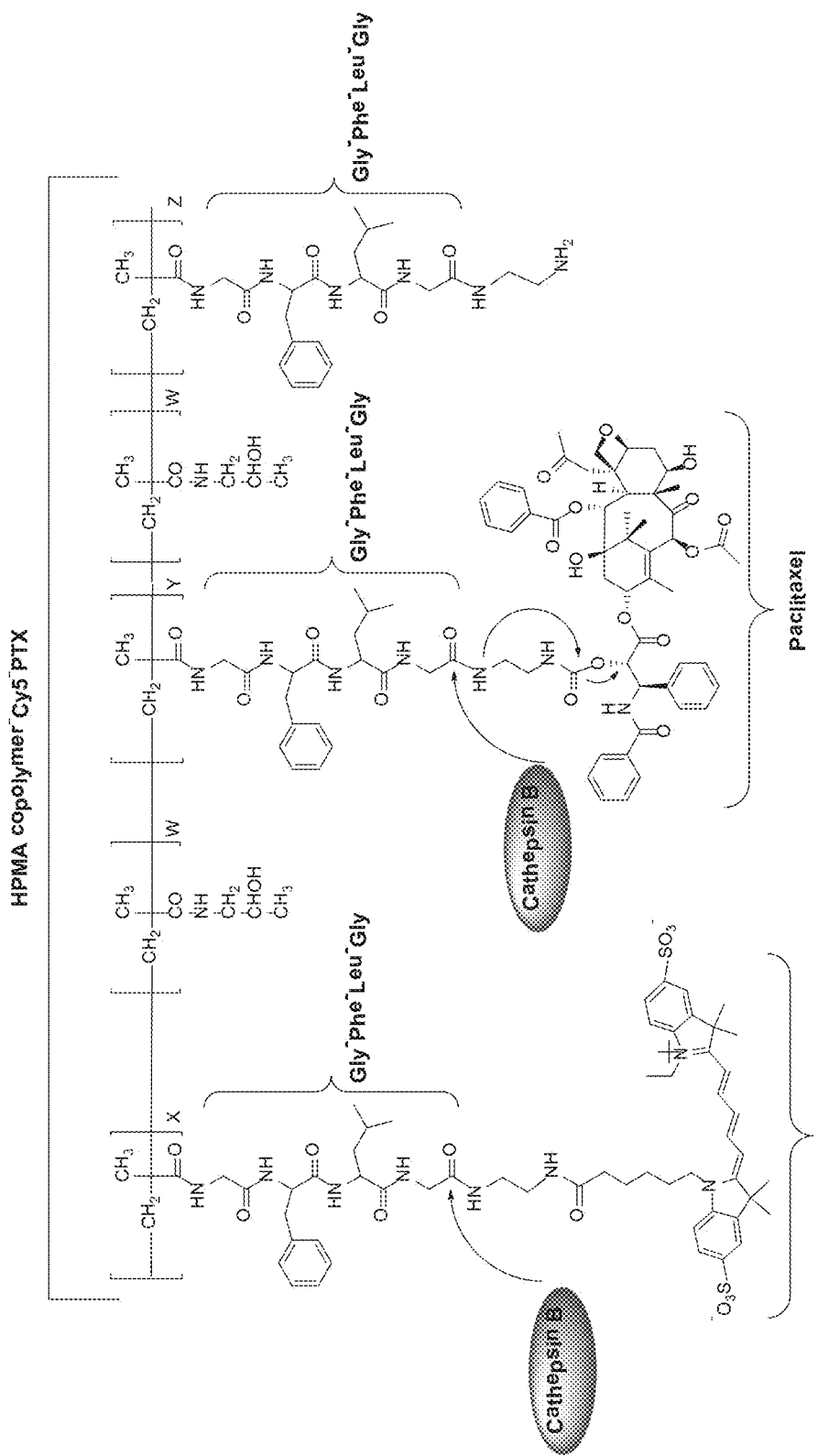

Synthesis of HPMA Copolymer-PTX-Cy5 Conjugate:

The structure of exemplary HPMA copolymer-PTX-Cy5 is depicted in FIG. 1D. The synthesis of the HPMA copolymer-PTX-Cy5 conjugate is depicted in FIG. 5.

Cy5-COOH was synthesized as described hereinabove. Next, Cy5-COOH fluorophore was conjugated with HPMA copolymer-GFLG-en in two-step synthesis. First, Cy5-COOH (15.1 mg, 0.023 mmol) was dissolved in 0.7 mL anhydrous N,N-Dimethylformamide (DMF). N-Hydroxysuccinimide (NHS) (5.3 mg, 0.046 mmol) and N,N'-dicyclohexylcarbodiimide (DCC) (9.5 mg, 0.046 mmol) were added in order to activate the free carboxylic group of the fluorophore, for further coupling to the HPMA copolymer. The reaction mixture was stirred at room temperature (RT) in dark for 12 hours. Then, HPMA-GFLG-en copolymer (21.1 mg, 0.114 mmol) was dissolved in 0.5 mL anhydrous DMF and added to the reaction mixture. At reaction termination, PTX-ONp, prepared as described hereinabove, was added to the reaction round bottom flask. Following the reaction completion (as monitored by High Pressure Liquid Chromatography (HPLC) (UltiMate® 3000 Nano LC systems, Dionex), the precipitate was washed with acetone and dried under vacuum.

Free Cy5 and PTX-ONp were removed by FPLC using XK26/70 column with Sephadex LH2O column (MeOH 100%, 1 mL/1 min); UV detection.

The conjugate was isolated by freeze-drying.

Cy5 loading was determined using SpectraMax M5$^e$ multi-detection reader. The absorbance of conjugated Cy5 was measured and compared to that of free Cy5.

The PTX content of the HPMA copolymer-PTX-Cy5 conjugate was determined by HPLC analysis. The PTX content was determined against a calibration curve for free PTX.

Quenching efficiency was expressed as a percentage of the fluorescence intensity of the HPMA copolymer-Cy5 conjugate ($\lambda_{Em}$=670 nm) compared with the emission of the free Cy5 at the equivalent concentration, as is detailed hereinunder.

Figure 1E:
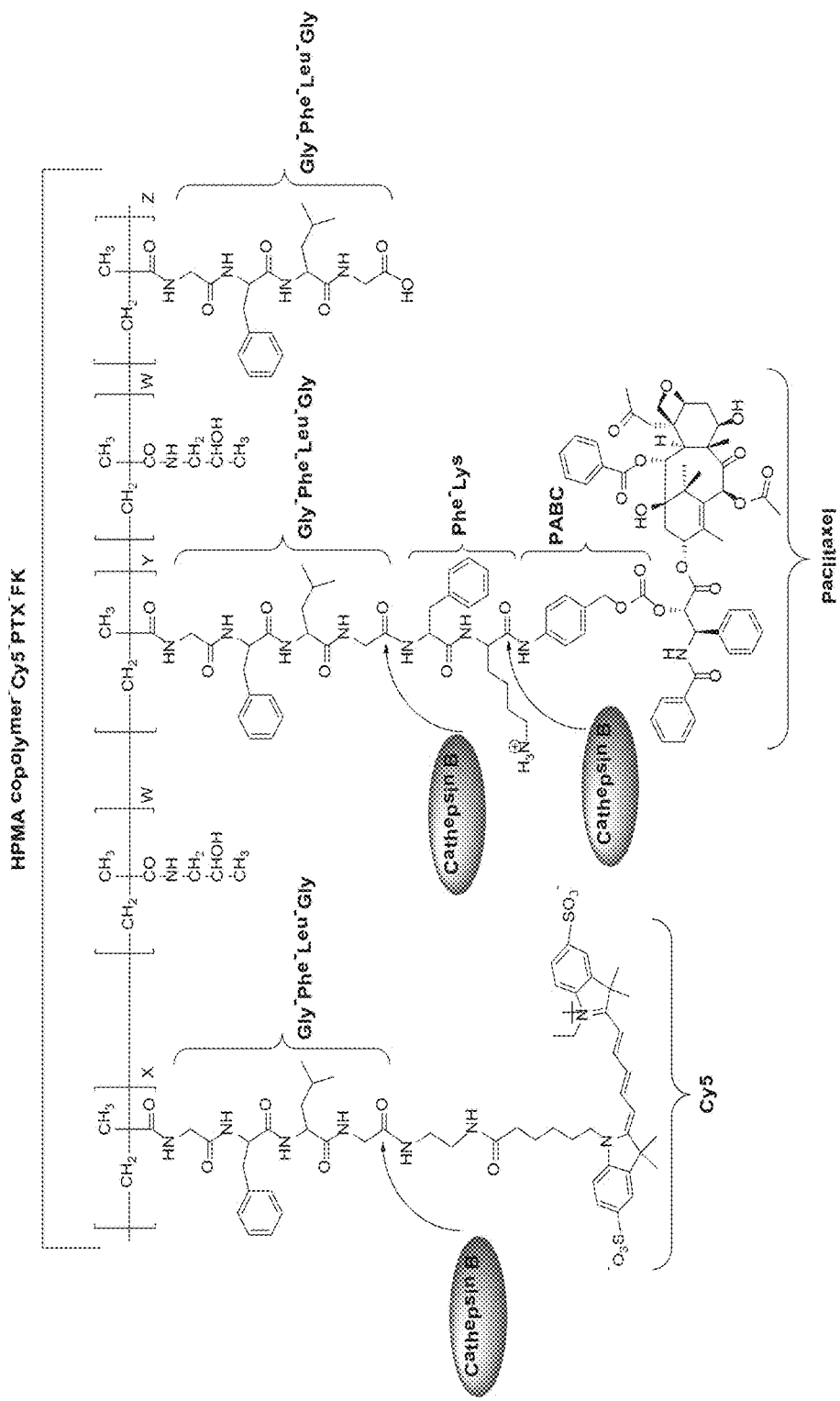

Synthesis of HPMA Copolymer-PTX-FK-Cy5 Conjugate:

The structure of an exemplary HPMA copolymer-PTX-FK-Cy5 is shown in FIG. 1E. The synthesis of the HPMA copolymer-PTX-FK-Cy5 is illustrated in FIG. 6.

Previously synthesized L-Boc-Phe-ONp was reacted with L-Lys(alloc)-OH, as described hereinabove, to give dipeptide compound 2. The latter was conjugated with 4-aminobenzyl alcohol as described hereinabove to generate alcohol compound 3. Activation of alcohol compound 3 with p-nitrophenyl chloroformate as described hereinabove afforded carbonate compound 4, which was reacted with PTX as described hereinabove to yield compound 5. Deprotection of Boc-Cy5 with TFA, followed by conjugation with HPMA copolymer-Gly-Phe-Leu-Gly-ONp gave compound 6. Deprotection of Boc-Phe-Lys(alloc)-PABC-PTX 5 with TFA, followed by conjugation with HPMA copolymer-Cy5 6 gave compound 7. Both Gly-Phe-Leu-Gly and Phe-Lys cathepsin B-cleavable peptides were used in order to provide convenient conjugation chemistry, longer spacer and higher probability of cleavage. Deprotection of the alloc residue of 7 afforded the desired conjugate 1 (see, FIG. 1E).

Preparation of Compound 6:

Cy5 (20 mg, 25.41 µmol) was dissolved in 0.5 mL TFA and the solution was stirred for 5 minutes at 0° C. The excess of acid was removed under reduced pressure and the crude amine salt was dissolved in 0.5 mL DMF. HPMA copolymer-Gly-Phe-Leu-Gly-ONp (24 mg, ONp=12.7 µmol) was added followed by the addition of $Et_3N$ (5 µL). The reaction mixture was stirred for 12 hours and the solvent was removed under reduced pressure. The crude product was used for the next step without further purification (FIG. 6).

Preparation of Compound 7:

Compound 5 (12 mg, 7.57 µmol) was dissolved in 0.5 mL TFA and the solution was stirred for 2 minutes at 0° C. The excess of acid was removed under reduced pressure and the crude amine salt was dissolved in 0.5 mL DMF. Compound 6 (26.3 mg, ONp=8.32 µmol) was added followed by the addition of $Et_3N$ (3 µL). The reaction mixture was stirred for 12 hours and the solvent was removed under reduced pressure.

Free amine (Cy5 and PTX FK), ONp and Cy5 were removed by FPLC using XK26/70 column with Sephadex LH2O column (MeOH 100%, 1 mL/1 min) to give compound 7 as a white solid (20 mg) (FIG. 6).

Preparation of Compound 1:

Compound 7 (30 mg, alloc=max. 9.9 µmol) was dissolved in DMF (1 mL). Then acetic acid (2.71 µL, 47.4 µmol), $Bu_3SnH$ (30.6 µL, 113 µmol) and a catalytic amount of $Pd(PPh_3)_4$ were added. The reaction mixture was stirred for 2 hours and was concentrated under reduced pressure, followed by addition of 10 mL of acetone. The precipitate was filtered out and washed with acetone several times. The crude product was purified by HPLC using XK26/70 column with Sephadex LH2O (MeOH 100%, 1 mL/1 min) to give compound 1 (20 mg) as a white solid (FIG. 1E).

Example 2

Chemical Synthesis of PGA-PTX-Cy5 Conjugate

The synthesis of PGA-PTX-Cy5 conjugate is depicted in FIGS. 7A-D and 8A-B.

PGA was synthesized via the N-carboxyanydride (NCA) polymerization of glutamic acid, as shown in FIGS. 7A-C. The synthesized PGA was dissolved in anhydrous N,N-Dimethylformamide (DMF) and mixed with carbonyldiimidazole (CDI) coupling reagent in order to activate the free polymer's carboxyl groups. The reaction mixture was stirred at room temperature for 4 hours in basic environment. Then PTX was dissolved in anhydrous DMF and added to the reaction mixture to obtain the PGA-PTX conjugate, through formation of an ester bond. The reaction mixture was stirred overnight at 4° C. The reaction, shown in FIG. 7D, was followed by High Pressure Liquid Chromatography (HPLC) (UltiMate® 3000 Nano LC systems, Dionex). At the end of the reaction the precipitate was washed with acetone:chloroform (1:4) solution and dried under vacuum.

The drug loading (x, FIG. 7D) on a polymer was determined using a High Pressure Liquid Chromatography (HPLC) (UltiMate® 3000 Nano LC systems, Dionex).

The obtained PGA-PTX conjugate was dissolved in an anhydrous DMF and mixed again with carbonyldiimidazole (CDI) coupling reagent in order to activate the unoccupied polymer's carboxyl groups. The reaction mixture was stirred at room temperature for 4 hours. The solution was removed to a round-bottom flask containing Cy5-NH$_2$, which was treated with Trifluoroacetic Acid (TFA) to remove a protecting group (Boc) from it (See, FIG. 8A). The reaction was stirred overnight at room temperature in basic environment. The reaction, shown in FIG. 8B, was followed by High Pressure Liquid Chromatography (HPLC) (UltiMate® 3000 Nano LC systems, Dionex). Upon completion of the reaction the precipitate was washed with acetone:chloroform (4:1) mixture and dried under vacuum.

In order to remove the excess of free fluorophore, the residue was dissolved in NaHCO$_2$ 0.2 M buffer and dialyzed for 1 day at 4° C. (MWCO 6-8 kDa) against DI water. The final purification of the conjugate by size exclusion chromatography (SEC) was performed using AKTA/FPLC system (Pharmacia/GE Healthcare), HiTrap Desalting columns (Sephadex G-25 Superfine) in DDW, flow rate 1.0 ml/min; UV detection.

Cy5 loading (y in FIG. 8B) was determined using SpectraMax M5$^e$ multi-detection reader. The absorbance of conjugated Cy5 was measured and compared to that of free Cy5. Quenching efficiency was expressed as a percentage of the fluorescence intensity of the PGA-PTX-Cy5 conjugate ($\lambda_{Em}$=670 nm) compared with the emission of the free Cy5 at the equivalent concentration.

Preparation of PGA:

The starting PGA was synthesized via the N-carboxyanhydride (NCA) polymerization of glutamic acid. First, NCA glutamate was prepared as described in FIG. 7A with a proposed mechanism. H-Glu(OBzl)-OH was used as a starting material, in which the γCOOH is protected with O-benzyl (OBzl). Then, hexylamine (denoted as R$_2$—NH$_2$) initiated polymerization of the NCA of γ-benzyl-L-glutamate (FIG. 7B).

PGA was characterized by GPC, zetasizer and $^1$H-NMR. Following deprotection of the OBzl protecting group in TFA/HBr/AcOH mixture, the carboxyl group becomes available for coupling to PTX and Cy5.

Preparation of PGA-PTX:

The anti-cancer drug PTX was conjugated to the PGA polymeric backbone via its carboxyl groups, as depicted in FIG. 7D. First, PGA functional groups were activated by carbonyldiimidazole (CDI) coupling in anhydrous DMF, and then PTX was added to an activated reaction mixture to obtain the PGA-PTX conjugate, through a formation of an ester bond.

As PGA is a substrate of a lysosomal enzyme cathepsin B, upon endocytosis of the conjugate to the cells it should be cleaved, and result in release of free PTX in the tumor interstitium.

Preparation of PGA-PTX-Cy5:

Cy5, in a sufficient amount, was conjugated to the polymeric backbone of PGA, to achieve a fluorophore self-quenching. The Cy5 is attached to the PGA via an amide bond. The polymeric backbone cleavage by the cathepsin B enzyme should release the fluorophore from the conjugate, thus removing the self-quenching and activating the fluorescence.

PGA-PTX-Cy5 conjugate was synthesized as described in FIGS. 8A-B. First, the unoccupied carboxylic groups of PGA were activated with CDI coupling agent, supported by DMAP as a catalyst in a basic environment and then a Cy5-NH$_2$, after the protecting group (Boc) removal (FIG. 8A), was mixed with the activated PGA-PTX polymeric conjugate, to form an amide bond and obtain the desired conjugate (FIG. 8B).

Example 3

Characterization and Activity of HPMA Copolymer-PTX Conjugate

Cathepsin B-Mediated Degradation and Release:

Cathepsin B-mediated degradation and release of PTX from HPMA copolymer-PTX over time is described in FIG. 9B. PTX concentration was increased as a function of time and expressed by area under the curve (AUC), and represents a satisfactory efficiency of cathepsin B activity. Release kinetics of PTX release show a complete release from HPMA copolymer after approximately 80 hours.

Dynamic Light Scattering and Zeta Potential of HPMA Copolymer-PTX Conjugate:

The hydrodynamic diameter size distribution and zeta-potential of HPMA copolymer-PTX conjugate was determined using a ZetaSizer analyzer. Table 1 presents physicochemical characterization of HPMA copolymer-PTX conjugate.

TABLE 1

| Conjugate | Mw (kDa)$^a$ | Size (nm)$^b$ | Zeta Potential (mV)$^b$ | Total PTX Loading (mol %)$^c$ |
|---|---|---|---|---|
| HPMA-PTX | 37.70 | 11.99 | 3.69 | 4.0 |

$^a$theoretical value,
$^b$determined by Zetasizer in 10% PBS (1 mg/mL),
$^c$determined by analytical HPLC at λ = 270 nm.

The mean hydrodynamic diameter was 11.99 nm and the zeta potential value was 3.69 mV (Table 1). As expected, HPMA copolymer-PTX has a neutral charge and its size is in the nano range, which enables its targeting to the tumor via the EPR effect.

HPMA Copolymer-PTX Conjugate Inhibits the Proliferation of 4T1 Mammary Adenocarcinoma and MDA-MB-231 Cancer Cell Lines:

The mitotic inhibitor PTX is a potent cytotoxic agent approved as first line therapy for breast cancer. The cytotoxic effect of the conjugate was evaluated on murine 4T1 mammary adenocarcinoma cells. The obtained data are presented in FIG. 10A. As shown therein, the proliferation of 4T1 cells was inhibited by HPMA copolymer-PTX conjugate with an $IC_{50}$ of about 15 µM (see, FIGS. 10A and 10D).

HPMA copolymer alone served as control and was inert at all the concentrations tested (data not shown), in agreement with previously published data [Duncan et al., 2001, supra]. $IC_{50}$ for free PTX was about 35 nM (see, FIG. 10D). The difference in $IC_{50}$ between the free drug and the conjugate can be attributed to the slow release kinetics of the drug from the carrier.

These results are in accordance with previous reports showing the cytotoxic effect of an analogous HPMA copolymer-PTX conjugate on breast cancer cells [Miller, K., et al., Angew Chem Int Ed Engl, 2009. 48(16): p. 2949-54; Miller, K., et al., Mol Pharm, 2011. 8(4): p. 1052-62].

HPMA Copolymer-PTX Exhibits Anti-Angiogenic Effect In Vitro:

The anti-angiogenic effect of PTX on endothelial cells was previously demonstrated [Miller et al., 2009 and 2011, supra; Clementi, C., et al., Mol Pharm, 2011. 8(4): p. 1063-72]. These studies have demonstrated inhibitory effect of PTX on different stages of the angiogenic cascade-proliferation, migration and formation of tube-like structures. Since endothelial cells that construct the tumor vasculature, also overexpress cathepsin B, the inhibitory effect of the herein described cathepsin B-dependent delivery system on HUVEC proliferation was evaluated.

The obtained results are presented in FIGS. 10B and 10D, and indeed show that the HPMA copolymer-PTX conjugate exhibited cytotoxic effect on HUVEC proliferation with an $IC_{50}$ of about 90 nM compared to about 2 nM of the free drug. Similarly to the aforementioned experiments performed on 4T1 cells, HPMA copolymer alone served as control and was nontoxic at all the concentrations tested (data not shown).

The results demonstrate that PTX maintained its cytotoxic activity in vitro upon conjugation to HPMA copolymer and that a cathepsin B-dependent release mechanism is efficient for active targeting of HPMA copolymer-PTX to breast cancer and its vasculature overexpressing the enzyme in vivo.

Example 4

Characterization and Activity of HPMA Copolymer-PTX-FK Conjugate

The chemical structure of HPMA copolymer-PTX-FK conjugate is presented in FIG. 1D. PTX was conjugated to HPMA copolymer through a Gly-Phe-Leu-Gly (GFLG) linker and an addition of Phe-Lys-PABC linker respectively, both cleavable by cathepsin B enzyme.

The conjugation to the HPMA copolymer was a two-step procedure in which PTX was first attached to the FK-PABC linker and then conjugated to HPMA copolymer-GFLG-ONp (FIG. 4).

The resulting conjugate was water-soluble, PTX-FK loading was 1.12 mol % (2.02 PTX molecules per polymeric chain).

Cathepsin B-mediated degradation and release of PTX from HPMA copolymer-PTX-FK over time is described in FIG. 9A. PTX concentration was increased as a function of time and expressed by area under the curve (AUC), and presents a satisfactory efficiency of cathepsin B activity. Release kinetics of PTX show a complete release from HPMA copolymer after approximately 50 hours.

HPMA Copolymer-PTX-FK Conjugate Inhibits the Proliferation of MDA-MB-231 Human Mammary Adenocarcinoma Cancer Cell Line:

The cytotoxic effect of the conjugate was evaluated on human MDA-MB-231 mammary adenocarcinoma cells. The obtained data is presented in FIGS. 10C and 10D. As shown therein, the proliferation of MDA-MB-231 cells was inhibited by HPMA copolymer-PTX-FK conjugate with an $IC_{50}$ of 100 nM. HPMA copolymer alone served as control and was inert at all the concentrations tested (data not shown), in agreement with previously published data.

$IC_{50}$ for free PTX was about 0.5 nM. The difference in $IC_{50}$ between the free drug and the conjugate can be attributed to the slow release kinetics of the drug from the carrier. These results are in accordance with previous reports showing the cytotoxic effect of an analogous HPMA copolymer-PTX conjugate on breast cancer cells [Miller et al. supra].

Example 5

Characterization and Activity of HPMA Copolymer-SQ-Cy5 Conjugate

The chemical structure of the HPMA-copolymer-GFLG-en-Cy5 conjugate, also referred to herein as HPMA copolymer-SQ-Cy5 conjugate (SQ=self-quenching), or simply as HPMA copolymer-Cy5, is presented in FIG. 1A.

HPMA-copolymer-GFLG-en-Cy5 conjugate was synthesized with 3.8 mol % loading (7.5 dye molecules per polymeric chain) and its fluorescence spectrum was characterized, in order to evaluate both the self-quenching of the conjugated fluorophore and its biodegradability by cathepsin B.

As shown in FIG. 11A, HPMA copolymer-SQ-Cy5 conjugate exhibits significant self-quenching; the fluorescent signal of the HPMA copolymer-SQ-Cy5 conjugate was reduced compared to an equivalent concentration of free Cy5. At the signal's linear range, the two linear trend lines slopes of free Cy5 and HPMA copolymer-Cy5 were compared and a reduction of 54% therebetween was obtained. In addition, after the signal reached saturation, a reduction of about 80% was observed.

In order to evaluate the increase in fluorescence intensity due to enzymatic cleavage, HPMA copolymer-SQ-Cy5 was incubated in the presence of cathepsin B and release of Cy5 was assessed by fluorescence signal. The results are presented in FIG. 11B, and show that the measured fluorescence intensity was dramatically increased over time and plateaued after about 100 hours. In the absence of the enzyme, there was no increase in fluorescent signal.

A HPMA copolymer-SQ-Cy5, with loading of 3.8 mol % Cy5, exhibited satisfactory self-quenching properties and activation by cathepsin B. Under physiological conditions, the conjugate is relatively optically silent in its quenched state (i.e., turn-OFF), and becomes highly fluorescent after enzymatic cleavage of the GFLG linker by cathepsin B. It is postulated that the loading of the fluorophore affects the optimal performance of the conjugate. At low fluorophore loading, only limited quenching may occur, whereby at high fluorophore loading, the Turn-ON may not occur as the enzyme may not reach its target site [Melancon, M. P., et al., Pharm Res, 2007. 24(6): p. 1217-24].

In Vitro Turn-on Capacity on HPMA-SQ-Cy5 Conjugate:

As shown in FIG. 11C, incubation of HPMA copolymer-GFLG-Cy5 in cultured MDA-MB-231 cells resulted in significantly higher fluorescence signal intensity than that observed in culture non-treated MDA-MB-231 cells during a period of 0.5-48 hours.

In Vivo Characterization of HPMA Copolymer-SQ-Cy5 Cathepsin-Dependent Release:

As mentioned above, overproduction of cathepsin B in vivo is associated with breast carcinoma, both tumor cell population and tumor endothelium. Thus, the ability of the probe conjugate to exhibit Turn-ON properties, and to image endogenously produced cathepsin B in a murine model of 4T1 breast adenocarcinoma tumors was evaluated.

Mice bearing approximately 100 mm$^3$ tumors were injected intra-tumorally with 0.1 mM free Cy5 and equivalent Cy5 dose of HPMA copolymer-SQ-Cy5. Injected mice were imaged using CRI Maestro™ non-invasive fluorescence imaging systems over time for approximately 8 hours.

The obtained data is presented in FIGS. 12A and 12B. The initial fluorescent signal of HPMA copolymer-SQ-Cy5 is significantly lower than that of free Cy5, which exhibits the self-quenching properties of high-loaded Cy5. In addition, FIG. 12A clearly shows an increase of 1.8-fold change in fluorescence signal within 1 hour of injection. Interestingly, HPMA copolymer-SQ-Cy5 exhibited improved biocompatibility for in vivo florescence imaging. While the free Cy5 bleached almost completely about 3 hours following injection, although lower, the fluorescent signal of the conjugated Cy5 retained for long period of time (FIG. 12A). Consequently, HPMA copolymer-SQ-Cy5 may represent a suitable approach for in vivo imaging of endogenous cathepsin B in tumor, to indicate on drug release in real time and for tumor monitoring over time.

HPMA Copolymer-SQ-Cy5 Exhibit Improved Pharmacokinetics Profile in Mice:

To assess whether HPMA copolymer-PTX exhibits preferable accumulation and release at the tumor site once injected systemically, HPMA copolymer-SQ-Cy5 was administered into mice and its pharmacokinetics profile was utilized to deduce on HPMA copolymer-PTX pharmacokinetics profile.

Mice bearing about 300 mm$^3$ 4 T1 tumors were administered via the tail vein with HPMA copolymer-Cy5 (10 µM; 200 µl). It was hypothesized that conjugation will result in half-life prolongation and tumor specific accumulation and release.

As shown in FIG. 13A, and in accordance with this hypothesis, HPMA copolymer-SQ-Cy5 demonstrated accumulation in the tumor. Mice were imaged over time and fluorescent signal in the tumor was measured. As described in FIG. 13B, at the first 3 hours following administration, HPMA copolymer-Cy5 exhibited no preferable accumulation at the tumor. However, after 4 hours increased fluorescent signal in the tumor was measured.

Next, healthy organs (heart, lungs, liver, spleen and kidneys) and tumors were resected from mice injected with the conjugate at different time points and the fluorescent intensity was evaluated. The obtained data is presented in FIG. 13C and show that increased fluorescent signal was measured within tumors 12 hours following administration. HPMA copolymer-SQ-Cy5 was hardly detectable in the heart and spleen. Interestingly, increased fluorescent signal was also measured in the liver and kidneys. However, since the fluorescent signal in these organs did not increase over time, it can be concluded that Cy5 was not released from HPMA copolymer, hence, PTX will not be released and fluorescent as well. After several hours, the signal decreased in these organs and it was only increased over time within tumors. To conclude, HPMA copolymer-SQ-Cy5 exhibited preferable accumulation in the tumor, liver and kidneys, but Cy5 was released, presumably by enzymatic cleavage, only within tumor cells expressing cathepsin B.

Example 6

Characterization and Activity of HPMA Copolymer-PTX-Cy5 and HPMA Copolymer-PTX-FK-Cy5 Conjugates In HPMA copolymer-PTX-Cy5 conjugate, also referred to herein as HPMA copolymer-SQ-Cy5-PTX, both Cy5 and PTX were conjugated to HPMA copolymer through a Gly-Phe-Leu-Gly (GFLG) linker, cleavable by cathepsin B enzyme. For HPMA copolymer-PTX-FK-Cy5, also referred to herein as HPMA copolymer-SQ-Cy5-PTX-FK, both Cy5 and PTX were conjugated to HPMA copolymer through a Gly-Phe-Leu-Gly (GFLG) linker and an addition of Phe-Lys-PABC linker, respectively, cleavable by cathepsin B enzyme. Characterization of HPMA copolymer-SQ-Cy5-PTX and HPMA copolymer-SQ-Cy5-PTX-FK conjugates show an increase in fluorescence following incubation with cathepsin B, as presented in FIGS. 14A-B. FIG. 14C presents comparative plots showing that fluorescence intensity ($\lambda_{Ex}$=650 nm) decreased with increasing load of Cy5.

Example 7

Characterization and Activity of PGA-PTX-Cy5 Conjugate

Characterization:

To characterize the conjugate, its absorption and fluorescence were evaluated. Cy5 loading on the conjugate was calculated by spectroscopy analysis.

In addition, these conjugate are substrate for the enzyme cathepsin B. When mixing the conjugate with the enzyme (in a suitable buffer with a low pH), the enzyme should cleave the conjugate and release the attached moieties. The enzymatic reaction was followed using HPLC and spectrophotometer. The absorption spectrum of the PGA-PTX-Cy5 conjugate relative to the absorption spectrum of the free Cy5 is presented in FIG. 15A. As shown in the emission spectrum (FIG. 15B), a fluorescent signal observed for the conjugates of 4 mol % and 7.5 mol % Cy5 loading is significantly lower relative to a signal emitted from an unconjugated Cy5. The fluorescence intensity decreases as Cy5 loading on a polymer increases.

Cy5 release from the conjugate was also monitored by measuring the change in the fluorescence intensity at sequential time points. The fluorescence measurements were carried out at excitation wavelengths of 650 nm using SpectraMax M5$^e$ multi-detection reader. Samples (50 µl) were collected every 24 hours (up to 160 hours) and immediately analyzed. The incubation of the PGA-PTX-Cy5 conjugate with cathepsin B enzyme, showed an increase in emitted fluorescent signal as a function of time. In the absence of cathepsin B, almost no increase in fluorescence was observed (FIG. 15C). This data shows a self-quenching ability of PGA-PTX-Cy5 conjugate, since while the conjugate is intact the fluorescent signal is significantly silent, while when the Cy5 is released from the PGA polymeric backbone in the presence of cathepsin B, there is no longer self-quenching effect and the fluorescent signal increases.

Release of PTX from the conjugate incubated with cathepsin B enzyme over time was monitored by reversed phase (RP) HPLC. UltiMate® 3000 Nano LC systems (Dionex), equipped with 3000 pump, VWD-3000 UV-Vis detector and Chromeleon® 6.80 software. The column in use was Phenomenex Jupiter 5μ 250×4.60 mm C-18 300A. Chromatographic conditions were: flow: 1.0 ml/min, gradient: 20% to 100% solution B in 20 minutes (sol. A—0.1% TFA in water; sol. B—0.1% TFA in acetonitrile (MeCN)). Samples (50 μl) were collected simultaneously with samples for Cy5 release determination, every 24 hours (up to 160 hours). To each sample 150 μl of methanol added and immediately analyzed. The AUC of a PTX peak was increase over the time as shown in FIG. 15D.

Anti-Proliferative Activity:

The cytotoxic effect of the conjugate was evaluated on human MDA-MB-231 mammary adenocarcinoma cells, on murine 4T1 adenocarcinoma cells and on human WM239A melanoma cells. As shown in FIGS. 16A-D, the proliferation of all cell lines was inhibited by PGA-PTX-Cy5 conjugate with an $IC_{50}$ of about 40 nM for MDA-MB-231 cells, an $IC_{50}$ of about 650 nM for 4T1 cells and with $IC_{50}$ of about 80 nM for WM239A cells.

Figure 16B:
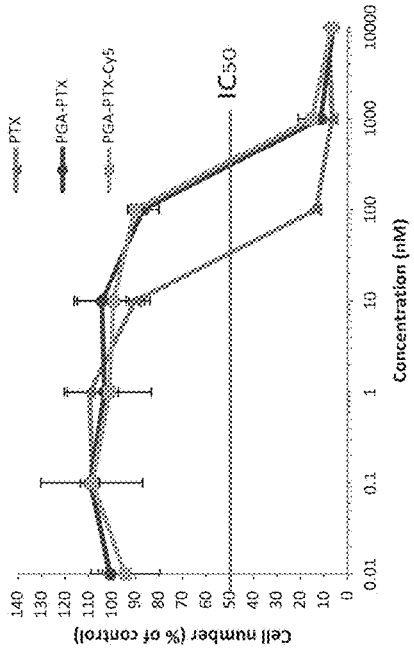
Figure 16D:
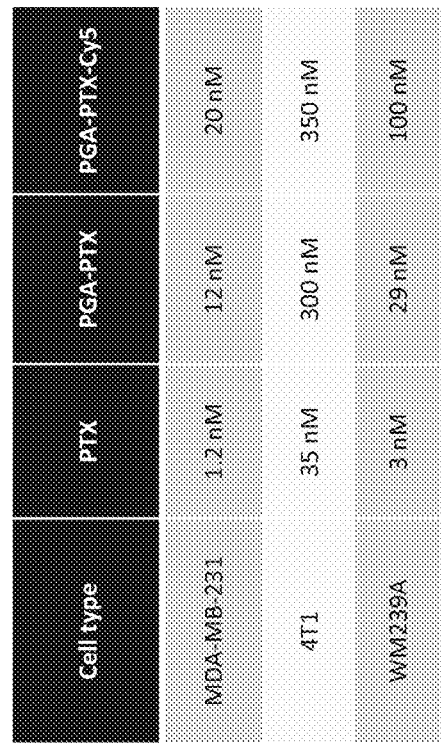
Figure 16A:
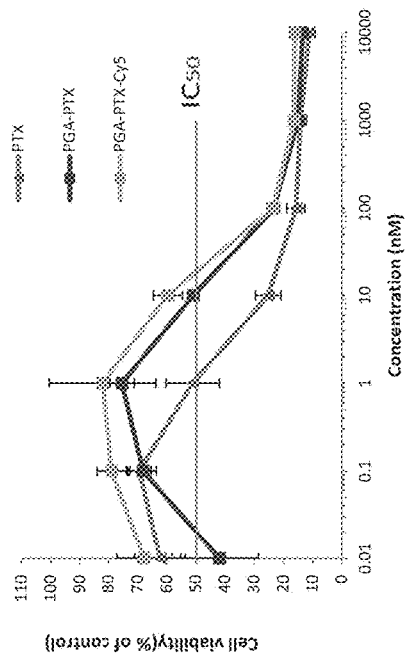
Figure 16C:
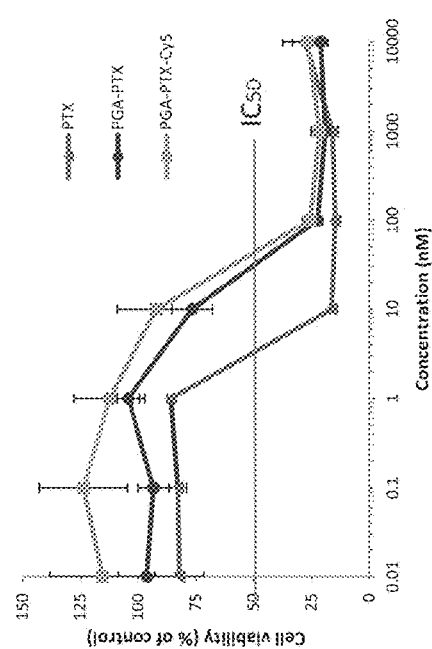

Free Paclitaxel and PGA-PTX polymeric conjugate served as controls. $IC_{50}$ for free PTX was about 2 nM in case of MDA-MB-231 cells, about 60 nM in case of 4T1 cells and about 5 nM in case of WM239A cells (FIG. 16D). The difference in $IC_{50}$ between the free drug and the conjugate can be attributed to the slow release kinetics of the drug from the carrier. These results are in accordance with previous reports showing the cytotoxic effect of an analogous PGA-PTX conjugate on breast cancer cells.

PGA-PTX-Cy5 Conjugate Inhibits the Migration of HUVEC:

The migration of HUVEC in the presence of PGA-PTX-Cy5 conjugate was evaluated using the scratch assay. The method is based on the observation that, upon creation of a new artificial gap, so called "scratch", on a confluent cell monolayer, the cells on the edge of the newly created gap will move toward the opening to close the "scratch" until new cell-cell contacts are established again. Following 24 hours incubation of HUVEC in 6 wells plate (500,000 cells per well) the cells were treated with the conjugate and the different controls (such as: PTX, PGA-PTX and no treatment). At time zero (t=0) images were taken by phase-contrast microscope in a reference point. Following another 12 h of incubation, images of the reference point were taken again. The samples were analyzed quantitatively by ImageJ software. The PGA-PTX-Cy5 conjugate, at PTX-equivalent concentrations of 20 nM inhibited efficiently the migration of HUVEC by 36% of gap closure (FIG. 17). As expected, PTX alone, which is known to be anti-angiogenic at low doses, showed higher inhibitory effect of 20% of gap closure.

The effect of PGA-PTX-Cy5 conjugate on the ability of HUVECs to form capillary-like tube structures on matrigel was also evaluated. As previously reported, such an assay can emulate the capability of endothelial cells to form vascular networks in vivo. HUVEC were incubated in the presence of PGA-PTX-Cy5 conjugate, free PTX, free Cy5, and PGA, and in absence of treatment, for 8 hours, pictured and quantitatively analyzed. The obtained data is presented in FIGS. 18A-B. As shown therein, PGA-PTX-Cy5 at PTX load equivalent of 20 nM inhibited the tubular structures formation by about 40%, compared to untreated cells used as negative control.

Example 8

Syntheses of HPMA Copolymer Conjugates by RAFT Polymerization

Reversible addition-fragmentation chain transfer (RAFT) polymerization is a versatile controlled/"living" free radical polymerization technique resulting in predetermined molecular weight with narrow polydispersity. This technique enables the theoretical calculation of molecular weight of the polymers by the ratio of monomer concentration to chain transfer agent concentration and the conversion of the polymerization. Additional advantage is the ease of manufacturing since the synthesis is carried out in a one-pot reaction.

Functional monomers were therefore designed and synthesized for RAFT polymerization of HPMA copolymer conjugates for theranostics. This design of RAFT synthesized copolymer conjugates benefits from controlled polymerization and a lower polydispersity that may improve its biodistribution and accumulation at the tumor site, and further, the higher amount of the activatable diagnostic moiety can lead to an increased signal emitted upon the probe activation to a Turn-ON state.

Preparation of Functional Monomers:

The syntheses of N-(N-Boc-ethylenediamine) methacryloylglycylglycylamide (MA-Gly-Gly-diamine-Boc) and methacryloylglycylphenylalanylleucylglycyl-p-aminophenylcarbonate p-nitrophenyl ester (MA-Gly-Phe-Leu-Gly-PABC-ONp; MA-GFLG-PABA; MA-Gly-Phe-Leu-Gly-PABA) are shown in FIGS. 19A and 19B, respectively.

Preparation of MA-Gly-Phe-Leu-Gly-OH:

MA-Gly-Phe-Leu-Gly-OH was synthesized by solid phase peptide synthesis (SPPS) and manual Fmoc/tBu strategy using 2 grams of 2-chlorotrityl chloride beads with 80% of loading leading to a yield of 0.88 grams, 95%.

Preparation of MA-Gly-Phe-Leu-Gly PABA:

MA-GFLG-OH (400 mg, 0.815 mmol) was dissolved in dry THF and the solution was cooled to −15° C. Then NMM (90 μL, 0.815 mmol) and isobutyl chloroformate (128 μL, 0.978 mmol) were added. The reaction was stirred for 20 minutes and a solution of 4-aminobenzyl alcohol (151 mg, 1.22 mmol) in dry THF was added. The reaction mixture was stirred for 12 hours and was monitored by TLC (EtOAc 100%). Upon completion of the reaction, the solvent was removed under reduced pressure and the crude product was purified by using column chromatography on silica gel (1-8% MeOH in EtOAc) to give MA-Gly-Phe-Leu-Gly (262 mg, 53%) as a yellow solid. See, FIG. 19B.

Preparation of MA-Gly-Gly-Diamine-Boc:

MA-Gly-Gly-OH was synthesized as described in Rejmanova et al. (1977) *Makromol Chem* 178, 2159-2168, followed by amination that was carried out as follows: MA-Gly-Gly-OH (200 mg, 0.864 mmol), DCC (196.2 mg, 0.951 mmol), NHS (99.5, 10 mmol) were stirred in DMF for 1 hour, then N-(tert-butoxycarbonyl) (Boc)-ethylenediamine (138.5 mg, 0.864 mmol) was added, and the reaction mixture was stirred for 24 hours at room temperature. The product was obtained by precipitation in ethyl ether. See, FIG. 19A.

RAFT Polymerization:

Exemplary synthetic schemes utilizing the above-described functional monomers are presented in FIGS. 20 and 21. A RAFT synthesized HPMA copolymer precursor is obtained, bearing functional groups (ONp and/or $NH_2$-Boc) for facile conjugation of a drug (e.g., paclitaxel) and a fluorescent agent (e.g., Cy5 or FITC).

FIG. 20 presents the chemical structure, two-step synthesis and cleavage mechanism by Cathepsin B of HPMA copolymer-Gly-Phe-Leu-Gly-PABC-Cy5-PTX, an exemplary self-quenching (homo-FRET) based theranostic system synthesized by RAFT polymerization.

FIG. 21 presents the chemical structure, two-step synthesis and cleavage mechanism by Cathepsin B of HPMA copolymer-Gly-Phe-Leu-Gly-PABC-FITC-PTX, an exemplary self-quenching (homo FRET) based theranostic system synthesized by RAFT polymerization.

FIG. 22A presents exemplary synthetic schemes for the preparation of Boc-NH-LG-PABC-PTX, Boc-NH-LG-PABC-Cy5 and Boc-NH-LG-PABC-FITC, useful for conjugating PTX, Cy5 and FITC, respectively, as non-limiting examples of a drug and dyes, to the HPMA copolymer precursor prepared by RAFT polymerization as described hereinabove.

FIG. 22A presents an exemplary synthetic scheme of drug and dye dipeptide-PABC moieties (ivDde-NH-FK-PABC-PTX and ivDde-NH-FK-PABC-Cy5 respectively) useful for conjugation to HPMA copolymer-dipeptide-ONp (Gly-Gly-ONp).

The Cy5 is presented herein as a representative example and can be replaced with other fluorogenic or fluorescent dye moieties or probes such as QCy7 and FRET probes as described herein.

The PTX can also be replaced by other therapeutically active agents as described herein.

Example 9

FRET-Based Polymeric Systems

Förster Resonance Energy transfer (FRET)-based probes are typically composed of a fluorescent dye attached through a cleavable linker to a quencher, as depicted in FIG. 23. Under such circumstances, the excited fluorophore transfers its excitation energy to the nearby quencher-chromophore in a non-radiative manner through long range dipole-dipole interactions. Cleavage of the linker moiety (e.g., by an analyte or enzyme of interest), results in diffusion of the fluorescent dye away from the quencher and thereby in generation of a measurable fluorescent signal.

In some exemplary polymeric FRET-based systems according to the present embodiments, a fluorescent dye is attached to the polymeric backbone units through a cleavable linker. In such cases, upon cleavage of the linker, the fluorescent dye molecules diffuse away from one another, thus generating a measurable fluorescent signal. These systems are referred to herein as self-quenching (SQ) or homo-FRET based systems. When a therapeutically active agent (drug) is also attached to the polymeric backbone, the system is theranostic. Exemplary such systems are described hereinabove and are shown in FIGS. 1A-E, 2, 5, 6, 8B, 20 and 21.

In other exemplary polymeric FRET-based systems, the fluorescent dye is attached to the polymeric backbone units via a cleavable linker, and a quencher is also attached to the polymeric backbone. The quencher can be attached to some of the polymeric backbone units via a linker (preferably a non-cleavable linker). In some embodiments, the fluorescent dye is attached to a portion of the backbone units and the quencher is attached to another portion of backbone units of the polymeric backbone (referred to herein also as FRET mode I). In some embodiments, the quencher is attached to the end of the polymeric backbone (referred to herein also as FRET mode II). Exemplary such systems are described hereinafter and in FIGS. 24-30.

In other exemplary systems, a moiety composed of a fluorescent dye (as a fluorogenic moiety) and a quencher, linked to one another via a linker, is utilized. This moiety can be attached to polymeric backbone units, preferably via a cleavable linker, whereby the system is designed such that upon cleavage of the linker, the fluorescent dye diffuses away from the quencher and a measurable fluorescent signal is generated (referred to herein as FRET mode III). Exemplary such moieties are described hereinafter and are shown in FIGS. 34 and 35, and an exemplary polymeric system comprising such a moiety is shown in FIG. 39. Alternatively, such a moiety can be attached to the end of the polymeric backbone (referred to herein as FRET mode IV). A polymeric system comprising such a moiety is shown in FIGS. 31A-B.

The present inventors have designed exemplary FRET-based polymeric systems and moieties to be incorporated in such systems as follows.

FRET-Based Systems with HPMA Copolymer Conjugates (FRET Modes I and II):

HPMA copolymer conjugates having a drug (e.g., PTX) and a dye (e.g., a fluorogenic moiety such as Cy5 or FITC) attached to the HPMA backbone units, and further comprising a quencher attached to the polymeric backbone are prepared by RAFT polymerization as described in Example 8 hereinabove, and the quencher is attached to the backbone by one of the following approaches: (i) through coupling chemistry of quencher-COOH to a linker of Gly-Gly-$NH_2$ (see, FIGS. 24, 25, 28 and 29; FRET mode I); or (ii) by coupling chemistry of quencher-$NH_2$ to a COOH end-functionalized HPMA-copolymer chain, which results from the rational design of RAFT agent with functional carboxylic acid end group (see, FIGS. 26 and 27; FRET mode II).

FIG. 24 presents the chemical structure, two-step synthesis and cleavage mechanism by cathepsin B of HPMA copolymer-Gly-Phe-Leu-Gly-PABC-Cy5-Quencher-PTX as an illustration for a FRET-based theranostic system synthesized by RAFT polymerization (FRET mode I). The functional monomers and preparation thereof, for synthesizing HPMA copolymer precursor are described in Example 8 hereinabove and in FIGS. 19A and 19B. The functionalized PTX and Cy5 moieties and the preparation thereof are presented in FIGS. 22A-B.

FIG. 25 presents the chemical structure, two-step synthesis and cleavage mechanism by cathepsin B of HPMA copolymer-Gly-Phe-Leu-Gly-PABC-FITC-DR1-PTX as an illustration for a FRET-based theranostic system synthesized by RAFT polymerization (FRET mode I). The functional monomers and preparation thereof, for synthesizing HPMA copolymer precursor are described in Example 8 hereinabove and in FIGS. 19A and 19B. The functionalized PTX and FITC moieties and the preparation thereof are presented in FIGS. 22A-B.

FIG. 26 presents the chemical structure, two-step synthesis and cleavage mechanism by Cathepsin B of HPMA copolymer-Gly-Phe-Leu-Gly-PABC-Cy5-Quencher-PTX as an illustration for a FRET-based theranostic system synthesized by RAFT polymerization. The quencher-amine is coupled to the COOH end-functionalized HPMA copolymer-PTX-Cy5 conjugate, providing one quencher molecule per polymeric chain (FRET mode II). The functional monomers and preparation thereof, for synthesizing HPMA copolymer precursor are described in Example 8 hereinabove and in FIGS. 19A and 19B. The functionalized PTX and Cy5 moieties and the preparation thereof are presented in FIGS. 22A-B.

FIG. 27 presents the chemical structure, two-step synthesis and cleavage mechanism by Cathepsin B of HPMA copolymer-Gly-Phe-Leu-Gly-PABC-FITC-DR1-PTX as an illustration for a FRET-based theranostic system synthesized by RAFT polymerization. The quencher, DR1-amine is coupled to the COOH end-functionalized HPMA copolymer-PTX-FITC conjugate, providing one quencher molecule per polymeric chain (FRET mode II). The functional monomers and preparation thereof, for synthesizing HPMA copolymer precursor are described in Example 8 hereinabove and in FIGS. 19A and 19B. The functionalized PTX and FITC moieties and the preparation thereof are presented in FIGS. 22A-B.

FIG. 28 is a scheme depicting a synthesis of HPMA copolymer-Gly-Phe-Leu-Gly-PABC-Cy5-Quencher-PTX conjugate (FRET mode I), effected by conjugating Boc-NH-LG-PABC-PTX, Boc-NH-LG-PABC-Cy5 and a quencher to HPMA copolymer precursor bearing Gly-Phe-ONp/Gly-Gly-diamine Boc linkers, and addition of LG-PABC linker to PTX and Cy5 followed by their addition to the resulting conjugate HPMA copolymer-Gly-Phe-Leu-Gly-PABC-Cy5-Quencher-PTX. The functional monomers and preparation thereof, for synthesizing HPMA copolymer precursor are described in Example 8 hereinabove and in FIGS. 19A and 19B. The functionalized PTX and Cy5 moieties and the preparation thereof are presented in FIGS. 22A-B.

FIG. 29 is a scheme depicting a synthesis of HPMA copolymer-Gly-Phe-Leu-Gly-PABC-FITC-DR1-PTX conjugate (FRET mode I), effected by conjugating Boc-NH-LG-PABC-PTX, Boc-NH-LG-PABC-FITC and DR1 to HPMA copolymer precursor bearing Gly-Phe-ONp/Gly-Gly-diamine Boc linkers, and addition of LG-PABC linker to PTX and FITC followed by their addition to the resulting conjugate HPMA copolymer-Gly-Phe-Leu-Gly-PABC-FITC-DR1-PTX. The functional monomers and preparation thereof, for synthesizing HPMA copolymer precursor are described in Example 8 hereinabove and in FIGS. 19A and 19B. The functionalized PTX and FITC moieties and the preparation thereof are presented in FIGS. 22A-B.

FRET-Based Systems with PGA Conjugates (FRET Mode I):

A PGA-Cy5 conjugate was prepared according to the procedure described hereinabove (see, Example 2 and FIGS. 8A-B). A Quencher was thereafter conjugated to the polymeric backbone upon activating the unoccupied carboxylic groups of PGA with CDI coupling agent in a basic environment, as depicted in FIG. 30.

PGA was synthesized via the N-carboxyanydride (NCA) polymerization of glutamic acid, as shown in FIGS. 7A-D. The obtained polymer was dissolved in anhydrous N,N-Dimethylformamide (DMF) and mixed with carbonyldiimidazole (CDI) coupling reagent in order to activate the free polymer's carboxyl groups. The reaction mixture was stirred at room temperature for 4 hours in basic environment. The activated polymers was then added to Cy5-$NH_2$ (see, FIG. 8A), and the reaction mixture was stirred overnight at room temperature in basic environment. The reaction was followed by High Pressure Liquid Chromatography (HPLC) (UltiMate® 3000 Nano LC systems, Dionex). At the end of the reaction, the precipitate was washed with acetone:chloroform (4:1) solution and dried under vacuum. In order to remove excess of free fluorophore, the dried residue was dissolved in $NaHCO_2$ 0.2M buffer and dialyzed for 1 day at 4° C. (MWCO 6-8 kDa) against DI water. The obtained conjugate was purified by size exclusion chromatography (SEC) performed using AKTA/FPLC system (Pharmacia/GE Healthcare), HiTrap Desalting columns (Sephadex G-25 Superfine) in DDW, flow rate 1.0 ml/min; UV detection. Cy5 loading was determined using SpectraMax M5$^e$ multi-detection reader. The absorbance of conjugated Cy5 was measured and compared to that of free Cy5.

The obtained PGA-Cy5 conjugate was dissolved in an anhydrous DMF and mixed again with carbonyldiimidazole (CDI) coupling reagent in order to reactivate the unoccupied polymer's carboxyl groups. The reaction mixture was stirred at room temperature for 4 hours. The solution was removed to a round bottom flask containing Quencher-$NH_2$, and the reaction mixture was stirred overnight at room temperature in basic environment and was monitored by High Pressure Liquid Chromatography (HPLC) (UltiMate® 3000 Nano LC systems, Dionex). Once the reaction was completed, the precipitate was washed with acetone:chloroform (4:1) mixture and dried under vacuum. In order to remove the excess of free Quencher, the dried residue was dissolved in $NaHCO_2$ 0.2 M buffer and dialyzed for 1 day at 4° C. (MWCO 6-8 kDa) against DI water. The final purification of the conjugate by size exclusion chromatography (SEC) was performed using AKTA/FPLC system (Pharmacia/GE Healthcare), HiTrap Desalting columns (Sephadex G-25 Superfine) in DDW, flow rate 1.0 ml/min; UV detection. Quencher loading was determined using SpectraMax M5$^e$ multi-detection reader.

FRET-Based Systems with PEG Conjugates (FRET Mode IV):

A FRET-based probe-polymer conjugate for use as the diagnostic component in a theranostic system was designed, using Cy5 as a fluorophore, conjugated to the end (terminus) of polyethylene glycol (PEG) as the polymeric nanocarrier. The PEG-Cy5 conjugate was further conjugated via an analyte-cleavable linker to a quencher, to provide a PEG-Cy5-Q conjugate, forcing a Turn-OFF fluorescent state on the probe. An exemplary conjugate was designed to undergo specific activation by hydrogen peroxide, which is overproduced by various tumors, and therefore can be used as analyte for selective activation. Activation turns on a fluorescence signal through separation of the quencher from PEG-Cy5 conjugate, as depicted in FIG. 31B.

The PEG-Cy5-Q conjugate was synthesized as depicted in FIG. 31A. In brief, A FRET-based probe, actuvatable by hydrogen peroxide, was prepared as described in Redy et al., 2012 (supra), and was dissolved in a minimal amount of DMF. HBTU (4 equivalents) and DIPEA (15 equivalents) were added and the mixture was stirred for 30 minutes. Monofunctional PEG amine (13 kDa) was dissolved in DMF, heated to 50° C. and then was added to the mixture. The reaction was monitored using RP-HPLC. Upon completion, the obtained polymeric conjugate was purified using preparative HPLC.

The emitted fluorescence signal in the presence and absence of hydrogen peroxide was measured by.

The emitted fluorescence signal in the presence and absence of hydrogen peroxide was determined by incubation with and without hydrogen peroxide in PBS pH 7.4, while monitoring the emission using a spectrofluorometer ($\lambda_{ex}$– 630 nm, $\lambda_{em}$–670 nm). The results are presented in FIGS. 32A-B, and show the emission from the probe as a function of time after addition of hydrogen peroxide. A significant increase of the emitted fluorescence was observed within minutes after addition of hydrogen peroxide, whereas no change in fluorescence was observed in the absence of hydrogen peroxide. The conjugate exhibits stable Turn-OFF properties in the absence of hydrogen peroxide for several hours. Upon incubation with hydrogen peroxide, a gradual increase of the fluorescence signal was observed (i.e. Turn-ON) that reached saturation within approximately 3 hours. As shown in FIG. 32B, the signal was 10 times higher than the background as measured by HPLC and CRI Maestro™ imaging system.

The in vivo activation was measured following intravenous injection into tumor-bearing mice. Mice bearing U-87 MG tumors were injected with the PEG-Cy5-Q conjugate into the tail vein and the emitted fluorescence was monitored immediately following injection. At two minutes post injection, a strong fluorescence signal was observed in the tumor alone, as shown in FIG. 33, and retained for more than 6 hours (data not shown). These results indicate the selective activation of the conjugate at the tumor site.

Conjugating a therapeutically active agent to a conjugate as described herein provides a FRET-based PEG theranostic system (FRET mode IV).

Cathepsin B-Cleavable FRET-Based Fluorogenic Moiety (for Use in FRET Modes III and IV):

An exemplary FRET-based fluorogenic moiety (probe) which can be attached to a polymeric backbone by any of the approaches described herein, has been designed and synthesized.

The chemical structure and the activation mechanism of such a FRET-based probe is presented in FIG. 34. The probe is composed of Cy5 fluorescent dye attached through a cathepsin B substrate to a quencher dye. The selected cathepsin B substrate was the dipeptide Phe-Lys. The $NH_2$-terminus of the dipeptide was linked to Cy5 and the COOH-terminus was linked through a short self-immolative spacer to the quencher. Cleavage of the amide linkage after the lysine, followed by 1,6-elimination of the self-immolative spacer, results in separation between the Cy5 and the quencher. Consequently, a turn-ON NIR fluorescent signal is obtained from the emission of the Cy5 dye.

The chemical synthesis of the FRET-based probe is presented in FIG. 35. A phenylalanine amino acid was initially reacted with 1-(4,4-dimethyl-2,6-dioxocyclohex-1-ylidene)-3-methylbutyl (ivDde) protecting group, and the protected phenylalanine was coupled with 4-nitrophenol using N,N'-dicyclohexylcarbodiimide coupling reagent to obtain an ester. The latter was reacted with H-lys(Boc)-OH to give FK dipeptide, which was treated with 4-amino-benzylalcohol in the presence of N-methyl morpholine and isobutyl-chloroformate to give a benzylalcohol. The alcohol was activated with 4-nitrophenyl chloroformate to afford a carbonate. A Quencher moiety was deprotected with trifluoroacetic acid and then reacted with the carbonate to afford a carbamate. The carabamate was first deprotected using 2% of hydrazine in solution of DMF and then reacted with a Cy5-NHS derivative. The obtained crude product was treated with trifluoroacetic acid to remove the Boc-protecting group and to afford the probe.

A detailed synthetic protocol is described in Kisin-Finfer E., et al., 1; 24(11):2453-8; Bioorg Med Chem Lett. 2014.

The turn-ON response of the FRET-based probe upon reaction with cathepsin B was tested. The probe was incubated with cathepsin B in activity buffer solution (pH=6.0) and the NIR fluorescence emission was monitored using a spectrofluorometer. FIG. 36 shows the increase of the emitted fluorescence at wavelength of 670 nm upon incubation of the probe with cathepsin B, and the non-significant change in fluorescence in the absence of the enzyme.

The capability of the probe to serve as an imaging agent was determined by assessing the turn-ON response upon reaction with cathepsin B by the CRI Maestro™ imaging system. FIGS. 37A and 37B show the increase of the emitted fluorescence of the probe, 4 hours following the addition of cathepsin B.

An intravital imaging evaluation of the probes' fluorescence dependency on endogenous cathepsin B activity was tested by intra-tumoral injection to cathepsin B-overexpressing 4T1 mammary adenocarcinoma cells. The probe was injected intratumorally and the NIR fluorescence emission was monitored over 4 hours. The quantification of time-dependent fluorescence signal within the tumor is presented in FIG. 38. As shown therein, the probe presents a distinguishable increase in its NIR fluorescence over 4 hours after the injection into the tumors.

The exemplary FRET probe presented herein can be conjugated by means of, for example, cathepsin B cleavable linker, to a polymeric backbone, with or without a therapeutically active agent. Conjugation can be effected by attaching the probe to polymeric backbone units (FRET mode III), as exemplified hereinafter, or to the end of a polymeric backbone chain (FRET mode IV).

FRET-Based Systems with HPMA Conjugates (FRET Mode III):

A FRET-based probe such as described hereinabove can be attached to a portion of the backbone units of an HPMA precursor prepared by RAFT polymerization as described herein, so as to provide a fluorogenic moiety that generates a fluorescent signal upon cleavage of the FRET probe.

The synthesis, chemical structure and activation mode of a representative example of such a conjugate are presented in FIG. 39.

Alternatively, a FRET-based probe as described herein can be attached to a carboxylic group or any other terminal group of an HPMA precursor prepared by RAFT polymerization as described herein.

Further alternatively, a FRET-based probe as described herein can be attached via a cleavable linker (e.g., cathepsin B-cleavable linker) to a portion of the backbone units of PGA.

Example 10

ICT-Based Systems

Additional fluorogenic probes which can be attached to a polymeric backbone alone or in combination with a therapeutically active agent include fluorogenic probes which are activated by Internal Charge Transfer (ICT). A fluorogenic ICT-based probe is usually composed of a dye, masked by a substrate that acts as a trigger, as depicted in FIG. 40. The substrate is attached to a functional group of the dye and thus, masks the optical signal by decreasing or interfering with π-electrons conjugation. Removal of the triggering substrate by an analyte or an enzyme of interest results in release of the free dye and activation of a measurable signal, such as NIR fluorescence.

Fluorogenic ICT-based probes are described, for example, in WO 2012/123916. Such probes can be attached, for example, to a portion of the polymeric backbone units of HPMA (e.g., by attachment to HPMA precursor prepared by RAFT polymerization, as described herein).

FIG. 41 is a schematic illustration of the synthesis of HPMA copolymer-Gly-Gly-Phe-Lys-PABC-PTX-QCy7 by RAFT polymerization of copolymer precursor HPMA-Gly-Gly-ONp followed by coupling thereto amine-Phe-Lys- PABC-PTX, and amine-Phe-Lys-PABC-QCy7 as an example for ICT-based fluorescent Turn-On moiety.

The exemplary ICT-based probe shown in FIG. 40 has been demonstrated as highly efficient probe. See, Kisin-Finfer E., et al., 2014 (supra).

Any other fluorogenic ICT-based probes which are described, for example, in WO 2012/123916, can be attached to a portion of the backbone units of HPMA precursor prepared by RAFT polymerization, as described herein.

Alternatively, such ICT-based probes can be attached to a functional end (terminal) group of the polymeric backbone.

Further alternatively, such ICT-based probes can be attached to a portion of polymeric backbones of PGA, via a cleavable linker, in accordance with procedures as described herein.

When an ICT-based probe is attached to a polymeric backbone, a therapeutically active agent (drug) can be attached to another portion of the backbone units, so as to provide a theranostic system.

Alternatively, an ICT-based probe which further comprises a drug, and which is designed to release both the drug and a fluorescent dye upon cleavage of the trigger unit, can be attached to the polymeric backbone (either to a portion of the backbone units, via a cleavable linker, or to a terminal group of the backbone chain).

An exemplary such modular theranostic drug delivery system, which can be used in combination with a polymeric carrier according to any one of the embodiments described herein, is described herein.

The system is an example of a prodrug based on a latent fluorophore (fluorogenic moiety), which emits a fluorescence signal in the near-IR range upon activation, and which is further designed to release an anticancer drug such as camptothecin. Such probes can be designed so as to be attached to a polymeric carrier by enzymatically-cleavable linkers (e.g., cathepsin B cleavable linkers as described herein), such that upon cleavage, the drug is released and a fluorescent signal is generated. An exemplary such system, which can be attached, for example, to HPMA copolymer precursor prepared by RAFT polymerization or PGA polymeric backbone as described herein, and its mode of activation, is shown in FIG. 42.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A polymeric conjugate comprising a polymeric backbone composed of a plurality of backbone units and having attached to at least a portion of said backbone units a fluorogenic moiety, said fluorogenic moiety being attached to said portion of backbone units via a cleavable linking moiety such that upon cleavage of said linking moiety, a fluorescent moiety is generated, wherein said fluorescent moiety is a cyanine dye, and wherein the polymeric conjugate further comprises a quenching agent, the polymeric conjugate having a molecular weight in a range of from 10 kDa to 60 kDa, and is being such that said plurality of backbone units comprises two or more different portions of backbone units that differ from one another by the presence and/or nature of the moiety attached thereto, wherein one portion of the backbone units have said fluorogenic moiety attached thereto via said cleavable linking moiety and one another portion of the backbone units do not have a moiety attached thereto or have said quenching agent attached thereto, and wherein said different backbone units are randomly dispersed within said polymeric backbone, the polymeric conjugate being represented by Formula IA:

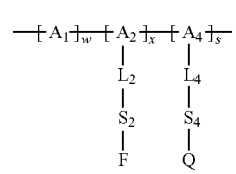

Formula IA wherein:

$A_1$, $A_2$ and $A_4$ are said backbone units;

F is said fluorogenic moiety;

Q is said quenching agent;

$L_2$ is said cleavable linking moiety, linking said fluorogenic moiety to each of backbone units $A_2$;

$S_2$ is a first spacer, linking said fluorogenic moiety to $L_2$, or is absent;

$L_4$ is a cleavable or non-cleavable linking moiety linking said quenching agent to backbone units $A_4$, or is absent;

$S_4$ is a spacer linking said quenching agent to $L_4$, or is absent;

w is an integer having a value such that w/(x+s+w) multiplied by 100 is in the range of from 70 to 99.9;

x is an integer having a value such that x/(x+s+w) multiplied by 100 is in the range of from 0.1 to 20; and s is a positive integer having a ratio to said x in a range of from 20:1 to 1:20, such that:

each [$A_2$-$L_2$-$S_2$-F] independently represents a backbone unit having attached thereto said fluorogenic moiety; and each [$A_4$-$L_4$-$S_4$-Q] independently represents a backbone unit having attached thereto said quenching agent, wherein said [$A_1$], [$A_2$-$L_2$-$S_2$-F] and [$A_4$-$L_4$-$S_4$-Q] backbone units are arranged in any order.

2. The polymeric conjugate of claim 1, wherein said fluorogenic moiety comprises a fluorescent moiety linked by a cleavable linking moiety and/or a degradable spacer to said quenching agent.

3. The polymeric conjugate of claim 2, wherein said fluorogenic moiety is represented by a formula selected from Formulae III and III*:

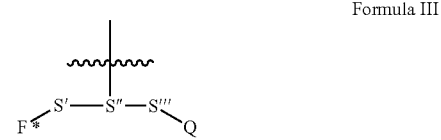

Formula III

-continued

Formula III*

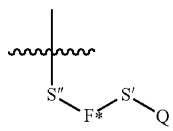

wherein:
the curled line indicates an attachment point;
F* is said fluorescent moiety;
Q is said quenching agent;
S' and S''' are each independently a degradable spacer, or absent; and
S'' is a multifunctional degradable spacer which connects said fluorogenic moiety to said cleavable linking moiety.

4. The polymeric conjugate of claim 1, wherein said fluorescent moiety has a Cy5 cyanine structure.

5. The polymeric conjugate of claim 3, wherein said fluorescent moiety has a Cy5 cyanine structure.

6. A polymeric conjugate comprising a polymeric backbone composed of a plurality of backbone units and having attached to at least a portion of said backbone units a fluorogenic moiety, said fluorogenic moiety being attached to said portion of backbone units via a cleavable linking moiety such that upon cleavage of said linking moiety, a fluorescent moiety is generated,
wherein:
the polymeric conjugate further comprises a quenching agent,
the polymeric conjugate having a molecular weight in a range of from 10 kDa to 60 kDa,
and said fluorescent moiety has a Cy5 cyanine structure,
and wherein the polymeric conjugate is such that said plurality of backbone units comprises two or more different portions of backbone units that differ from one another by the presence and/or nature of the moiety attached thereto, wherein one portion of the backbone units have said fluorogenic moiety attached thereto via said cleavable linking moiety and one another portion of the backbone units do not have a moiety attached thereto or have said quenching agent attached thereto, and wherein said different backbone units are randomly dispersed within said polymeric backbone,
the polymeric conjugate being represented by Formula IA:

Formula IA

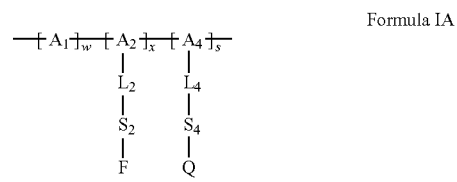

wherein:
$A_1$, $A_2$ and $A_4$ are said backbone units;
F is said fluorogenic moiety;
Q is said quenching agent;
$L_2$ is said cleavable linking moiety, linking said fluorogenic moiety to each of backbone units $A_2$;
$S_2$ is a first spacer, linking said fluorogenic moiety to $L_2$, or is absent;
$L_4$ is a cleavable or non-cleavable linking moiety linking said quenching agent to backbone units $A_4$, or is absent;
$S_4$ is a spacer linking said quenching agent to $L_4$, or is absent;
w is an integer having a value such that $w/(x+s+w)$ multiplied by 100 is in the range of from 70 to 99.9;
x is an integer having a value such that $x/(x+s+w)$ multiplied by 100 is in the range of from 0.1 to 20; and
s is a positive integer having a ratio to said x in a range of from 20:1 to 1:20, such that:
each [$A_2$-$L_2$-$S_2$-F] independently represents a backbone unit having attached thereto said fluorogenic moiety; and
each [$A_4$-$L_4$-$S_4$-Q] independently represents a backbone unit having attached thereto said quenching agent,
wherein said [$A_1$], [$A_2$-$L_2$-$S_2$-F] and [$A_4$-$L_4$-$S_4$-Q] backbone units are arranged in any order.

* * * * *

UNITED STATES PATENT AND TRADEMARK OFFICE
CERTIFICATE OF CORRECTION

PATENT NO. : 10,532,113 B2
APPLICATION NO. : 15/124360
DATED : January 14, 2020
INVENTOR(S) : Ronit Satchi-Fainaro et al.

Page 1 of 1

It is certified that error appears in the above-identified patent and that said Letters Patent is hereby corrected as shown below:

On the Title Page

Item (60) Related U.S. Application Data, Line 1, "61/852,259" should be changed to -- 61/952,259 --

Signed and Sealed this
Second Day of June, 2020

Andrei Iancu
*Director of the United States Patent and Trademark Office*